United States Patent [19]

Garvey et al.

[11] Patent Number: 5,409,946
[45] Date of Patent: Apr. 25, 1995

[54] ISOXAZOLE, ISOTHIAZOLE AND PYRAZOLE COMPOUNDS THAT ENHANCE COGNITIVE FUNCTION

[75] Inventors: David S. Garvey, Lake Forest; George M. Carrera, Jr., Des Plaines; Stephen P. Arneric, Lindenhurst, all of Ill.; Youe-Kong Shue, Sudbury, Mass.; Nan-Horng Lin, Mundelein, Ill.; Yun He, Milwaukee, Wis.; Edmund L. Lee, Lake Zurich; Suzanne A. Lebold, Chicago, both of Ill.

[73] Assignee: Abbott Laboratories, Abbott Park, Ill.

[21] Appl. No.: 118,079

[22] Filed: Sep. 8, 1993

Related U.S. Application Data

[63] Continuation-in-part of Ser. No. 706,920, May 29, 1991, abandoned.

[51] Int. Cl.⁶ .................. A61K 31/42; A61K 31/425; C07D 211/80
[52] U.S. Cl. .................. 514/372; 514/378; 514/406; 548/206; 548/214; 548/240; 548/247; 548/364.1
[58] Field of Search .............. 514/374, 378, 422, 454; 548/247, 206, 364.1, 214, 240

*Primary Examiner*—C. Warren Ivy
*Assistant Examiner*—A. A. Owens
*Attorney, Agent, or Firm*—Richard A. Elder

[57] ABSTRACT

Novel isoxazole isothiazole and pyrazole compounds of the formula:

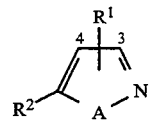

wherein A, $R^1$, and $R^2$ are specifically defined, or pharmaceutical salts thereof, are selective and potent cholinergic ligands at neuronal nicotinic receptors, useful in the treatment of cognitive, neurological and mental disorders characterized by decreased cholinergic function, as well as in the treatment of alcohol intoxication and petit real absence epilepsy.

13 Claims, No Drawings

ISOXAZOLE, ISOTHIAZOLE AND PYRAZOLE COMPOUNDS THAT ENHANCE COGNITIVE FUNCTION

This application is a continuation-in-part of copending PCT patent application PCT/US92/04631, filed May 28, 1992, now U.S. patent application Ser. No. 08/146,182, which is a continuation-in-part of U.S. patent application Ser. No. 07/706,920, filed May 29, 1991, now abandoned.

TECHNICAL FIELD

This invention relates to isoxazole, isothiazole and pyrazole compounds and pharmaceutical compositions thereof which are cholinergic ligands selective for neuronal nicotinic receptors, to methods for preparing these compounds, and to the use of such compounds to treat various cognitive, neurological and mental disorders, such as dementias and anxiety, which are characterized by decreased cholinergic function, to treat or prevent withdrawal symptoms caused by the cessation of chronic or long term use of tobacco products, to ameliorate the symptoms of anxiety and frustration associated with withdrawal of other addictive substances such as, for example, cocaine, diazepam or alcohol, and to treat alcohol intoxication and petit mal absence epilepsy.

BACKGROUND OF THE INVENTION

Dementia has been widely recognized as a very serious health problem. Alzheimer's disease, which has been identified by the National Institutes of Aging as accounting for more than 50% of dementia in the elderly, is also the fourth or fifth leading cause of death in Americans over 65 years of age. Four million Americans, 40% of Americans over age 85 (the fastest growing segment of the U.S. population), have Alzheimer's disease. Twenty-five percent of all patients with Parkinson's disease also suffer from Alzheimer's disease-like dementia. And in about 15% of patients with dementia, Alzheimer's disease and multi-infarct dementia coexist. The third most common cause of dementia, after Alzheimer's disease and vascular dementia, is cognitive impairment due to organic brain disease related directly to alcoholism, which occurs in about 10% of alcoholics.

The precise molecular lesion(s) that contribute to the morphological and functional deficits associated with dementia is unclear despite intensive research efforts over the last decade. However, the most consistent abnormality for Alzheimer's disease, as well as for vascular dementia and cognitive impairment due to organic brain disease related to alcoholism, is the degeneration of the cholinergic system arising from the basal forebrain (BF) to both the codex and hippocampus (Bigl et al., in *Brain Cholinergic Systems*, M. Steriade and D. Biesold, eds., Oxford University Press, Oxford, 1990, pp. 364–386). In particular, neurochemical evidence from the brains of patients afflicted with Alzheimer's disease has revealed reliable decreases in markers of cholinergic neuronal function (Perry et al., Br. Med. J. 1978, 2:1457; Reisine et al., Brain Res. 1978, 159:477; Coyle et al., Science 1983, 219.1184; and McGeer et al., Neurology 1984, 34:741). While there are a number of other neurotransmitter systems affected by Alzheimer's disease (Davies, Med. Res. Rev. 1983, 3.221), the relative occurrence of such abnormalities is less consistent or the effect is less profound than the decreases in these cholinergic neuronal function markers. More specifically, substantial reductions (30–50%) in nicotinic cholinergic receptors have been consistently reported in the brains of patients with Alzheimer's disease or Parkinson's disease (Kellar et al., Brain Res., 1987, 436:.62; and Whitehouse et al., Neurol 1988, 38:720), whereas changes in muscarinic cholinergic receptors are less remarkable and more dependent on receptor subtype.

However, degeneration of the cholinergic neurotransmitter system is not limited to individuals suffering from dementia. It has also been seen in otherwise healthy aged adults and rats. Decreases in cholinergic markers in the basal forebrain, decreases in cortical activities of the biosynthetic and degradative enzymes for acetylcholine, decreases in the ability to release acetylcholine from tissue slices, and decreases in numbers of cortical nicotinic receptors have all been reported in such otherwise healthy aged individuals (for a review, see Giacobini, J. Neurosci. Res. 1990, 27:548). Moreover, for those cholinergic neurons that remain, aging may cause a decrease in the temporal fidelity of existing impulse flow from the basal forebrain to the cortex (Aston-Jones et al., Brain Res. 1985, 325:271). Consistent with these findings are pharmacological studies suggesting that cholinergic mechanisms are, at least in part, responsible for the memory disturbances in aged animals and humans not suffering from Alzheimer's disease (Drachman and Leavitt, Arch. Neurol. 1974, 30:113; Bartus et al., Science 1982, 217:408).

Other clinical correlates associated with the neurodegenerative process of Alzheimer's disease include decreases in regional cerebral blood flow and cerebral glucose utilization, in regions which largely parallel the areas where cholinergic deficits occur (Ingvar and Risberg, Exp. Brain Res., 1962, 3:195; Ingvar et al., *Aging: Alzheimer's Disease, Senile Dementia and Related Disorders*, Vol. 7, R. Katzman, R. D. Terry, and K. L. Bick, eds., Raven Press, 1978, p. 203; and Dastur, J. Cerebral Blood Flow & Metabol., 1985, 5:1). In fact, it has been suggested that routine measurement of cerebral blood flow may be a useful procedure in evaluating patients suspected of having dementia, and of having Alzheimer's disease in particular.

Conflicting reports exist regarding the effect of aging on resting cerebral blood flow and cerebral glucose utilization in "normal, healthy" aged humans (Dastur, J. Cerebral Blood Flow & Metabol. 1985, 5:1, ) and rats (Smith et al.,Brain , 1980, 103:351; and Buchweitz-Milton and Weiss, Neurobiol. Aging, 1987, 8:55). Although decreases in cerebral blood flow and cerebral glucose utilization are generally reported in aged populations, it has been suggested that these decreases are secondary to other ongoing cerebral dysfunctions. Nonetheless, deficiencies in metabolic and cerebrovascular responses to pharmacologic and physiologic perturbation are consistently reported. Of particular interest is the recent finding in rats that increases in cerebral blood flow elicited by electrical stimulation of the basal forebrain shows age-related impairments (Linville and Arneric, Soc. Neurosci. Abstract, 1989, 15:17.5). Indeed, studies that compare the degree of learning impairment with the degree of reduced cortical cerebral blood flow in aged rats show a good correlation (Berman et al., Neurobiol. Aging, 1988, 9:691).

Recent clinical evidence suggests that the characteristic perfusion abnormality observed in Alzheimer's disease patients reflects regional nicotinic cholinergic deficits (Prohovnik, Neurobiol. Aging, 1990, 11:262). In particular, mecamylamine, a centrally-acting nicotinic receptor antagonist, reduces resting cortical perfusion in the parietotemporal cortex of humans, the area of the cortex most consistently found to be impaired in functional brain imaging of Alzheimer's disease patients. In agreement with this finding, regulation of cerebral blood flow in the frontoparietal cortex, governed by the basal forebrain, is also dependent upon nicotinic mechanisms in the rat (Arneric, J. Cerebral Blood Flow & Metabol., 1989, 9 (Suppl. 1): S502).

Chronic alcoholism, more particularly, the resultant organic brain disease, like Alzheimer's disease and normal aging, is also characterized by diffuse reductions in cortical cerebral blood flow in those brain regions where cholinergic neurons arise (basal forebrain) and to which they project (cerebral cortex) (Lofti & Meyer, Cerebrovasc. and Brain Metab. Rev, 1989, 1:2). Moreover, of all the neurotransmitter systems studied, the neurotoxic effects of alcohol on the cholinergic system are thought to be the most important.

Intuitively, regardless of specific etiologic process, therapies directed towards enhancing cognitive processing would be contingent upon maintaining a well-regulated balance between adequate cerebral blood flow, cerebral glucose utilization and cholinergic neurotransmission arising from the basal forebrain.

Pilot clinical studies suggest that nicotine may be useful for the acute treatment of deficits in attention and information processing associated with Alzheimer's disease (Sahakian et al., Brit. J. Psych., 1989, 154:797; Newhouse et al., Psychopharmacol., 1988, 95:171). It has been shown that both acutely and chronically-administered nicotine enhances cognitive function in rats (Levin et al., Behav. Neural Biol., 1990, 53.269), an effect that is also observed in aged animals (Cregan et al., Soc. Neurosci. Abstract, 1989, 15: 2952). Anecdotal evidence suggests a negative correlation between smoking by an individual and the likelihood of the individual acquiring Alzheimer's disease. These findings are supported by additional animal studies demonstrating a neuroregenerative/neuroprotective action of chronically-administered nicotine on both neuronal and vascular functions following hemitransection or MPTP-induced destruction of the nigro-striatal dopamine system (Janson et al., Prog. Brain Res., 1989, 79:257; and Owman et al., Prog. Brain Res., 1989, 79:267). Interestingly, in contrast to the classical down-regulation of receptors typically seen with receptor agonists, chronic nicotine administration up-regulates (50–100%) the number of receptors without affecting affinity (Benwell et al.,J. Neurochem., 1988, 50:1243). This effect occurs both in humans and in smaller animals such as rats (Lapchack et al., J. Neurochem., 1989, 52. 483 ).

Existing cholinergic agonists, however, are therapeutically sub-optimal. This is due to unfavorable pharmacokinetics (e.g., with arecoline and nicotine), poor potency and lack of selectivity (e.g., with RS-86), poor CNS penetration (e.g., with carbachol) or poor oral bioavailability (e.g., with nicotine). RS-86, for example, has similar affinity for cholinergic receptors located in the heart and in cortical tissues and is a full agonist at cardiac receptors, whereas it is only a partial agonist at cortical receptors (S. B. Freedman, British Journal of Pharmacology, 1986, 87: 29P). In addition, known agents have many unwanted central agonist actions, including hypothermia, hypolocomotion and tremor and peripheral side effects, including miosis, lacrimation, defecation and tachycardia (Benowitz et al., in: Nicotine Psychopharmacology, S. Wonnacott, M. A. H. Russell, & I. P. Stolerman, eds., Oxford University Press, Oxford, 1990, pp. 112-157; and M. Davidson, et al., in Current Research in Alzheimer Therapy, E. Giacobini and R. Becker, ed.; Taylor & Francis: New York, 1988; pp 333–336).

In addition to treating decline in cognitive ability by improving cholinergic function and cerebral blood flow, it is also desirable to symptomatically treat the other mental disorders accompanying the earlier stages of Alzheimer's disease. Anxiolytics have been used to treat the severe agitation that most Alzheimer's patients experience with the initial loss of memory (IN-PHARMA, March 16, 1991, pg 20). In fact, the use of anxiolytics has become an important aspect of treatment strategies for Alzheimer's disease (Schmidt et al., Drug Dev. Res., 1988, 14:251). Nicotine is known to have anxiolytic properties (Pomerleau et al., Addictive Behaviors, 1984, 9:265) and, therefore, nicotine or selective nicotine agonists may be useful in the treatment of the anxiety associated with dementias, such as Alzheimer's disease.

The neurotoxic effect of alcohol on the cholinergic system, discussed above, suggests that neuronal nicotinic receptor ligands, such as the novel compounds of the present invention, may therefore also be useful in the treatment of individuals suffering from acute alcohol intoxication, one of the most critical of medical emergencies. Without an effective treatment, an individual suffering from this condition may go into a coma or die, and unfortunately, few drug treatments for this condition are available to the emergency room physician.

Several drugs, such as amphetamine, picrotoxin, niketamide and caffeine, have been used in the past in order to treat acute alcohol intoxication (Lister & Nutt, Trends in Neuroscience, 10: 223, 1987). These treatments have met with little success due to the narrow therapeutic window of these agents. RO 15-451 3, a benzodiazepine receptor inverse agonist, has been reported to selectively antagonize the effects of ethanol in rats (Suzdak et al., Science, 234: 1243–1247, 1986), but the development of this compound for human use was discontinued because of its proconvulsant activity (Lister & Nutt, Trends in Neuroscience, 10: 223, 1987).

Recently, (−)-nicotine administered directly into the brains of rats was shown to significantly attenuate the motor incoordination due to the effects of ethanol administered intraperitoneally (Dar et al., Brain Res. Bull., 32:23–28, 1993). However, direct injection into the human brain is not a clinically-acceptable route of administration for routine use in a hospital or emergency room, and it is unclear whether these beneficial properties can be obtained using a more direct, more routine and clinically-acceptable route of systemic administration, such as intraperitoneal, intramuscular, intravenous, topical or oral delivery of the drug. The present application demonstrates that the novel neuronal nicotinic receptor ligands disclosed herein are effective in reducing ethanol narcosis when administered systemically (intraperitoneal delivery), whereas (−)-nicotine is not.

Other situations where beneficial therapeutic outcome may be achieved or improved through administration of nicotine or a nicotine agonist, because of the anxiolytic properties of these agents, include attentional deficit disorder, petit mal absence epilepsy and drug withdrawal.

Attention-deficit disorder (ADD), with or without hyperactivity, is a behavioral disorder characterized by distractibility and impulsiveness. Children with this disorder are handicapped by their inability to concentrate and control their impulsivity, especially in settings requiring sustained attention, for example, in school. While a cure for this disorder has not been found, stimulants, such as pemoline, have been used successfully in management of the behavioral manifestations of ADD. Nicotine, because of its ability to improve concentration and task performance (F. T. Etscorn, U.S. Pat. No. 4,597,961, issued Jul. 1, 1986; and D. M. Warburton and K. Wesnes in *Smoking Behavior*, R. E. Thornton, ed., Churchill-Livingston, Edinburgh, 1978, pp. 19–43) is also potentially useful in treating ADD.

Another situation where beneficial therapeutic outcome may be achieved or improved through administration of a neuronal nicotinic receptor ligand, because of the ability of these agents to control or prevent spike wave discharges associated with petit mal absence and impairments of mental function, include petit mal absence epilepsy.

Petit mal absence is a form of epilepsy characterized by lapses of consciousness that result in impairments of mental function. The five-second-to-two-minute attacks are accompanied by a blank facial stare with little or no apparent muscle activity, in sharp contrast to the massive tonic-clonic spasms of the entire body typical of grand mal epilepsy. Electroencephalographic (EEG) records of both grand mal and petit mal absence epilepsy patients are complex, but one diagnostic feature of the latter is a three-Hertz spike wave discharge not seen in grand mal. Petit mal absence epilepsy first appears in children four years of age or slightly older, but generally declines as the child goes through adolescence. The lapse of attention associated with petit mal absence can, however, be a significant problem in school age children. In a few cases, petit mal absence develops into primary generalized epilepsy during adulthood (Niedermeyer, in E. Niedermeyer and F. Lopes da Silva, eds., *Electroencephalography, Basic Principles, Clinical Application and Related Fields*, 1987, pp. 405–510). Currently-prescribed agents which attenuate spike wave discharges, such as benzodiazepines, unfortunately also produce undesirable side effects such as sedation and/or memory loss.

Tobacco use, especially cigarette smoking, has long been recognized as a major factor leading to disease and death. Approximately 4,000 by-products of combustion, many of which are known carcinogens, have been found in cigarette smoke. Of the three most-studied constituents of cigarette smoke, two, tars and carbon monoxide, have been found to cause or exacerbate numerous life-threatening disorders. Tars are most often implicated in the induction of lung, larynx, oral cavity, esophageal and other cancers, and are also thought to be responsible for respiratory diseases, including pulmonary emphysema, chronic bronchitis and smokers respiratory syndrome. Carbon monoxide, on the other hand, combines with hemoglobin in the blood thereby decreasing the ability of the blood to carry oxygen, and it has also been implicated as a causative agent in the development of coronary artery disease and arteriosclerosis. The third highly-studied, and the most pharmacologically-active substance, in tobacco products is nicotine, which is the reinforcing agent responsible for maintaining tobacco dependency and therefore exposing smokers to other threats of tobacco use (J. H. Jaffe in *Nicotine Pharmacology: Molecular, Cellular and Behavioral Aspects*, S. Wonnacott, M. A. H. Russell and I. P. Stolerman, eds., Oxford Science Publications, Oxford, 1990, pp. 1–37).

The nicotine withdrawal syndrome associated with smoking cessation is characterized by craving for nicotine, irritability, frustration or anger, anxiety, difficulty concentrating, restlessness, decreased heart rate and increased appetite and weight gain. Nicotine has, not surprisingly, been found to ease the withdrawal experienced by those attempting to break tobacco dependencies. As early as 1942, Johnston reported (L. Johnston, Lancet, 1942, 2.742) that injections of nicotine relieved the withdrawal symptoms experienced by cigarette smokers when they stopped smoking. More recently, in double-blind studies, nicotine was far superior to a placebo in suppressing or preventing the appearance of many of the signs and symptoms of withdrawal (J. R. Hughes et al., Psychopharmacology, 1984, 83:82-7; N. G. Schneider et al., Addictive Behavior, 1984, 9:149–56; R. J. West et al., Journal of Addiction, 1984, 79:215–9; K. O. Fagerstrom in *Nicotine Replacement; a Critical Evaluation*, O. F. Pomperleau and C. S. Pomperleau, eds., Alan R. Liss, Inc., New York, 1988, pp. 109–28,; and J. E. Henningfield and D. R. Jasinski, ibid, pp.35–61). Irritability and impatience were shown to have been reduced in at least five independent controlled studies, while anxiety and difficulty concentrating were shown to have been reduced in at least two studies. Other smoking-withdrawal symptoms for which nicotine was shown to have been significantly more effective than a placebo in relieving the condition in at least one study include depression, hunger, somatic complaints, and sociability. Nicotine has also been found to be effective in reducing anger, irritability, frustration and feelings of tension, while increasing the ability to focus upon the completion of tasks, without causing general response depression, drowsiness or sedation (R. R. Hutchinson et al., U.S. Pat. No. 3,879,794, issued Mar. 11, 1975).

One approach to alleviating the symptoms of tobacco withdrawal has been to develop more efficient methods of delivering nicotine, itself, for example, in transdermal patches (F. T. Etscorn, U.S. Pat. No. 4,597,961, issued Jul. 1, 1986). The major problem with this approach is the non-selective effects of nicotine and in particular, the stimulant effects of increasing cardiac workload and oxygen demand that nicotine has on the heart. A selective nicotine agonist would be expected to be equally efficacious in relieving withdrawal symptoms with fewer cardiovascular liabilities.

Withdrawal from addictive substances in general, regardless of which particular agent is withdrawn, is a traumatic experience characterized by anxiety and frustration. These emotional disturbances contribute to failure in therapy and, consequently, to a return to substance dependence. Although ameliorating these symptoms, including reducing anger, irritability, frustration and feelings of tension, does not eliminate the craving for the withdrawn drug, any agent improving the individual's ability to cope and to concentrate should vastly improve the chances of successfully completing withdrawal treatment.

Compounds somewhat similar to the novel therapeutic agents of the instant invention have been disclosed. The synthesis of certain 3,5-disubstituted isothiazoles has been reported by A. DeMunno and V. Bertini (Heterocycles, 1989, 29:97-102), who describe the preparation of 3,5-dimethyl isothiazole, 3-methyl-5-phenyl isothiazole, 3-methyl-5-hydroxymethyl isothiazole and 3,5-dihydroxymethyl isothiazole. Isothiazoles substituted at either the 3- or the 5-position with a heterocycle are neither disclosed nor suggested in this reference. Further, the isothiazoles disclosed by DeMunno and Bertinini have no known pharmacological activity.

Wadsworth and Jenkins in European Patent Application EP 402056, published Dec. 12, 1990, and P. A. Wyman in European Patent Application EP 413545, published Feb. 20, 1991 (both assigned to the Beecham Group) disclose certain non-aromatic 1-azabicyclic ring systems substituted in the 3-position by certain aromatic heterocycles, such as for example, triazole, tetrazole and oxadiazole. These compounds, however, are agonists at muscarinic receptors in the CNS.

Nielsen et al., in European Patent Application EP 316718, published May 24, 1989, disclose certain 3-4 dehydropiperidines substituted in the 3-position by oxazole, isoxazole, and isoxadiazole substituents for treating Alzheimer's disease, as opposed to the 2-substituted saturated ring compounds of the instant application.

Applicants have, however, discovered compounds new to the art which are useful in the treatment of the above disorders.

SUMMARY OF THE INVENTION

This invention relates to novel isoxazole, isothiazole and pyrazole compounds of the formula:

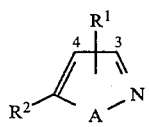

or pharmaceutical salts thereof, wherein A, $R^1$, and $R^2$ are specifically defined, which are selective and potent cholinergic ligands at neuronal nicotinic receptors and, therefore, may be used in the treatment of cognitive, neurological and mental disorders characterized by decreased cholinergic function, such as, for example, dementias and anxiety, in the treatment of attentional hyperactivity disorder and anxiety associated with cognitive impairment, substance abuse withdrawal, as well as in the treatment of alcohol intoxication and petit mal absence epilepsy.

The present invention is also directed to pharmaceutical compositions comprising a therapeutically-effective amount of a compound of the above formula and a pharmaceutically-acceptable carrier or diluent, as well as to a method of treating cognitive, neurological and mental disorders, which are characterized by decreased cholinergic function in humans and lower mammals, by administration of a therapeutically-effective amount of a compound of the above formula.

DETAILED DESCRIPTION OF THE INVENTION

The present invention is directed to compounds of the formula (I):

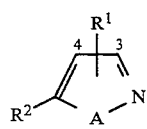

wherein
A is O, S, NH or N-phenyl;

$R^1$ is located at either position 3 or position 4 and is selected from the group consisting of, or $R^1$ is located at both positions 3 and 4 and is independently selected at each position from the group consisting of:
(i) hydrogen;
(ii) $C_1$–$C_6$-alkyl;
(iii) —$(CH_2)_aR^3$, wherein
  a is 1, 2, 3 or 4, and
  $R^3$ is $C_3$–$C_7$-cycloalkyl or phenyl;
(iv) —$(CH_2)_aOR^4$, wherein
  a is as defined above, and
  $R^4$ is $C_3$–$C_7$-cycloalkyl, phenyl or $C_1$–$C_6$-alkyl;
(v) —$(CH_2)_bNHR^4$, wherein
  b is 0, 1, 2, 3 or 4 and $R^4$ is as defined above;
(vi) $CF_3$;
(vii) halo;
(viii) halo—$C_1$–$C_6$-alkyl;
(ix) —$(CH_2)_aSR^4$, wherein a and $R^4$ are as defined above;
(x) OH;
(xi) —O—$C_1$–$C_6$-alkyl;
(xii) SH; and
(xiv) $NR^4R^4$, wherein $R^4$ is as defined above; and $R^2$ is selected from the group consisting of:

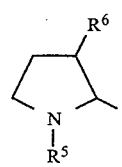

wherein
$R^5$ is H or $C_1$–$C_3$-alkyl, and
$R^6$ is H, F, $CH_2F$, CN, $NH_2$, $NHCO(C_1$–$C_6$-alkyl), —$CH_2CH=CH_2$ or $CH_2OR^9$, wherein $R^9$ is $C_1$–$C_3$-alkyl or —$CH_2CH=CH_2$;

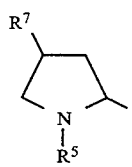

wherein
$R^5$ is as defined above, and
$R^7$ is H, OH, $C_1$–$C_3$-alkyl, or trans—$CH_2F$;

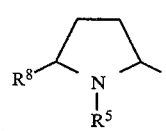

wherein
$R^5$ is as defined above, and
$R^8$ is H, trans—$C_1$–$C_3$-alkyl, or trans—$CH_2F$;

(iv)

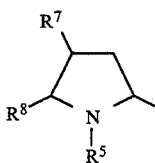

wherein
R$^5$, R$^7$ and R$^8$ are as defined above;

(v)

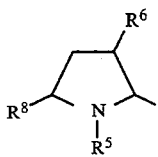

wherein R$^5$, R$^6$ and R$^8$ are as defined above;

(vi)

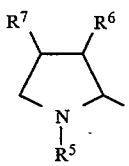

wherein R$^5$, R$^6$ and R$^7$ are as defined above;

(vii)

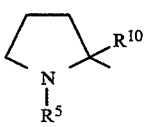

wherein
R$^5$ is as defined above, and
R$^{10}$ is H or C$_1$–C$_3$-alkyl;

(viii)

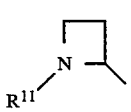

wherein
R$^{11}$ is C$_1$–C$_3$-alkyl; and (ix)

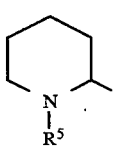

wherein
R$^5$ is defined above, and the stereochemistry at position 2 of formula (I) is (R) when R$^5$ is C$_1$–C$_3$-alkyl;
with the proviso that R$^5$ is always C$_1$'C$_3$-alkyl when R$^1$ is C$_3$- or C$_4$-alkyl or —(CH$_2$)$_a$R$^3$;
or a pharmaceutically-acceptable salt thereof.

Variables are understood to be independently selected at each occurrence.

In a more preferred embodiment of the invention, R$^1$ is at position 3 of the ring and is H, halo, C$_1$–C$_6$-alkyl, CF$_3$ or —O—C$_1$–C$_6$-alkyl, and R$^2$ is selected from alternate definition (ii), wherein R$^7$ is H or C$_1$–C$_3$-alkyl.

In a most preferred embodiment of the invention, R$^1$ is halo, C$_1$–C$_6$-alkyl, or CF$_3$, and R$^2$ is selected from alternate definition (ii), wherein R$^5$ is H or methyl, and R$^7$ is H.

The following are representative of the preferred compounds of the present invention:
3-Methyl-5-(2(S)-pyrrolidinyl)-isoxazole;
3-Methyl-5-(1-methyl-2(S)-pyrrolidinyl)-isoxazole;
3-Ethyl-5-(2(S)-pyrrolidinyl)-isoxazole;
3-Ethyl-5-(1-methyl-2(S)-pyrrolidinyl)-isoxazole;
3-Methyl-5-(2(S)-pyrrolidinyl)-isothiazole;
3-Methyl-5-(1-methyl-2(S)-pyrrolidinyl)-isothiazole;
3-Benzyl-5-(1-methyl-2(S)-pyrrolidinyl)-isoxazole;
5-(1-Methyl-2(S)-pyrrolidinyl)-3-propyl-isoxazole;
3-n-Butyl-5-(1-methyl-2(S)-pyrrolidinyl)-isoxazole;
5-(1-Ethyl-2(S)-pyrrolidinyl)-3-methyl-isoxazole;
3-Methyl-5-(1-methyl-2(R)-pyrrolidinyl)-isoxazole;
3-Methyl-5-(2(R)-pyrrolidinyl)-isoxazole;
3-Ethyl-5-(2(R)-pyrrolidinyl)-isoxazole;
3-Ethyl-5-(1-methyl-2(R)-pyrrolidinyl)-isoxazole;
3-Methyl-5-(2(R)-pyrrolidinyl)-isothiazole;
3-Methyl-5-(1-methyl-2(R)-pyrrolidinyl)-isoxazole;
3-Methoxymethyl-5-(1-methyl-2(S)-pyrrolidinyl)-isoxazole;
3-Methyl-5-(trans-4-hydroxy-1-methyl-2-pyrrolidinyl)-isoxazole;
3-Methyl-5-(trans-4-fluoromethyl-1-methyl-2-pyrrolidinyl)-isoxazole;
3-Methyl-5-(cis-1-methyl-5-cyanomethyl-2-pyrrolidinyl)-isoxazole;
3-Methyl-5-(trans-1,4-dimethyl-2-pyrrolidinyl)-isoxazole;
3-Methyl-5-(trans-1,5-methyl-2-pyrrolidinyl)-isoxazole;
3-Methyl-5-(trans-1-methyl-4-ethyl-2-pyrrolidinyl)-isoxazole;
3-Bromo-5-(1-methyl-2(S)-pyrrolidinyl)-isoxazole;
5-(trans-1-Ethyl-4-methyl-2(S)-pyrrolidinyl)-3-methyl-isoxazole;
5-(trans-1-Methyl-4-methyl-2(S)-pyrrolidinyl)-3-methyl-isoxazole;
5-(1-Methyl-2(S)-pyrrolidinyl)-3-methoxy-isoxazole;
3-Methyl-5-(trans-1-methyl-5-fluoromethyl-2-pyrrolidinyl)-isoxazole;
3-Methyl-5-(trans-1-methyl-3-fluoromethyl-2-pyrrolidinyl)-isoxazole;
3-Trifluoromethyl-5-(1-methyl-2(S)-pyrrolidinyl)-isoxazole;
3,4-Dimethyl-5-(1-methyl-2-pyrrolidinyl)-isoxazole;
5-(2-pyrrolidinyl)-isoxazole;
5-(1-Methyl-2-pyrrolidinyl)-isoxazole;
3-Methyl-5-(1-methyl-2(S)-pyrrolidinyl)-4-phenylmethyl-isoxazole;
3-Methyl-5-(1-methyl-2(S)-pyrrolidinyl)-4-ethyl-isoxazole;
3-Methyl-5-(2(R)-piperidinyl)-isoxazole;
3-Methyl-5-(1-methyl-2(R)-piperidinyl)-isoxazole;
3-Methyl-5-(2(S)-piperidinyl)-isoxazole;
3-Methyl-5-(2(S)-azetidinyl)-isoxazole;
3-Methyl-4-(1-methyl-2(S)-pyrrolidinyl)-1-phenyl-pyrazole; and
3-Methyl-5-(1-methyl-2(S)-pyrrolidinyl)-pyrazole;
and pharmaceutically-acceptable salts thereof.

The following are representative of more preferred compounds of the present invention:
3-Methyl-5-(1-methyl-2(S)-pyrrolidinyl)-isoxazole;
3-Ethyl-5-(1-methyl-2(S)-pyrrolidinyl)-isoxazole;

5-(1-Methyl-2(S)-pyrrolidinyl)-3-propyl-isoxazole;
3-n-Butyl-5-(1-methyl-2(S)-pyrrolidinyl)-isoxazole;
5-(1-Ethyl-2(S)-pyrrolidinyl)-3-methyl-isoxazole;
3-Methyl-5-(2(R)-pyrrolidinyl)-isoxazole;
3-Methyl-5-(1-methyl-2(R)-pyrrolidinyl)-isoxazole;
3-Ethyl-5-(2(R)-pyrrolidinyl)-isoxazole;
3-Ethyl-5-(1-methyl-2(R)-pyrrolidinyl)-isoxazole;
3-Methyl-5-(trans-1,4-dimethyl-2-pyrrolidinyl)-isoxazole;
3-Bromo-5-(1-methyl-2(S)-pyrrolidinyl)-isoxazole;
5-(trans-1-Ethyl-4-methyl-2(S)-pyrrolidinyl)-3-methylisoxazole;
5-(trans-1-Methyl-4-methyl-2(S)-pyrrolidinyl)-3-methyl-isoxazole;
3-(1-Methyl-2(S)-pyrrolidinyl)-3-methoxy-isoxazole; and
3-Trifluoromethyl-5-(1-methyl-2(S)-pyrrolidinyl)-isoxazole;
and pharmaceutically-acceptable salts thereof.

The following are representative of most preferred compounds of the present invention:
3-Methyl-5-(1-methyl-2(S)-pyrrolidinyl)-isoxazole;
3-Methyl-5-(2(R)-pyrrolidinyl)-isoxazole;
3-Bromo-5-(1-methyl-2(S)-pyrrolidinyl)-isoxazole; and
3-Trifluoromethyl-5-(1-methyl-2(S)-pyrrolidinyl)-isoxazole;
and pharmaceutically-acceptable salts thereof.

The novel isoxazole, isothiazole and pyrazole compounds of the invention and pharmaceutical compositions thereof are cholinergic ligands selective for neuronal nicotinic receptors and are useful for treating various cognitive, neurological and mental disorders, such as dementias and anxiety, which are characterized by decreased cholinergic function, for treating or preventing withdrawal symptoms caused by the cessation of chronic or long term use of tobacco products, as well as to a method of ameliorating the symptoms of anxiety and frustration associated with withdrawal of other addictive substances, for treating alcohol intoxication, and for treating petit mal absence epilepsy.

The terms "$C_1$-$C_3$-alkyl" and "$C_1$-$C_6$-alkyl" refer to branched or straight-chain, unsubstituted alkyl groups comprising one-to-four or one-to-six carbon atoms, including, but not limited to, methyl, ethyl, n-propyl, isopropyl, n-butyl, t-butyl, sec-butyl or isobutyl, or additionally, for $C_1$-$C_6$-alkyl, neopentyl or n-hexyl and the like.

The term "$C_3$-$C_7$-cycloalkyl" refers to a monocyclic saturated hydrocarbon ring containing three-to-seven carbon atoms in the ring.

The term "halo" or "halogen" as used herein refers to bromo (Br), chloro (Cl), fluoro (F) or iodo (I).

The term "haloalkyl" refers to an alkyl group of the designated size substituted with one halo group.

The term "phenyl" refers to an unsubstituted phenyl ring or a phenyl ring substituted with one or two substituents independently selected from nitro ($NO_2$), halogen, $C_1$-$C_4$-alkyl, $C_1$-$C_4$-alkoxy and $C_1$-$C_4$-alkylthio, or with none or one substituent as defined immediately above and one substituent selected from $C_1$-$C_4$-alkanoyl, di-$C_1$-$C_4$-alkylamino and methylenedioxy.

Compounds of the invention which have one or more asymmetric carbon atoms may exist as the optically-pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof. The terms "R" and "S" configuration used herein are as defined by IUPAC 1974 Recommendations for Section E, Fundamental Stereochemistry, Pure Appl. Chem., 1976, 45:13–30.

The compounds of the present invention may be synthesized as shown in reaction schemes I through IX presented below, in which $R^1$–$R^9$ are as defined above, except when specifically noted otherwise, and Y is a nitrogen protecting group, using the reactions and techniques described in this section. The reactions are performed in a solvent appropriate to the reagents, and materials employed are suitable for the transformations shown. It is understood by those skilled in the art of organic synthesis that the functionality present on the heterocyclic ring and other portions of the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to skilled practitioners in the art. The use of nitrogen-protecting groups is well known in the art for protecting amino groups against undesirable reactions during a synthetic procedure and many such protecting groups are known, c.f., T. H. Greene, *Protective Groups in Organic Synthesis*, Synthesis, John Wiley & Sons, New York (1981).

Scheme I

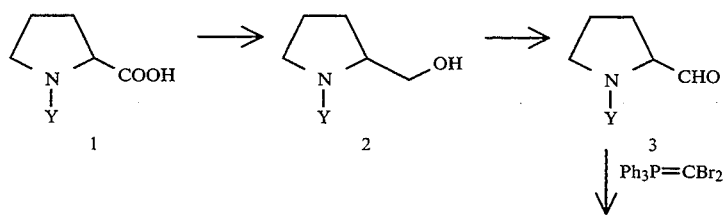

Scheme I

-continued

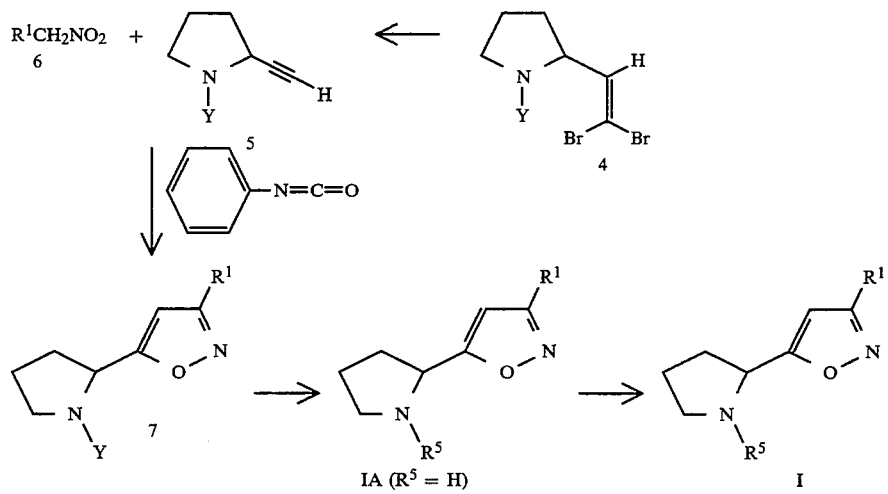

According to Scheme I isoxazole compounds of formula (I), wherein R¹ (excluding hydrogen) and R⁵ are defined as above, may be prepared according to reaction scheme I, in which monosubstituted pyrrolidine is representative of the saturated nitrogen-containing heterocycles as defined above. (R)- or (S)-proline with the ring nitrogen protected, for example as the t-butyloxycarbonyl (BOC) derivative, is reduced to a hydroxymethyl compound of formula 2 using a suitable reducing agent such as borane or borane-methyl sulfide complex. The hydroxymethyl compound of formula 2 is, in turn, oxidized using a suitable mild oxidizing agent such as DMSO/pyridine/sulfur trioxide, pyridinium chlorochromate (PCC) or DMSO/oxalyl chloride, to afford the aldehyde of formula 3. The aldehyde is then converted to a dibromovinyl compound of formula 4 by treatment with dibromomethyltriphenylphosphonium ylid under standard Wittig reaction conditions. The dibromovinyl compound is, in turn, treated with a suitable base, such as n-butyl lithium, to afford the acetylenic compound of formula 5. Synthetic methodology for preparing the compound of formula 5 are described by J. Y. L. Chung and J. Wasicak in Tetrahedron Letters, 1990, 31:3957. The acetylenic compound of formula 5 is allowed to react with a nitro compound of formula 6 in the presence of an isocyanate, such as phenyl isocyanate, chlorophenyl isocyanate, 1-naphthylisocyanate, o-tolyl isocyanate or ethyl isocyanate, preferably phenyl isocyanate, to afford the isoxazole compound of formula 7, the 1,3-dipolar cycloaddition product. The compound of formula 7 is then treated with a suitable reagent for removing the nitrogen protecting group. Treatment with a mild acid, such as trifluoroacetic acid or hydrogen chloride in glacial acetic acid, is preferred for removing a BOC group. The ring nitrogen is then alkylated, for example by treatment with formaldehyde and formic acid, or alternately by treatment with formaldehyde, in the presence of a suitable reducing agent (such as sodium cyanoborohydride), to afford a compound of formula (I). Alternatively, the ring nitrogen can be treated with an acid chloride or anhydride (such as acetyl chloride or acetic anhydride) in the presence of a base (such as triethylamine) to afford an amide which is then reduced with a suitable reducing agent (such as borane or lithium aluminum hydride) to afford a compound of formula (I).

Scheme II

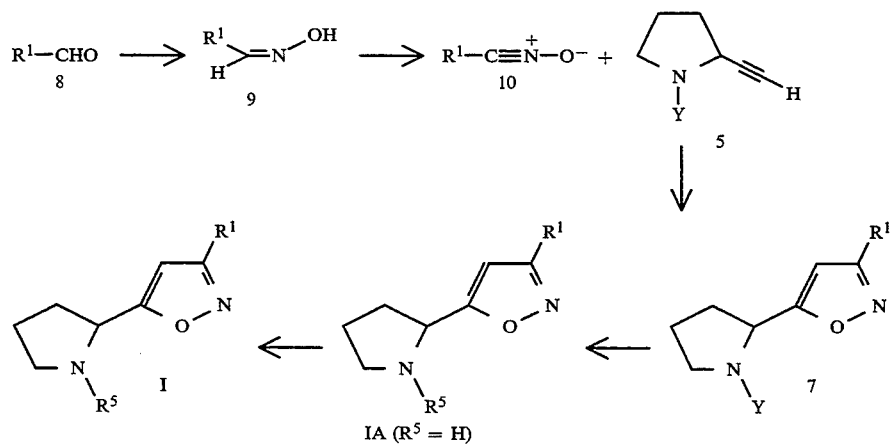

Alternately, compounds of formula (I), wherein R¹ (excluding hydrogen) and R⁵ are defined as above, may also be prepared according to reaction Scheme II, in which monosubstituted pyrrolidine is representative of the saturated nitrogen containing heterocycles. An aldehyde of formula 8 is treated with hydroxylamine to afford an oxime of formula 9. The oxime is, in turn oxidized, for example, by treatment with N-chlorosuccinimide or chlorine gas, and treated with a suitable base, such as triethylamine, to afford the corresponding nitrile oxide of formula 10. The acetylenic compound of formula 5 is allowed to react with the compound of formula 10 to afford the isoxazole compound of formula 7, the 1,3-dipolar cycloaddition product. The compound of formula 7 is then treated with a suitable reagent for removing the nitrogen protecting group. The ring nitrogen is alkylated, for example by treatment with formaldehyde and formic acid, or alternately by treatment with an aldehyde, such as formaldehyde, in the presence of a suitable reducing agent, such as sodium cyanoborohydride, to afford a compound of formula (I). Particularly useful methods of preparing enantiomerically-pure 3-methyl-5-(1-methyl-2(S)-pyrrolidinyl)isoxazole are described in U.S. patent application Ser. No. 08/117,819, filed concurrently herewith on Sep. 8, 1993, a CIP of U.S. patent application Ser. No. 07/981,587, filed Nov. 25, 1992, which CIP is incorporated herein by reference.

ated, for example by treatment with formaldehyde and formic acid, or alternately by treatment with an aldehyde, such as formaldehyde, in the presence of a suitable reducing agent such as sodium cyanoborohydride, to afford a compound of formula (I).

According to reaction Scheme IV, isoxazole compounds of formulas (II), (III), (IV) and (V), wherein $R^5$, $R^7$, and $R^8$ are defined as above, are prepared. A compound of formula 21 is allowed to react with an oxime dianion generated with a suitable base such as n-butyl lithium or LDA to give a β-keto oxime which is then cyclodehydrated with an acid such as sulfuric acid or with methanesulfonyl chloride and triethylamine to give the isoxazole of formula 22. The compound of formula 22 is allowed to react with borane to afford a compound of formula (II) (when $R^8$=H) or with an organometallic nucleophile which is subsequently reduced with a suitable reagent such as borane or lithium aluminum hydride to afford a compound of the formula (II) (when $R^8$=$C_1$-$C_3$-alkyl or phenyl).

Alternatively, the lactam anion of compound of formula 22 is generated with a suitable base such as LDA and reacted with various electrophiles to afford the

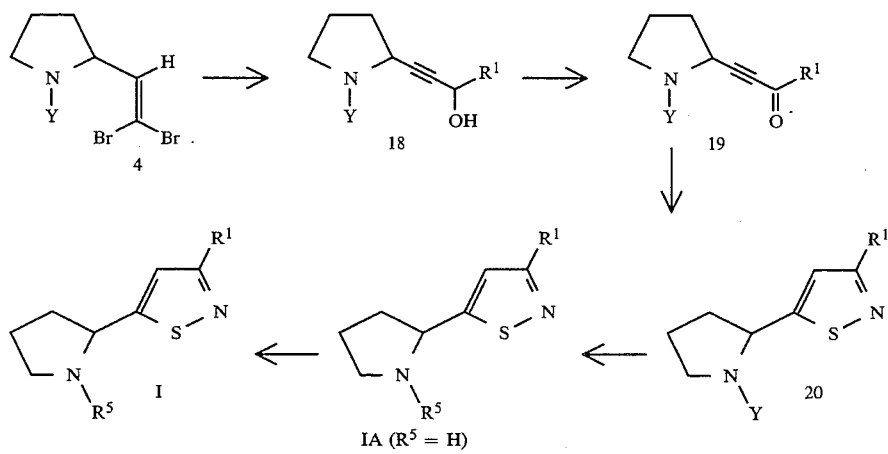

Scheme III

As a further alternative, isothiazole compounds of formula (I), wherein $R^1$ and $R^5$ are defined as above, are prepared according to reaction Scheme III, in which monosubstituted pyrrolidine is representative of the saturated nitrogen-containing heterocycles. A compound of formula 4 is allowed to react with an aldehyde in the presence of a suitable base, such as n-butyllithium, to give the alkynol of formula 18. The compound of formula 18 is, in turn, oxidized with an appropriate oxidizing agent, for example, DMSO/oxalyl chloride, tetrapropylammonium perruthenate/N-methyl morpholine N-oxide or DMSO/sulfur trioxide/pyridine, to afford the compound of formula 19. The compound of formula 19 is then treated sequentially with hydroxylamine-O-sulfonic acid, with a mild base (such as sodium bicarbonate), and with sodium hydrosulfide, in water or in a homogeneous mixture of water and a water-miscible solvent (for example methanol, THF or acetonitrile), to afford the compound of formula 20. The compound of formula 20 is treated with a suitable reagent for removing the nitrogen protecting group. Treatment with acid, such as trifluoroacetic acid or hydrogen chloride in glacial acetic acid, is preferred for removing a BOC protecting group. The ring nitrogen is then alkyl-compound of formula 23. The compound of formula 23 is then reduced to a compound of formula (III) by treatment with a suitable reducing agent, such as borane or lithium aluminum hydride.

Alternatively, the compound of formula 23 is allowed to react with an organometallic nucleophile and the product is reduced with a suitable reagent (such as borane or lithium aluminum hydride) to afford the compound of formula (IV). The lactam of formula 22 is converted to the thioamide of formula 24 by treatment with a suitable reagent such as Lawesson's Reagent or phosphorus pentasulfide. A thiolactam of formula 24 is allowed to react with a suitable Wittig reagent to afford the compound of formula 25. Reduction of the double bond within a compound of formula 25 (when $R^8$=$CH_2CN$) is achieved with a suitable reducing agent, such as sodium cyanoborohydride or hydrogen and a suitable catalyst, affording the compound of formula (II) ($R^8$=$CH_2CN$). Alternatively, unmasking the aldehyde (when $R^8$=$OCH_3$) and reduction with a suitable base, such as sodium borohydride, affords an alcohol which is treated with DAST to afford a compound of formula (II) ($R^8$=$CH_2F$).

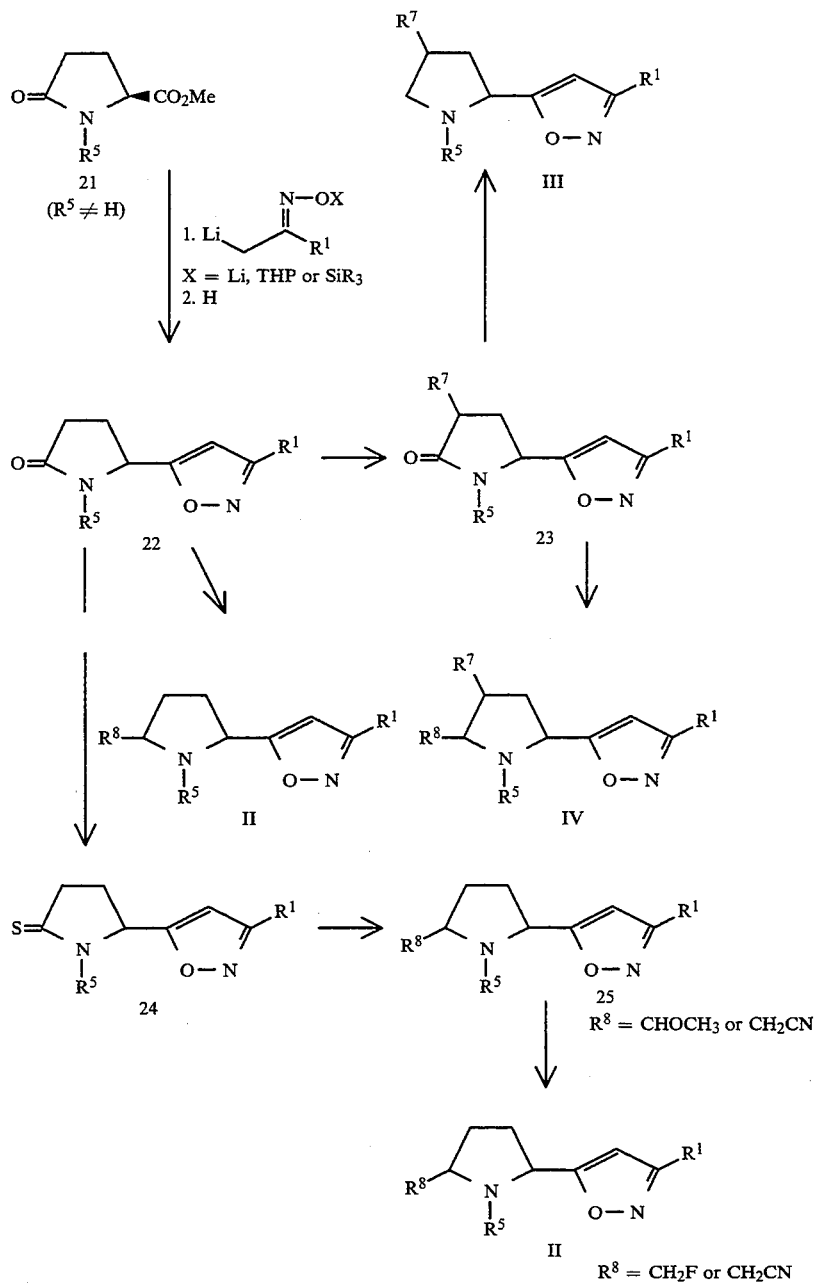
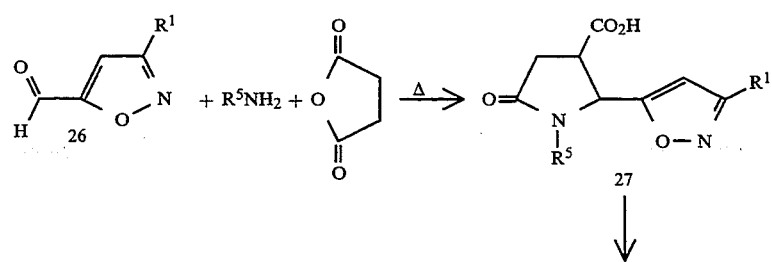

-continued
Scheme V

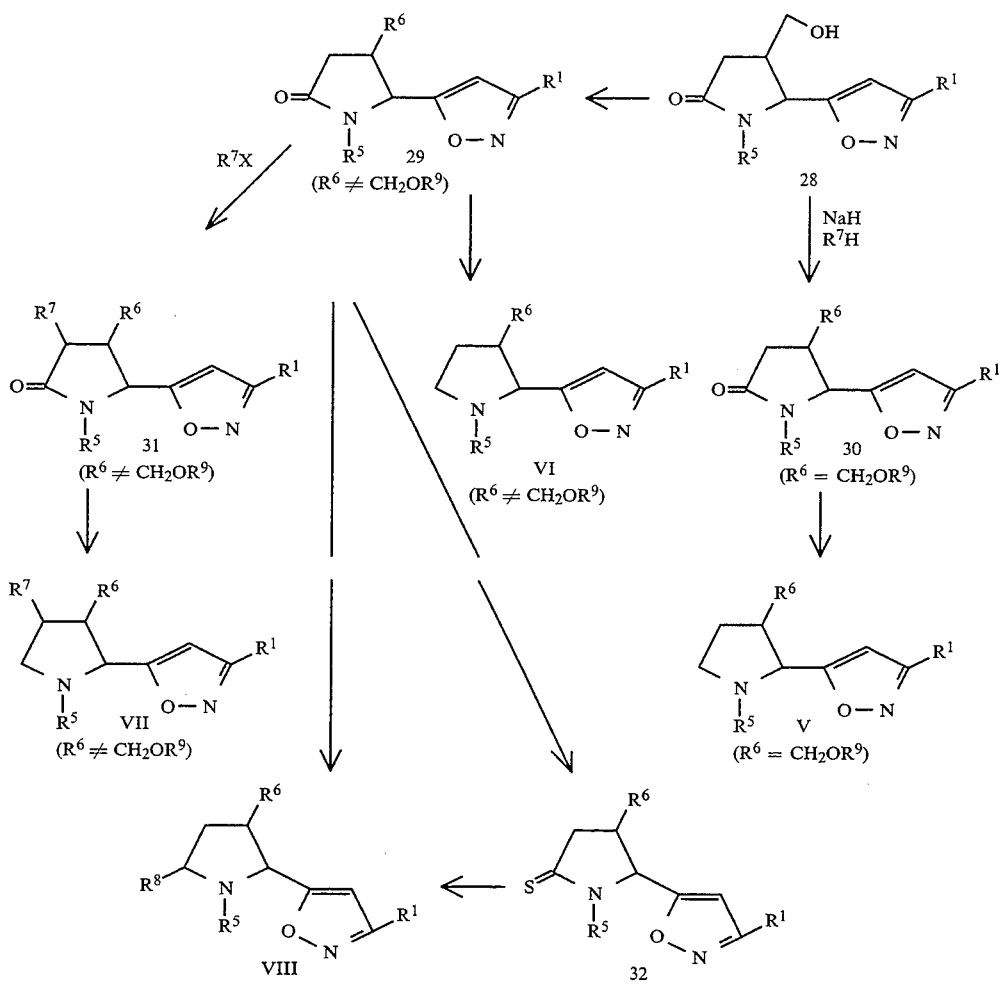

Isoxazole compounds of formulas (V), (VI), (VII) and (VIII), wherein $R^6$, $R^7$ and $R^8$ are defined as above or are the indicated subsets of the above definitions, may also be prepared according to reaction Scheme V. A compound of formula 26 is allowed to react with an amine and maleic anhydride to afford the acid of formula 27. The acid is then esterified with an alcohol, such as methanol, in the presence of an acid catalyst, such as hydrochloric acid. This ester is reduced to the alcohol of formula 28 with a reducing agent, such as sodium borohydride or diisobutylaluminum hydride. Generation of the alkoxy anion with an appropriate base, such as sodium hydride, followed by treatment with an electrophile affords a compound of formula 30. Reduction of the lactam with a suitable reagent, such as borane, affords the compound of formula (V).

Alternatively, conversion of the alcohol of formula 20 into a leaving group by treatment with a reagent such as methanesulfonyl chloride in the presence of a base, such as an alkali metal hydroxide, affords the compound of formula 29. Reduction of the lactam moiety with a suitable reagent, such as borane, affords the compound of formula (VI).

Alteratively, generation of the lactam anion of the compound of formula 29 with a suitable base, such as LDA, followed by subsequent treatment with an electrophile affords the compound of formula 31. Reduction of the lactam with a suitable reagent, such as borane, affords the compound of formula (VII).

Alternatively, the compound of formula 29 is allowed to react with an organometallic nucleophile, and the product is reduced with a suitable reagent, such as borane or lithium aluminum hydride, to afford the compound of formula (VIII). The lactam of formula 29 may be converted to the thiolactam of formula 32 then further converted to the compound of the formula (VIII) via the sequence described in Scheme IV.

Isoxazole compounds of formula (I), wherein $R^1$ is hydrogen, may also be prepared according to reaction Scheme VI, wherein a compound of the formula 3 is treated with formylmethylene triphenylphosphorane, resulting in the compound of formula 33. The oxime is then prepared by treatment with hydroxylamine hydrochloride in the presence of a base such as pyridine to give the compound of formula 34. Cyclization to the isoxazole of formula 35 is accomplished by the method described by G. Büchi and J. C. Vederas in J. Am. Chem. Soc., 94: 9128, 1972. Specifically, the $\alpha,\beta$-unsaturated oxime is treated with iodine and potassium iodide in a THF-$H_2O$ mixture to afford the compound of formula 35. The compound of formula 35 is then treated with a suitable reagent, such as trifluoroacetic acid or hydrogen chloride in glacial acetic acid for removing a BOC group, for removing the nitrogen protecting group. The ring nitrogen is then alkylated, for example, by treatment with formaldehyde and for- preferably according to the procedures described above, affords the compound of formula (I).

Scheme VI

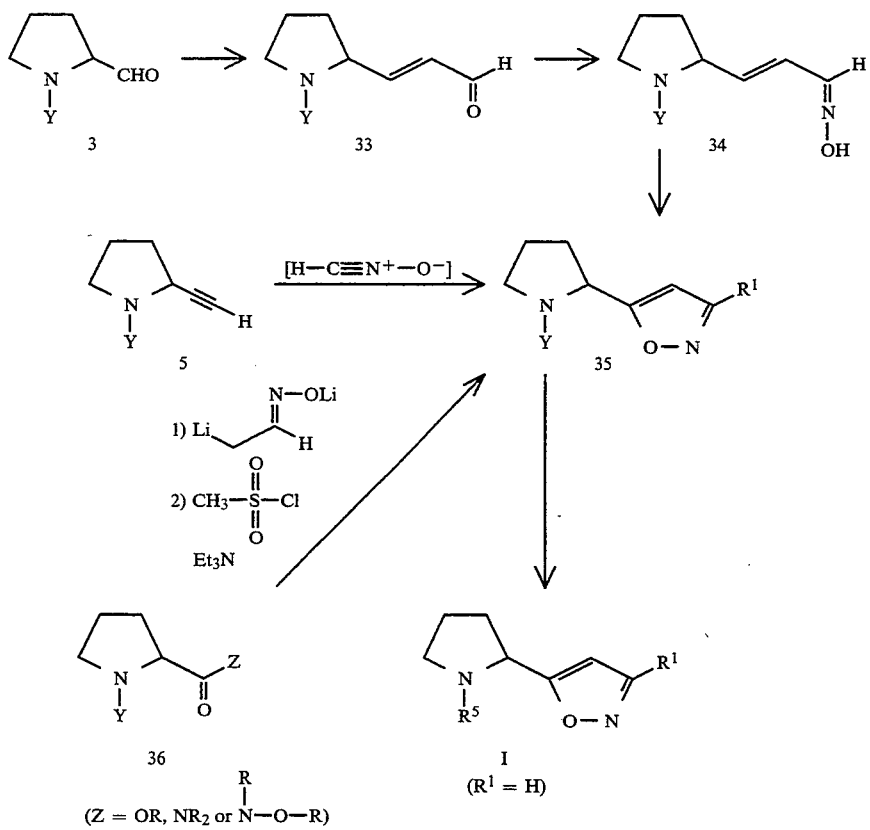

mic acid, or, alternatively, by first formation of the amide with a suitable anhydride such as acetic anhydride or acetic formic anhydride then reducing the amide with borane or lithium aluminum hydride.

Alternatively, the compound of formula 5 may be treated with fulminic acid generated preferably by the procedure of Huisgen and Christi (*Angew. Chem. Int. Ed. Engl.*, 1967, 6:456) to afford the compound of formula 35. Deprotection of the nitrogen and alkylation, Alternatively, the compound of formula 36 may be treated with the dianion of aldoxime to give a β-keto oxime which is then cyclized with an OH activating group such as methanesulfonylchloride in the presence of triethylamine, to afford the isoxazole of formula 35. Deprotection of the nitrogen and alkylation, preferably according to the procedures described above, affords the compound of formula (I).

Scheme VII

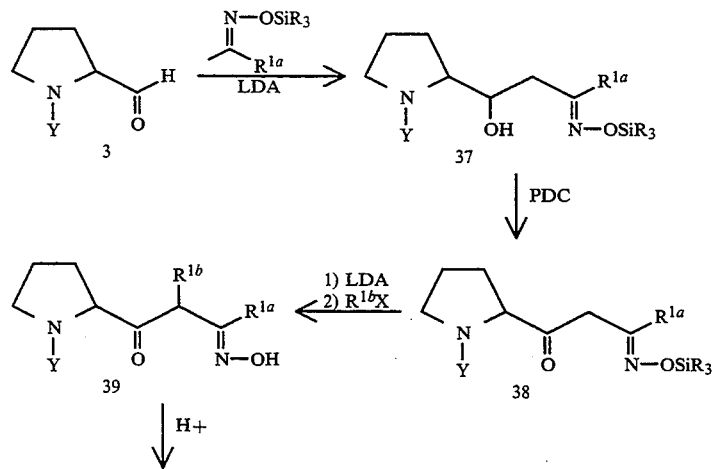

Scheme VII

-continued

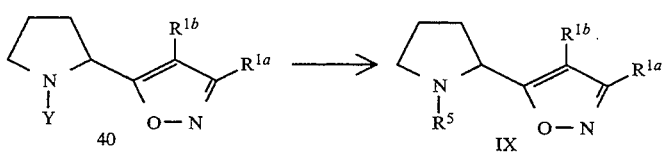

According to reaction Scheme VII, isoxazoles of formula (IX), wherein $R^{1a}$ and $R^{1b}$ are independently chosen from the definitions of $R^1$, and $R^1$ and $R^5$ are defined as above, may be prepared by first allowing a compound of formula 3 to react with an oxime carbanion of an O-protected oxime ($SiR_3$ is an acid labile protecting group such as tetrahydropyranyl or trimethylsilyl) to create the hydroxy compound of formula 37. Oxidation of the alcohol with an oxidant, such as pyridinium dichromate, affords the ketone of formula 38. Generation of the ketone anion with a base such as LDA, followed by treatment with a suitable electrophile, affords a compound of formula 39. The compound of formula 39 is then cyclodehydrated to an isoxazole of formula 40 by treatment with an acid, such as sulfuric acid, and that compound is treated with a suitable reagent for removing the nitrogen protecting group. The ring nitrogen is then alkylated, for example by treatment with formaldehyde and formic acid, or alternatively acylated by treatment with an acid chloride in the presence of triethylamine, to afford an amide which is then reduced with a suitable reducing agent, such as borane or lithium aluminum hydride, to afford a compound of formula (IX).

and formic acid or alternatively acylated by treatment with an acid chloride in the presence of triethylamine, to give compound 43. Compound 43 is then reacted with an oxime dianion generated with a suitable base, such as n-butyl lithium or LDA, to give a compound of formula 44. The ring is closed by reaction of the β-keto oxime by cyclodehydration with an acid, such as sulfuric acid or methanesulfonyl chloride and triethylamine, to give the isoxazole of formula 45. It will be obvious to those skilled in the art that this procedure may be combined with the procedures described in Scheme VII above, to generate compounds with alternate substitution on the isoxazole ring.

Scheme IX

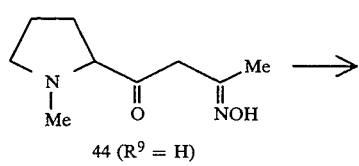

44 ($R^9$ = H)

Scheme VIII

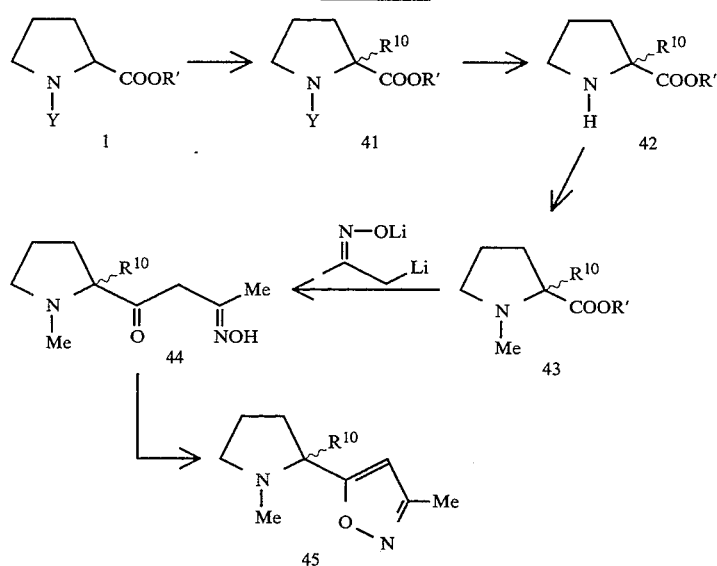

According to Scheme VIII, for the preparation of compounds of formula (I), wherein $R^2$ thereof is selected from option (vii) above, the compound of formula 1 is reacted with a strong base such as an alkali metal reagent, for example n-butyllithium, followed by reaction with a suitable nucleophile, such as an $C_1$–$C_3$-alkyl halide to give compound 41, wherein $R^{10}$ is $C_1$–$C_3$-alkyl. The protecting group is removed by suitable means as described above, and the ring nitrogen is alkylated, for example by treatment with formaldehyde

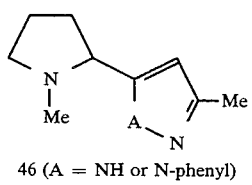

46 (A = NH or N-phenyl)

According to Scheme IX, for the preparation of compounds of formula (I), wherein A is NH or N-phenyl, a compound of formula 44, or alternately an appropriately-R⁶-, R⁷-, R⁸ - or R⁹-substituted analog of compound 44 (easily prepared by one skilled in the art by reference to the foregoing schemes) is reacted with hydrazine hydrochloride or phenylhydrazine hydrochloride by heating in the appropriate medium, such as for example, absolute alcohol or anhydrous THF or DMF.

For the preparation of compounds of formula (I) wherein $R^2$ is selected from option (viii), the skilled routineer may substitute as required for compounds 36, 1 or 3 of Schemes VI, VII or VIII the appropriately-protected four-member ring compound, such as N-protected azetidine-2-carboxylic acid compound (for compounds 1 and 36) or N-protected azetidine-2-carboxaldehyde (for compound 3). For the preparation of compounds of Formula (I) wherein $R^2$ is selected from option (ix), the skilled routineer may substitute as required for compounds 1,3 or 36 of Schemes VI, VII or VIII the appropriately-protected six-member ring compound, such as N-protected piperidine-2-carboxylic acid compound (for compounds 1 and 36) or N-protected piperidine-2-carboxaldehyde (for compound 3).

The compounds of the present invention may be used in the form of salts derived from inorganic or organic acids. These salts include but are not limited to the following: acetate, adipate, alginate, ascorbate, aspartate, benzoate, benzenesulfonate, bisulfate, borate, butyrate, camphorate, camphorsulfonate, citrate, cyclopentanepropionate, digluconate, dodecylsulfate, ethanesulfonate, fumarate, glucoheptonate, gluconate, glycerophosphate, hemisulfate, heptanoate, hexanoate, fumarate, hydrochloride, hydrobromide, hydroiodide, 2-hydroxy-ethanesulfonate, lactobionate, lactate, laurate, lauryl sulfate, maleate, methanesulfonate, nicotinate, 2-naphthalenesulfonate, oleate, oxalate, pamoate, palmitate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Also, the basic nitrogen-containing groups may be quaternized with such agents as $C_1-C_6$-alkyl halides, such as methyl, ethyl, propyl, and butyl chlorides, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenylethyl bromides, and others. Water- or oil-soluble or dispersible products are thereby obtained.

The pharmaceutically-acceptable salts of the present invention may be synthesized from the compounds of formula (I) by conventional chemical methods. Generally, the salts are prepared by treating the free amine with stoichiometric amounts or with an excess of the desired salt forming inorganic or organic acid in a suitable solvent or various combinations of solvents.

IN VITRO DETERMINATION OF NEURONAL NICOTINIC RECEPTOR BINDING POTENCIES AND SELECTIVITY

For the purpose of identifying compounds as cholinergic ligands capable of selectively interacting with nicotinic receptors in the brain, ligand-receptor binding assays were carried out as an initial screen. Initial screening indicated that the compounds of the present invention were effective at interacting with neuronal nicotinic receptors and they were, therefore, assayed for their ability (compared to (−)-nicotine) to displace radioligand from neuronal nicotinic receptors labeled with [³H]-methylcarbamylcholine ([³H]-MCC), or alternately, with [³H]-cytisine ([³H]-CYT). To further establish selectivity of the compounds for nicotinic, and not muscarinic receptors, the compounds were assayed for their ability (compared to (−)nicotine) to compete with the selective muscarinic antagonist [3H]-quinuclidinyl benzilate ([³H]QNB) for binding to muscarinic receptors.

The ability of the compounds of the invention to interact with cholinergic receptors and to act as cholinergic agonists can be demonstrated in vitro using the following protocols.

Protocols For Determination of Nicotinic Receptor Binding Potencies of ligands Binding of [³H]-methylcarbamylcholine ([³H]-MCC) or [³H]-cytisine ([³H]-CYT) to nicotinic receptors was accomplished using crude synaptic membrane preparations from whole rat brain (Snyder and Enna, Brain Research, 1975, 100:81). Washed membranes were stored at −80° C. prior to use. Frozen aliquots were slowly thawed and resuspended in 20 volumes of buffer (containing: 120 mM NaCl, 5 mM KCl, 2 mM MgCl₂, 2 mM CaCl₂ and 50 mM Tris-Cl, pH 7.4 @4° C). After centrifuging at 20,000 X g for 15 minutes, the pellets were resuspended in 30 volumes of buffer. Homogenate (containing 125–150 μg protein) was added to triplicate tubes containing concentrations of test compound and [³H]-MCC (3 nM) in a final volume of 500 μL. Samples were incubated for 60 minutes at 4° C., then rapidly filtered through Whatman GF/B filters presoaked in 0.5% polyethylimine using 3×4 mL of ice-cold buffer. Alternately, homogenate and test compound were incubated for 75 min with [³H]-CYT (1.3 nM), then rapidly filtered, as described above. The filters are counted in 4 mL of Ecolume ® (ICN). Nonspecific binding was determined in the presence of 10 μM (−)-nicotine and values were expressed as a percentage of total binding. IC₅₀ values were determined with the ALLFIT nonlinear least squares curve-fitting program and IC₅₀ values were converted to $K_i$ values using the Cheng and Prusoff correction ($K_i = IC_{50}/(1+[ligand]/K_d$ of ligand)). Alternately, data were expressed as a percentage of the total specific binding. The results are shown in Table 1.

These data suggest that the compounds of the present invention have high affinity for the neuronal nicotinic receptor, although they are slightly less potent than (−)-nicotine. The compounds of Example 2 and 4, however, both have 6 to 12-fold more affinity for the neuronal nicotinic receptor than arecoline, a nicotinic agonist that has demonstrated clinical utility.

TABLE 1

| Binding to Neuronal Nicotinic Receptors | | |
|---|---|---|
| Compound of Example Number | Nicotinic Receptor $K_i$ (nM) | Number of Determinations |
| (-)Nicotine | 1 | 4 |
| Arecoline | 59 | 4 |
| 1 | 289 | 4 |
| 2 | 5 | 3 |
| 3 | 621 | 5 |
| 4 | 9 | 3 |
| 6 | 222 | 3 |
| 7 | 18 | 2 |
| 8 | 13 | 3 |
| 9 | 14 | 3 |
| 10 | 24 | 3 |
| 11 | 3 | 7 |
| 12 | 7 | 5 |
| 13 | 34 | 3 |
| 14 | 10 | 2 |

TABLE 1-continued

Binding to Neuronal Nicotinic Receptors

| Compound of Example Number | Nicotinic Receptor $K_i$ (nM) | Number of Determinations |
|---|---|---|
| 15 | 7 | 3 |
| 16 | 55 | 2 |
| 17 | 12 | 3 |
| 18 | 71 | 3 |
| 19 | 228 | 3 |
| 20 | 22 | 3 |
| 21 | 114 | 3 |
| 22 | 183 | 3 |
| 24 | 24 | 3 |
| 25 | 289 | 3 |
| 27 | 7.7 | 3 |
| 28c | 21 | 2 |
| 28d | 17.1 | 3 |
| 29 | 62 | 3 |
| 32 | 6.1 | 3 |
| 36 | 77.6 | 3 |
| 37 | 105 | 3 |
| 38 | 386 | 2 |
| 39 | 357 | 2 |
| 40 | 283 | 2 |
| 41 | 2.5 | 3 |
| 42 | 145 | 4 |
| 43 | 228 | 3 |

Protocols For Determination of Muscarinic Receptor Binding Potencies of Ligands The potencies of ligand binding at central muscarinic binding sites were determined by analysis of competition with the specific muscarinic receptor radioligand [$^3$H]-quinuclidinyl benzilate ([$^3$H]-QNB). Binding of [$^3$H]-QNB to muscarinic receptors was carried out using crude synaptic membranes prepared from whole rat brains as described above. Competition between various concentrations of putative nicotinic ligand compounds and 0.2 nM [$^3$H]-QNB was performed at 25° C. in an assay volume of 1 mL. After 75 minutes, the bound radioligand was separated by vacuum filtration on Whatman GF/B glass fiber filters. Non-specific binding was defined as radioactivity remaining in the presence of 10 μM atropine. Competition curves were analyzed for $K_i$ values as described above for binding to the nicotinic receptor. The results are shown in Table 2.

TABLE 2

In Vitro Binding Affinities to Nicotinic and Muscarinic Receptors

| Compound | Nicotinic $K_i$ (nM) | Muscarinic $K_i$ (nM) | Muscarinic $K_i$ / Nicotinic $K_i$ |
|---|---|---|---|
| (−)-Nicotine | 1 | 587,000 | 587,000 |
| Arecoline | 59 | 5,000 | 85 |
| Example 2 | 5 | 160,000 | 32,000 |

These data suggest that the isoxazole compound of Example 2 is 32,000-fold more selective for the nicotinic receptor than for the muscarinic receptor. Although not as selective as (−)-nicotine, the compound of Example 2 is 376-fold more selective than is arecoline for nicotinic receptors.

IN VITRO CHOLINERGIC CHANNEL ACTIVATOR ACTION IN PC12 CELLS

The cholinergic channel activator properties of the compound of Example 2 were investigated in PC12 cells using the whole-cell patch-clamp approach to measure current flow through ligand-gated membrane channels, because the compound behaves as an agonist in animal behavior paradigms. The electrophysiological approach demonstrates clear agonist activity and indicates that this is due to direct activation of cholinergic ligand-gated channels.

PC12 cells are a rat pheochromocytoma cell line that, upon treatment with nerve growth factor (NGF) differentiate into a neuronal phenotype and express nicotinic cholinergic channels (Dichter et al., Nature, 1977 268:501; and Greene & Tischler, Proc. Natl. Acad. Sci, 1976 73: 2424). Neuronal cholinergic channel subunits found in these cells are 3, α5, β2, β3 and β4 (Rogers et al., J. Neurosci., 1992, 12: 4611; and Sargent, Ann. Rev. Neurosci., 1993, 16: 403). Thus, PC12 cells may be used to directly evaluate the ability of substances to activate or inhibit certain subtypes of neuronal nicotinic cholinergic channels.

Methods

PC12 cells were obtained initially from ATCC and, using standard techniques, were maintained in DMEM which contained 10% heat-inactivated fetal calf serum and 5% heat-inactivated horse serum (37° C., 95% $O_2$ & 5% $CO_2$). Electrophysiologic recordings were obtained from differentiated (neurite-bearing) cells after 4–7 days exposure to NGF. For this purpose, the undifferentiated cells were first plated onto polylysine-coated 12 mm round glass coverslips in 60×15 mm plastic Petri dishes. After 20 minutes, differentiating medium was added (DMEM containing 100 ng/ml nerve growth factor, 5% heat-inactivated fetal calf serum and 2.5% heat-inactivated horse serum) and the cells were refed with this medium every 3 days.

The whole-cell patch-clamp technique was used to record voltage-activated currents and ligand-gated currents activated by substances applied through the U-tube flow-reversal technique (Fenwick et al., J. Physiol., 1982, 331: 577). A coverslip bearing the cells was transferred from culture dish to the recording chamber (350 μl volume) and superfused (1 ml/min) at room temperature with an extracellular solution containing 150 mM NaCl, 2.8 mM KCl, 2.0 mM $CaCl_2$, 1.0 mM $MgCl_2$, ≧10 mM dextrose and 10 mM Na-HEPES buffer (7.3 pH, 325 mOsm). The intracellular (recording pipette) solution consisted of 140 mM KCl, 1.0 mM $CaCl_2$, 2.0 mM $MgCl_2$, 11 mM K-EGTA, and 10 mM K-HEPES buffer (7.3 pH, 315 mOsm). Osmolarities were adjusted using dextrose such that the extracellular solution was 10 mOsm hypertonic compared to the intracellular solution. Voltage-gated inward (sodium) and outward (potassium) currents were monitored throughout the experiment to determine establishment and maintenance of the whole-cell recording configuration.

After establishing the recording, cells were kept at a holding potential of −60 mV and cholinergic channel ligands dissolved in bathing solution were applied to the cells through computer-controlled U-tube flow reversal for a period of 5 seconds during which typical nicotinic desensitization was observed. The putative agonist was applied at least twice at each concentration in every cell, and applications were separated by ≧3 minutes to allow for recovery from desensitization, washout of the bathing solution, and re-equilibration of the U-tube. Antagonists were applied to the bathing solution through superfusion for several minutes prior to application of both antagonist and agonist through the U-tube.

Results

Some PC12 cells did not respond to (−)-nicotine even after treatment with NGF. In those that did, the peak inward current responses to 100 μM (−)-nicotine ranged from −40 pA to −420 pA in 13 differentiated PC12 cells. The compound of Example 2 (300 μM) elicited similar responses, ranging from −46 pA to −340 pA in 4 cells. The cholinergic channel antagonist mecamylamine (10 μM) inhibited the response to Example 2 (300 μM) by 81±3% (N=3).

In constructing dose-response relationships, each cell was exposed to several different concentrations of (−)-nicotine or the compound of Example 2 and the peak inward currents were measured. A graded dose-response relationship was evident in every cell. To combine data from different cells, a normalization was used to account for the variation in PC12 cell responsiveness. Each response to various concentrations of (−)-nicotine was normalized to the response to 100 μM (−)-nicotine obtained in the same cell; similarly, the responses to the compound of Example 2 were normalized to 300 μM Example 2. Furthermore, the standards (100 μM (−)-nicotine or 300 μM of the compound of Example 2) were applied at the beginning, end and often middle of every experiment with each cell in order to evaluate changes in the cell's response with time. The following equation was fit to the data using a nonlinear curve fitting program (SigmaPlot, Jandel Scientific):

$$I = I_{max} \times [A]^n / EC50^n + [A]^n$$

where I is the observed current response, $I_{max}$ is the maximal response, [A] is the agonist concentration, $EC_{50}$ is the agonist concentration that produces a half-maximal effect, and n is the Hill number.

Dose-response relationships were determined from 13 PC12 cells for (−)-nicotine, and 4 PC12 cells for the compound of Example 2. Fitting of the above equation to the data indicated the apparent potency of the compound of Example 2 was about 4-fold less than that of (−)-nicotine (Table 3). The Hill coefficient for the compound of Example 2 was approximately 1, and appeared to be smaller than that for (−)-nicotine.

TABLE 3

| In Vitro Dose-response relationships for the compound of Example 2 and (-)-nicotine in PC12 cells | | |
|---|---|---|
| Relationship | (-)- Nicotine | Example 2 |
| $EC_{50}$ (μM) | 52 ± 4 | 209 ± 76 |
| Hill coefficient (n) | 1.77 ± 0.18 | 1.18 ± 0.29 |

Values are mean ± S.E.M.

IN VIVO DETERMINATION OF NICOTINIC MODULATORY ACTION AFFECTING BASAL FOREBRAIN NEUROTRANSMISSION

Previous studies suggest that activation of neurons arising from the basal forebrain to the cerebral cortex will elicit an increase in cortical cerebral blood flow (CBF) by a mechanism that is mediated by a nicotinic receptor (see the Background section, above).

General Surgery for CBF Measurement

Methods for surgical preparation of rats for electrical stimulation of brain and measurement of CBF have been previously described (Nakai et al., Am. J. Physiol., 1982, 243: 226) and are summarized below.

Studies are conducted on male Sprague-Dawley rats that are maintained in a thermally-controlled (26°–27° C.), light-cycled (7.00 hour on–19.00 hour off) environment, fed standard rat chow and given water ad libitum. Anesthesia is induced with halothane (3.5%; balance $O_2$) delivered through a nose mask and maintained at 2% during the initial surgery. Thin-wall vinyl catheters (o.d.=0.03 inch) are placed in each femoral artery and vein, and the trachea is cannulated.

Animals are subsequently co-anesthetized with urethane (1.5 g/kg, s.c.) and placed in a stereotaxic frame with the head positioned so that the floor of the IVth ventricle was horizontal (incisor bar position: −11 mm.). After connecting the tracheal cannula to a small-animal respirator, the animals are temporarily paralyzed with d-tubocurarine (0.6 mg/kg/h, i.m.), and ventilated (80 cpm) with 100% $O_2$. Arterial pressure (AP) and heart rate (HR) are continuously monitored through one of the arterial catheters connected to a Statham P23Db transducer that is coupled to a chart recorder. The level of anesthesia during surgery or subsequent experimental testing is assessed by the AP response to tail pinch, with increasing levels of arousal giving rise to irregular AP readings. Booster doses of urethane (250 mg/kg, s.c.) are given as needed.

Bilateral craniotomies (approximately 4 mm×11 mm) are performed overlying the frontoparietal cortices taking care to leave the dura intact. Halothane is delivered at a reduced rate of 1% during cranial surgery and discontinued afterward. A small volume (about 0.2 ml) of arterial blood is sampled after completion of all surgery for measurement of $PO_2$, $PCO_2$ and pH by a blood gas analyzer. Arterial blood gases are maintained so that $PO_2$ was greater than 100 mm Hg, $PCO_2$=33–38 mmHg, and pH=7.35–7.45. Maintaining these values is accomplished by adjusting the stroke volume of the ventilator. Once appropriate physiological parameters are obtained (approximately 30 min), the experimental protocol is initiated.

Electrical Stimulation of the Basal Forebrain

The basal forebrain (BF) is stimulated with cathodal current delivered through a stainless steel concentric bipolar electrode (250 mm diameter) made by Rhodes Medical Instruments (Model SNEX-100). Electrical pulses are generated by a square wave stimulator (Grass, Model S-88) and constant current is passed through a photoelectric stimulus-isolation unit (Grass, Model PSIU6). The stimulus current is measured on an oscilloscope by continuously displaying the voltage drop across a 10-ohm resistor.

The procedure for eliciting an increased cortical CBF response requires the stereotaxic placement of the stimulating electrode into the BF. For positioning, the electrode is inclined posteriorly to 18 degrees, and the stereotaxic coordinates used were 5.0 mm posterior to, and 2.6 mm lateral to bregma (stereotaxic zero reference point). Cerebrovascular responsiveness, as measured by LDF, is used to localize the most active site of the BF by stimulating with 10 second trains of 2 msec duration pulses, at a frequency of 50 Hz and intensity of 100 μA. These parameters have been shown previously to elicit maximal increases in cortical CBF (Arneric, Excerpta Medica International Congress Series, 869:381, 1989). The region of the BF that selectively affects cortical CBF is restricted, with electrode movements of 0.5 mm dorsal or ventral to this site eliciting potent vasodepressor responses in addition to the increases in CBF. Thus, the vasodepressor responses are also used to help signal the approachment of the most active BF site. When CBF increases of approximately 100% or greater are repeatedly obtained in the absence of significant changes in AP (<10 mm Hg) or HR (<10 beats/min.), and when the perfusion rate is stable in the absence of BF stimulation, the experimental testing is started.

CBF Measurement with Laser-Doppler Flowmetry

The principles and technical aspects of laser-doppler flowmetry (LDF) are presented in detail in Bonner et al., Appl. Opt., 1981, 20:2097 and Stern et al., Am. J. Physiol., 1977, 232:H441. In brief, LDF is used to assess second-to-second changes in microvascular perfusion within a restricted region (1 cubic mm) immediately beneath the laser-doppler probe placed on dura. To monitor cortical CBF, an LDF probe (0.8 mm dia.) is attached to a micromanipulator and positioned over the exposed frontal CX. The probe is positioned to avoid major surface vessels and to touch the dura without significant surface indentation or occlusion of vessels. Careful exposure and manipulation of the frontal CX in this manner does not impair cerebrovascular reactivity (Arneric et al., Brain Res., 411:212, 1987). Responses to BF stimulations were assessed within a restricted cortical region (1.3–1.8 mm anterior to, and 3.2–3.9 mm lateral to bregma), defined as frontal CX, in order to select the coordinates giving the largest enhancement of cortical perfusion. The LDF monitor (BPM 403A, TSI Inc.) displays and records blood flow readings in absolute blood flow units (ml/min/100 g). However, for the experiments discussed, these values were treated as comparative numbers and used only to determine relative changes in blood flow.

Intravenous (i.v.) administration of the compound of Example 2 (0.4–0.6 $\mu$mol/kg) was examined for its effect on mean arterial pressure (MAP), resting CBF and increases in cortical CBF elicited by electrically stimulating the BF (@12.5 Hz; 100 $\mu$A; 10 second train). Consistent with the binding experiments, low concentrations were effective in enhancing resting CBF and the BF-elicited CBF response (n=3). No remarkable effects on MAP were observed (Table 4).

TABLE 4

| | Effect of the Compound of Example 2 on CBF and MAP | | |
|---|---|---|---|
| | % Change from Pre-Drug Control | | |
| dose ($\mu$mol/kg) | MAP | resting CBF | BF-elicited CBF |
| 0.004 | +5 | +5 | +68* |
| 0.040 | −5 | −2 | +60* |
| 0.400 | −13 | −6 | +68* |

*$p < 0.05$

These data indicate that administration of low concentrations of the compound of Example 2 effectively acts as an agonist at the neuronal nicotinic cholinergic receptor in vivo, since the basal forebrain-elicited cerebral blood flow response was enhanced. That compound showed itself to be 10- to 100-fold more potent in enhancing the cerebral blood flow response than previously reported for (−)nicotine (D. G. Linville and S. P. Americ, Soc. for Neurosci. Abstract, 1990, 16:129.11). These data are consistent with the idea that compounds like the compound of Example 2 are biologically more stable than (−)nicotine. Moreover, the compound of Example 2 has the advantage of having no overt effects on blood pressure, unlike those typically observed for direct-acting muscarinic agonists.

IN VIVO STUDIES DEMONSTRATING ACTIVITY AS COGNITION ENHANCERS

A. Inhibitory Avoidance Studies

The inhibitory (or sometimes called passive) avoidance (IA) test is a well-accepted animal model for learning/memory and is widely used to assess the activity of novel cognition enhancers in enhancing cognitive function (Wanibuchi et al., Eur. J. Pharmacol., 1990, 187:479). According to this test, animals are placed in the illuminated (12×14×11 cm) portion of a two-chambered box, from which they enter through a guillotine door to the larger (24×13.5×12 cm) dark compartment of the box. Entry to the dark compartment is accompanied by a mild (0.35 mA), brief (2 seconds) footshock. Initial latencies to cross are recorded, with an imposed 60 second ceiling. Following a 24 hour retention interval, animals are returned to the illuminated chamber, and latency to return to the dark compartment is again recorded, with a ceiling of 180 seconds. No footshock is administered on the test day.

Animals received systemic injections of (−)-nicotine or the compound of Example 2 (0.0036–3.6 $\mu$mol/kg, i.p.) 15 minutes before training in the inhibitory avoidance task, and retention was evaluated 24 hours later. Twelve animals were used in each group.

(−)-Nicotine induced a dose-dependent facilitation of retention of the avoidance response at 0.62 $\mu$mol/kg ($p<0.05$) (Table 5). The compound of Example 2 also significantly facilitated the retention of the avoidance response (Table 5). In fact, it was equally efficacious at 1/17th the dose of (−)-nicotine (i.e., at 0.036 $\mu$mol/kg, $p<0.05$).

B. Mouse Elevated Plus-Maze Studies

The mouse elevated plus-maze is a commonly-used conflict test that probes anxiolytic activity of test compounds (Lister, Psychopharmacology, 1987, 92 180). It is based on the fact that exposure of mice to an elevated open arm leads to an avoidance response considerably stronger than that evoked by exposure to an enclosed arm.

The apparatus required to perform this test is made of plywood and consists of two open arms (17×8 cm) and two enclosed arms (17×8×15 cm) extending from a central platform (8×8 cm). It is mounted on a plywood base rising 39 cm above the floor. Mice are released on the central platform and the time spent in the open and enclosed arms is recorded during a 5 minute test period.

(−)-Nicotine (0.62 and 1.9 $\mu$mol/kg, i.p., $p<0.05$) induced a significant increase in the time spent by the mice in the open arms of the maze (a measure of anxiolytic effect) as compared to saline-injected mice (Table 5). By comparison, the compound of Example 2 had an anxiolytic effect similar to (−)-nicotine, but was at least 10-fold more potent (Table 5). The compound of Example 2 (0.0108–1.08 $\mu$mol/kg, i.p.) was administered to CD1 mice (n=12 per group) 15 minutes before the test. There was a clear anxiolytic response in mice receiving 0.036–1.08 $\mu$mol/kg of the compound of Example 2 ($p<0.05$), as these groups of mice spent significantly more time in the open arms of the maze as compared to control animals.

TABLE 5

| Inhibitory Avoidance (IA) and Elevated Plus-Maze (EPM) | | |
|---|---|---|
| Example # | IA | EPM |
| (-)-nicotine | significant [0.62] | significant [0.62–1.9] |
| Example 2 | significant [0.036] | significant [0.036–1.08] |

*Results are expressed in levels of improvement in performance at the dose range (in micromol/kg) tested.

IN VIVO STUDIES DEMONSTRATING ACTIVITY AS ALCOHOL ANTAGONISTS

It is known that administration of ethanol to mice induces a state of narcosis in the animals. In mice, after a dose of 4 g/kg of ethanol, this is demonstrated by the loss of the righting reflex, which is followed by a period of sleep. It is also known that certain compounds can modify the narcotic effect of ethanol in this model. Compounds like diazepam or pentobarbital potentiate the effect of ethanol by increasing the sleep time. Compounds that reduce the sleep time induced by ethanol are considered alcohol antagonists, and such compounds would have potential value for treating alcohol intoxication in humans.

Methods

Animals: Male CD1 mice (Charles-River Co., Portage, Mich.) weighing 25–30 g were used in the experiments. Upon arrival they were caged in groups of 14 and allowed to acclimatize to laboratory conditions for one week before the beginning of the studies. They were fed standard rodent diet with food and water ad libitum.

Duration of sleep time: Mice received intraperitoneal (i.p.) injections of ethanol and either saline or one of the drug treatments. Upon loss of the righting reflex, a timer was started to record the duration of the sleep time until the reflex was recovered. Two types of experiments were conducted to study the effect of drugs before (pre-treatment) or after (post-treatment) the injection of the narcotic dose of ethanol. In the pre-treatment experiments the drugs were injected i.p., 15 minutes before ethanol. In the post-treatment experiments the drugs were administered i.p., 1 minute after the animals lost the righting reflex, which was approximately 5 minutes after administration of ethanol.

Drugs: Ethanol was prepared as a 20% v/v (16% w/v) solution in saline. Based on previous studies, a dose of 87 mmol/kg (4 g/kg) was selected as the narcotic dose. RO 15-4513, the benzodiazepine receptor inverse agonist discussed in the Background section, was purchased from RBI (Natick, Mass.). It was dissolved in saline solution with Tween-80 and ultrasonically homogenized for 3 minutes. (−)-Nicotine bitartrate (Sigma) was dissolved in saline solution. The compounds of Examples 2 and 4, both novel neuronal nicotinic receptor ligands according to the present invention, were also dissolved in saline to the desired concentrations.

Results

Table 6 shows the effect of the different drugs on ethanol-induced narcosis. The pre-treatment with RO 15-4513 or (−)-nicotine significantly reduced the sleeping time of ethanol in mice, while the post-treatment with the same agents significantly prolonged the narcotic effect of ethanol (p<0.05, one-tailed "t" test).

The data of Table 6 indicate that RO 15-4513 and (−)-nicotine reduce the effects of ethanol-induced narcosis only when given prior to alcohol. When administered after the alcohol, however, they adversely potentiated the narcotic effect.

TABLE 6

Antagonist Effect of Pretreatment with RO 15-4513 and (-)- Nicotine on the Narcotic Effect of Ethanol

| Drug treatment (μmol/kg) | Sleeping time (% of controls) |
|---|---|
| RO 15-14513 (pre) | |
| 0 | 100 ± 19 |
| 1 | 101 ± 9 |
| 3 | 107 ± 19 |
| 10 | 79 ± 6 |
| 30 | 57 ± 14* |
| RO 15-4513 (post) | |
| 0 | 100 ± 15 |
| 1 | 84 ± 14 |
| 3 | 165 ± 22* |
| 10 | 118 ± 13 |
| 30 | 73 ± 11 |
| (-)- Nicotine (pre) | |
| 0 | 100 ± 13 |
| 0.62 | 105 ± 18 |
| 1.9 | 85 ± 13 |
| 6.2 | 77 ± 17 |
| 19 | 46 ± 16* |
| (-)- Nicotine (post) | |
| 0 | 100 ± 11 |
| 0.62 | 121 ± 18 |
| 1.9 | 149 ± 28 |
| 6.2 | 164 ± 32* |
| 19 | 232 ± 29* |

*statistically significant

Table 7 shows the effect of the post-treatment of ethanol-induced narcosis with the nicotinic receptor ligands of Examples 2 and 4. In contrast to RO 15-4513 and (−)-nicotine (Table 6), the compounds of Examples 2 and 4 significantly reduced (p<0.05, one-tailed "t" test) the effects of ethanol-induced narcosis when administered after alcohol. The test compounds of Examples 2 and 4 differ only in their chiral configuration, and equal activity was seen from the (S)- and (R)- enantiomeric configurations. The evidence thus supports the potential of these compounds for therapeutic use in treating patients who are severely intoxicated with alcohol or who are already in a state of alcohol-induced coma.

TABLE 7

Antagonist Effect of Post-treatment with Compounds of Example 2 and Example 4 on the Narcotic Effect of Ethanol

| Drug treatment (μmol/kg) | Sleeping time (% of controls) |
|---|---|
| Example 2 (post) | |
| 0 | 100 ± 10 |
| 0.062 | 91 ± 20 |
| 0.19 | 68 ± 15 |
| 0.62 | 51 ± 8* |
| Example 4 (post) | |
| 0 | 100 ± 18 |
| 0.062 | 73 ± 12 |
| 0.19 | 61 ± 7* |
| 0.62 | 59 ± 8* |

*statistically significant

IN VIVO STUDIES DEMONSTRATING ACTIVITY IN CONTROLLING PETIT MAL ABSENCE EPILEPSY

It is known that Wistar rats spontaneously exhibit petit mal absence-like spike wave discharges (Vergnes et al., Dev. Brain Res., 30: 85, 1986 ), and that these spike wave discharges are correlated with memory impairments (Aldinio et al., Meth. and Find. Exptl. Clin. Pharmacol., 7: 563, 1985; and Radek et al., Brain Res. Bull., in press, 1993). It has also been shown that drugs used for the treatment of human petit real absence seizures also attenuate spike wave discharges in the Wistar-derived WAG/Rij strain of rats (Peeters et al., Neurosci. Res. Comm., 2: 93, 1988 ). Thus, this rat model is useful as a screen to test for compounds that lower the incidence of spike-wave discharges, and may be said to be a measure of the effectiveness of a compound in treating petit mal absence epilepsy. As such, this model may identify compounds that are candidates for treatment of petit mal epsilepsy in humans.

Methods

Animals: Male albino rats of the Wistar strain (CAMM Research) were maintained on a 12:12 hour light-dark cycle and individually housed throughout these experiments. They were fed standard rodent diet with food and water provided ad libitum.

EEG Recordings: To record spike wave discharges, rats were surgically implanted with permanently affixed EEG electrodes over the frontal codex using previously described techniques (Radek, Brain Res., 1993, in press). After at least a ten day recovery from this surgery, EEG recordings were made inside darkened sound attenuating chambers. Rats were allowed to move freely within the chambers and computerized activity monitors recorded animal motion during these studies. Only those rats that express spike wave discharges, as identified from preliminary recordings, were used to test the effects of nicotinic agents.

Drug studies: EEG recordings were obtained from each rat for a period of 20 minutes of total waking immobility immediately after administration of drug, or a drug-free control solution. Immobility was characterized as the absence of infrared beam interruptions from the activity monitor system. Spike wave activity was identified as regular 6–10 Hz complexes with amplitudes of 0.4 to 1.0 mV. The total spindling duration for 20 minutes of waking immobility was calculated by determining the length (in seconds) of each spike wave burst, and adding each of these times together to obtain a total spindle time for the recording session. Each rat was administered the control solution and one or two doses of the test compounds and each dosing was given at least 48 hours after the previous treatment.

Drugs: (—)-Nicotine bitartrate, mecamylamine and diazepam were obtained separately from Sigma Chemical Company and dissolved in saline (0.9% NaCl). The compound of Example 2 was dissolved in saline to the desired concentration.

Results

Table 8 shows an experiment which compares the utility of (—)-nicotine with the compound of Example 2 in reducing rat spike wave discharges, as a measure of the latter compound's potential to reduce such petit mal absence-type spike wave discharges.

The i.p. administration of (—)-nicotine (0.62 & 1.9 μmol/kg) or the compound of Example 2 (1.9 & 6.2 μmol/kg) significantly lowered the incidence of spike wave discharges during 20 minutes of waking immobility ($p < 0.05$, 2-way ANOVA). (—)-Nicotine and the compound of Example 2 have spike wave-attenuating properties similar those of the anticonvulsant, diazepam, which also significantly lowered these discharges ($p < 0.05$, students "t" test). In another experiment (Table 9), orally-administered compound of Example 2 (10.0 μmol/kg) also significantly lowered the incidence of spike wave discharges ($p < 0.05$, students "t" test).

Tables 10 and 11 show experiments in which the nicotinic receptor antagonist mecamylamine is tested for effects on (—)-nicotine or the compound of Example 2 induced attenuation of spike wave discharges. Mecamylamine blocked the effects of both (—)-nicotine and the compound of Example 2 in lowering spike wave discharges. Mecamylamine itself did not affect the incidence of spike/wave discharges. This demonstrates that the effects of (—)-nicotine and the compound of Example 2 on spike wave discharges is due to an interaction with nicotinic acetylcholine receptors.

(—)-Nicotine produces a significant ($p < 0.05$, 2-way ANOVA, Fisher post hoc analysis) attenuation of Fast Fourier Transform calculated low frequency (1–4 Hz) EEG slow-wave patterns (Table 12). In contrast, the compound of Example 2 does not affect those patterns. A known consequence of (—)-nicotine on those slow-wave patterns is a disruption of normal sleep states. The compound of Example 2 would therefore be expected to have fewer sleep-related side effects associated with effects on low frequency slow-wave, such as those associated with (—)-nicotine.

TABLE 8

Attenuation of absence-related spike wave discharges with intraperitoneally administered (-)-nicotine and the compound of Example 2.

| Drug treatment (μmol/kg, i.p.) | Total spike wave duration (seconds) |
|---|---|
| Diazepam | |
| 0 | 47.4 ± 10.1 |
| 3.5 | 4.4 ± 3.2* |
| (-)-Nicotine | |
| 0 | 50.3 ± 12.3 |
| 0.62 | 10.9 ± 4.1* |
| 1.9 | 2.1 ± 1.9* |
| Example 2 | |
| 0 | 66.9 ± 16.5 |
| 1.9 | 26.7 ± 9.2* |
| 6.2 | 33.1 ± 10.2* |

*statistically significant; $p < 0.05$

TABLE 9

Attenuation of absence-related spike wave discharges with orally-administered Example 2 compound

| Drug treatment (μmol/kg. p.o.) | Total spike wave duration (seconds) |
|---|---|
| Example 2 | |
| 0 | 70.8 ± 14.3 |
| 10 | 25.6 ± 7.5* |

*statistically significant; $p < 0.05$

TABLE 10

Mecamylamine blockade of (-)-nicotine induced attenuation of absence-related spike wave discharges.

| Drug treatment (μmol/kg, i.p.) | Total spike wave duration (seconds) |
|---|---|
| Saline (0) | 66.0 ± 13.3 |
| (-)-Nicotine (0.62) | 10.8 ± 4.1* |
| Mecamylamine (5.0) | 45.7 ± 15.0 |
| Mecamylamine (5.0) + (-)-nicotine (0.62) | 85.6 ± 20.2 |

*statistically significant; $p < 0.05$

TABLE 11

Mecamylamine blockade of Example 2 compound-induced attenuation of absence-related spike wave discharges.

| Drug treatment (μmol/kg, i.p.) | Total spike wave duration (seconds) |
|---|---|
| Saline (0) | 31.8 ± 8.0 |
| Example 2 (6.2) | 8.2 ± 3.8* |
| Mecamylamine (5.0) | 46.8 ± 6.4 |
| Mecamylamine (5.0) + | 57.3 ± 16.2 |

TABLE 11-continued

Mecamylamine blockade of Example 2 compound-induced attenuation of absence-related spike wave discharges.

| Drug treatment (μmol/kg, i.p.) | Total spike wave duration (seconds) |
|---|---|
| Example 2 (6.2) | |

*statistically significant; $p < 0.05$

TABLE 12

Effects of (-)-nicotine and Example 2 on 1-4 Hz slow wave EEG.

| Drug treatment (μmol/kg, i.p.) | 1-4 Hz amplitude (μVolts) |
|---|---|
| Saline (0) | 26.0 ± 5.5 |
| (-)-Nicotine (1.9) | 13.2 ± 2.0* |
| Example 2 (1.9) | 27.3 ± 5.0 |

*statistically significant; $p < 0.05$

IN VIVO STUDIES DEMONSTRATING REDUCTION OF THE STATE OF ANXIETY INDUCED BY THE WITHDRAWAL OF CONTINUOUS (−)-NICOTINE TREATMENT

Mouse Elevated Plus-Maze Studies

The mouse elevated plus-maze is a conflict test that probes anxiolytic activity of test compounds (Lister, Psychopharmacology, 1987, 92:180). It is based on the fact that exposure of mice to an elevated open arm leads to an avoidance response considerably stronger than that evoked by exposure to an enclosed arm. Compounds may be tested for their ability to modify the avoidance response of the animal to the open arm maze. Compounds that induce a significant increase in the time spent by the mice in the open arms of the maze may be said to possess anxiolytic activity. The effect of such potential anti-anxiety drugs may be tested further in a withdrawal challenge test. It is known that when mice are dosed with (−)-nicotine in a continuous treatment manner and the treatment is withdrawn a state of anxiety is induced in the mice, and this reaches a maximum 48 hours after discontinuation of the (−)-nicotine treatment. A drug may be tested for its ability to reduce anxiety by administering the drug during the 48-hour anxiety-heightening period following (−)-nicotine withdrawal.

Methods

Elevated Plus-Maze: The procedure originally described by Pellow et al., for rats was used, with minor modifications (Pellow et al., J. Neurosci. Meth., 14: 149, 1985). The apparatus consisted of two open arms (50×10 cm) and two enclosed arms (50×10×40 cm) extending from a central platform (10×10 cm). It was mounted on a base raising 50 cm above the floor. Light levels on the open and enclosed arms were similar. The animals were placed in the center of the maze and the time spent in the open arms and the total distance traveled by the rat were recorded automatically by a camera mounted above the apparatus, then analyzed by computer (Videomex ™ software, Columbus Instruments, Columbus, Ohio). All animals used were naive to the apparatus. Animals were injected i.p. with saline or the different drug doses, and submitted to the test 30 minutes later. The test lasted 5 minutes, and the apparatus was thoroughly cleaned after removal of the animal.

Withdrawal studies: Groups of rats were implanted with Alza minipumps delivering 10 mg/kg/day of (−)-nicotine or saline for 14 days. The pumps were removed on day 14 and the animals were tested in the plus-maze 48 hours later, at the time when a state of withdrawal-induced anxiety was present in the rats. On the test day i.p. doses of either saline or the compound of Example 2 were administered to the animals 30 minutes before the test. Data (Table 13) represent the mean ±SEM time spent in the open arms of the plus-maze of 8-16 rats.

Results

A significant reduction in the time spent in the open arms was observed in animals challenged with saline after chronic treatment with (−)-nicotine in comparison to the animals that were given a chronic saline treatment during the 14 days (Table 13), thus demonstrating the enhanced anxiety upon withdrawal of (−)-nicotine. However, when the compound of Example 2 was given 30 minutes prior to the open arm maze test, a significant increase in the time spent in the open arms was seen at the 0.62 μmol/kg dose, a reversal of the state of anxiety induced by the withdrawal of (−)-nicotine. These data support the utility of the compound of Example 2 in the treatment of nicotine withdrawal.

TABLE 13

Withdrawal-induced anxiety 48 hours after a 14-day chronic treatment with (-)-nicotine is reversed by Example 2

| CHRONIC TREATMENT | CHALLENGE AGENT (μmol/kg) | TIME OPEN ARMS (seconds) |
|---|---|---|
| Saline | Saline | 60.7 ± 9.1 |
| (-)-Nicotine | Saline | 35.1 ± 6.0* |
| | Example 2 (0.19) | 36.8 ± 12.5 |
| | Example 2 (0.62) | 73.6 ± 7.7** |
| | Example 2 (1.9) | 43.1 ± 10.1 |

*$p < 0.05$ against the chronic saline saline-challenged group;
*$p < 0.05$ against the chronic (-)-nicotine saline-challenged group.

The present invention includes one or more of the compounds of formula (I) prepared and formulated with one or more non-toxic pharmaceutically-acceptable compositions, as described below.

Compositions suitable for parenteral injection may comprise pharmaceutically-acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

If desired, and for more effective distribution, the compounds may be incorporated into slow-release or targeted-delivery systems, such as polymer matrices, liposomes, and microspheres. They may be sterilized, for example, by filtration through a bacteria-retaining filter, or by incorporating sterilizing agents in the form of sterile solid compositions, which may be dissolved in sterile water, or some other sterile injectable medium immediately before use.

Solid dosage forms for oral administration may include capsules, tablets, pills, powders, and granules. In such solid dosage forms, the active compound is admixed with at least one inert customary excipient (or carrier), such as sodium citrate or dicalcium phosphate, and additionally (a) fillers or extenders, as for example, starches, lactose, sucrose, glucose, mannitol and silicic acid; (b) binders, as for example, carboxymethylcellulose, alginates, gelatin, polyvinylpyrrolidone, sucrose and acacia; (c) humectants, as for example, glycerol; (d) disintegrating agents, as for example, agar-agar, calcium carbonate, potato or tapioca starch, alginic acid, certain complex silicates and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i)lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

Solid dosage forms such as tablets, dragees, capsules, pills and granules may be prepared with coatings and shells, such as enteric coatings and others well known in this art. They may contain pacifying agents, and may also be of such composition that they release the active compound or compounds in a certain part of the intestinal tract in a delayed manner. Examples of embedding compositions which may be used are polymeric substances and waxes.

The active compounds may also be in micro-encapsulated form, if appropriate, with one or more of the above-mentioned excipients.

Liquid dosage forms for oral administration include pharmaceutically-acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, these liquid dosage forms may also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agaragar and tragacanth, or mixtures of these substances, and the like.

Compositions for rectal or vaginal administrations are preferably suppositories which can be prepared by mixing the compounds of this invention with suitable nonirritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical or transdermal administration of a compound of this invention further include ointments, pastes, creams, lotions, gels, powders, solutions, sprays, inhalants or transdermal patches. Transdermal administration via a transdermal patch is a particularly effective and preferred dosage form of the present invention. The active component is admixed under sterile conditions with a pharmaceutically-acceptable carrier and any needed preservative, buffers or propellants as may be required. It is known that some agents may require special handling in the preparation of transdermal patch formulations. For example, compounds that are volatile in nature may require admixture with special formulating agents or with special packaging materials to assure proper dosage delivery. In addition, compounds which are very rapidly absorbed through the skin may require formulation with absorption-retarding agents or barriers. Ophthalmic formulations, eye ointments, powders and solutions are also contemplated as being within the scope of this invention.

The present compounds may also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically-acceptable and metabolizable lipid capable of forming liposomes may be used. The present compositions in liposome form can contain, in addition to the compounds of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y., (1976), p 33 et seq.

In order to reduce unwanted peripherally-mediated side-effects, it is advantageous, but not essential, to incorporate into the composition a peripherally-acting anti-cholinergic such as N-methylscopolamine, N-methylatropine, propantheline, methantheline, or glycopyrrolate.

Actual dosage levels of active ingredient in the compositions of the invention may be varied in order to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

Total daily dose of the compounds of this invention administered to a host in single or divided doses may be in amounts as determined by the attending physician, typically, for example, of from about 0.001 to 100 mg/kg body weight daily and preferably 0.01 to 10 mg/kg/day. Dosage unit compositions may contain such amounts of submultiples thereof to make up the daily dose. The specific therapeutically-effective treatment regimen for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidentally with the specific compound employed; and like factors well known in the medical arts.

The following examples, which are provided for illustration and not limitation of the invention, will serve to further illustrate preparation of the novel compounds of the invention. Thin-layer chromatography (TLC) was performed on 0.25 mm E. Merck precoated silica gel plates (60 F-254). Flash chromatography was performed on 200-400 mesh silica gel (E. Merck), while column chromatography was performed on 70-230 mesh silica gel (E. Merck).

EXAMPLE 1

3-Methyl-5-(2(S)-pyrrolidinyl)-isoxazole oxalate salt 1 a. N-t-Butyloxycarbonyl-(S)-prolinal N-t-Butyloxycarbonyl-(S)-proline was reduced to N-t-butyloxycarbonyl-(S)-prolinol by treatment with diborane as described by K. E. Rittle, et al., in J. Org. Chem., 1982, 47:3016. N-t-butyloxycarbonyl-(S)-prolinol was then oxidized to N-t-butyloxycarbonyl-(S)-prolinal by treatment with sulfur trioxide-pyridine complex as described by Y. Hamada and T. Shioiri in Chem. Pharm. Bull, 1982, 5:1921. $^1$H NMR spectra were recorded on a 300 MHz spectrometer.

1 b. 2(S)-(2,2-Dibromoethenyl)-N-t-butyloxycarbonyl-pyrrolidine

At room temperature and under nitrogen, triphenylphosphine (13.0 g, 49.54 mmol), zinc dust (2.16 g, 33.0 mmol) and carbon tetrabromide (11.0 g, 33.0 mmol) were added to dicholoromethane (80 mL). After stirring for 5 minutes, a solution of N-t-butyloxycarbonyl-(S)-prolinal 3.29 g, 16.5 mmol)in dicholoromethane (25 ml) was added. The reaction was slightly exothermic. After stirring for 1 hour, the reaction mixture was diluted with a mixture of ethyl acetate/hexane (1:1) and filtered through a basic alumina (0.25 inch thick)/silica (40-60 micron, 0.5 inch thick) cake. The filter cake was then washed with a mixture of dicholoromethane/ethyl acetate/hexane (1:1:1). The filtrate was concentrated in vacuo and the residue was taken up in ethyl acetate/hexane (1:1). The resulting precipitate was filtered off and the filtrate was concentrated. The residual oil was subjected to flash chromatography using ethyl acetate/hexane (1:6.5→1:5) as the eluant. The resultant pure solid product was isolated in 91% yield (5.31 g). TLC $R_f$=0.35 (ethyl acetate/hexane=1.4). $[\alpha]_D^{26°}$=20.1° (c 1.10, MeOH). m.p.=65°-66° C. MS(Cl) m/e 354 (M+H)+. $^1$H NMR (DMSO-d$_6$, 70° C., 300 MHz) δ: 6.57 (d, J=8.1 Hz, 1H), 4.26 (ddd, J=7.9, 7.9, 4.9 Hz, 1H), 3.30 (m, 2H), 2.05-2.17 (m, 1H), 1.72-1.92 (m, 2H), 1.60-1.71 (m, 1H), 1.40 (s, 9H). Anal. calcd. for C$_{11}$H$_{17}$Br$_2$NO$_2$: C, 37.21;H, 4.83; N, 3.95. Found: C, 37.45; H, 4.85; N, 3.97.

1 c. 2(S)-Ethynyl-N-t-butyloxycarbonylpyrrolidine

A solution of Example 1 b (27.1 g, 76.3 mmol) and tetrahydrofuran (THF) (550 mL) was cooled to −75° C. using a dry ice bath. Under a nitrogen atmosphere, a 2.5M solution of n-butyllithium in hexane (62.6 mL, 156.5 mmol) was added dropwise over a 15 minute period. After stirring for 1 hour, saturated aqueous sodium bicarbonate was added dropwise to the reaction flask. The dry ice bath was removed and an additional portion of saturated aqueous sodium bicarbonate was added. The mixture was extracted with ethyl acetate (3X) and the combined organic phases dried over anhydrous sodium sulfate and concentrated in vacuo. The resulting residue was purified by flash chromatography on silica gel eluting with diethyl ether/hexane (1:6 to 1:5) to give 11.5 g (77% yield) of the title compound (1c) as an oil. TLC $R_f$=0.21 (ether:hexane=1.6). $[\alpha]_D^{23°}$=−92.1° (c 2.20, MeOH). MS (Cl) m/e 196 (M+H)+. $^1$H NMR (CDCl$_3$, 300 MHz) 8:4.55-4.36 (m, 1H), 3.53-3.24 (m, 2H), 2.25-1.85 (m, 5H), 1.48 (s, 9H).

1 d. 3-Methyl-5-(N-t-butyloxycarbonyl-2-(S)-pyrrolidinyl)-isoxazole

Under a nitrogen atmosphere, the product of Example 1c (1.45 g, 7.43 mmol) and phenyl isocyanate (1.45 mL, 13.37 mmol) were combined with stirring in 3.5 mL of benzene. A solution of triethylamine (10 drops) and nitroethane (535 μL, 7.43 mmol) in 2 mL of benzene was added to the resultant solution. A precipitate began to form about 2 to 3 minutes after addition was complete. The reaction mixture was stirred at ambient temperature for 2 hours, heated at reflux for 1.5 hours, allowed to cool to ambient temperature and stirred overnight. The reaction mixture was then filtered and the filter cake washed with benzene. The filtrate was concentrated in vacuo and the residue was purified using flash chromatography on silica gel eluting with ethyl acetate/hexane (1:8) to give after concentrating in vacuo, 1.02 g (54.5% yield) of the title compound (1 d) as a viscous yellow oil. $[\alpha]_D^{23°}$=−104.4° (c 0.90, MeOH). MS (DCl/NH$_3$) m/e 253 (M+H)+, 270 (M+NH$_4$)+. $^1$H NMR (DMSO-d$_6$; T=100° C.) δ: 1.32(s, 9H), 1.80-1.90 (m, 3H), 2.16 (s, 3H), 2.14-2.24 (m, 1H), 3.31-3.42 (m, 2H), 4.87 (dd, 1H), 6.04 (s, 1H).

1 e. 3-methyl-5-(2(S)-pyrrolidinyl)-isoxazole

The product of Example 1d (880 mg, 3.49 mmol) was dissolved in anhydrous methylene chloride (7.5 mL) and cooled to 0° C. Excess trifluoroacetic acid (TFA) (7.5 mL) was added and the reaction mixture was stirred for 1 hour at 0° C. The reaction mixture was then concentrated in vacuo until all of the excess TFA was evaporated to afford an amber oil. The oil was dissolved in saturated aqueous sodium bicarbonate solution and continuously extracted with methylene chloride for approximately 16 hours. The solvent was evaporated and the residue was purified by flash chromatography on silica gel eluting with a gradient of 5% methanol in chloroform to 10% methanol in chloroform to give 456 mg (86% yield) of the title compound (1 e). $[\alpha]_D^{23°}$=−13.1° (c 0.9, MeOH). MS (DCl/NH$_3$) m/e 153 (M+H)+. $^1$H NMR (CDCl$_3$) δ: 1.80-2.00 (m, 3H), 1.99 (br s, 1H, NH), 2.14-2.21 (m, 1H), 2.28 (s, 3H), 2.96-3.16 (m, 2H), 4.32 (dd, 1H), 5.95 (s, 1H).

1 f. 3-Methyl-5-(2(S)-pyrrolidinyl)-isoxazole oxalate salt

A solution of the product of Example 1e (20 mg, 0.188 mmol) in diethyl ether was prepared. To this solution a solution of oxalic acid (25 mg, 0.282 mmol) in diethyl ether was added in a dropwise fashion. The resultant white precipitate was filtered and triturated with three portions of diethyl ether. The white solid was recrystallized from methanol/diethyl ether to give, after evaporating the residual solvent in vacuo, 23.7 mg (52% yield) of the title compound, m.p. 133°-135° C. MS (DCl/NH$_3$) m/e 253 (M+H)+, 270 (M+NH$_4$)+. $^1$H NMR (D$_2$O) δ: 2.11-2.33 (m, 3H), 2.31

(s, 3H), 2.49–2.60 (m, 1H), 2.48 (dd, 2H), 4.92 (t, 1H), 6.52 (s, 1H). Anal. calcd. for C$_{10}$H$_{14}$N$_2$O$_5$: C, 49.58; H, 5.82; N, 11.56. Found: C, 49.54; H, 5.80; N, 11.51.

EXAMPLE 2

3-Methyl-5-(1-methyl-2(S)-pyrrolidinyl)-isoxazole oxalate salt 2 a. 3-Methyl-5-(1-methyl-2(S)-pyrrolidinyl)-isoxazole A solution of the product of Example 1e (3-methyl-5-(2(S)-pyrrolidinyl)-isoxazole 93.5 mg, 0.61 mmol), in 1.5 mL of 37% aqueous formaldehyde solution and 1.5 mL of 88% aqueous formic acid solution, was heated at reflux for 1 hour. The reaction mixture was allowed to cool to ambient temperature and was then extracted with diethyl ether. The aqueous layer was made basic (pH ~10 to 11) by sequential addition of saturated aqueous sodium bicarbonate solution and solid potassium carbonate. The basic-aqueous solution was then extracted with three portions of chloroform and combined with the remaining organic phase. The combined organic phases were dried over anhydrous sodium sulfate, filtered and concentrated in vacuo. The residue was subjected to flash chromatography on silica gel eluted with ethyl acetate hexane (1:1) to give 71 mg (70% yield) of the title compound (2a) as a clear colorless oil. $[\alpha]_D^{23°} = -101°$ (c 0.68, MeOH). MS (FAB) m/e 167 (M+H)$^+$. $^1$H NMR (CDCl$_3$) δ: 1.78–2.03 (m, 3H), 2.17–2.42 (m, 2H), 2.29 (s, 3H), 2.34 (s, 3H), 3.13–3.20 (m, 1H), 3.43 (dd, 1H), 5.99 (s, 1H).

2 b. 3-Methyl-5-(1-methyl-2(S)-pyrrolidinyl)-isoxazole oxalate salt

A solution of oxalic acid (51 mg, 0.57 mmol) in diethyl ether was added dropwise to a stirring solution of 3-methyl-5-(1-methyl-2-pyrrolidinyl)-isoxazole (62.8 mg, 0.38 mmol), from Example 2a, in diethyl ether. After 0.5 hour of stirring at ambient temperature, the reaction flask became coated with a glass-like clear colorless solid. The diethyl ether was evaporated and the solid was triturated several times with diethyl ether to give, after evaporation of the solvent in vacuo, 102 mg of the title compound (2b). MS (DCl/NH$_3$) m/e 167 (M+H)$^+$, 184 (M+NH$_4$)$^+$. $^1$H NMR (D$_2$O) δ: 2.11–2.33 (m, 3H), 2.31 (s, 3H), 2.49–2.60 (m, 1H), 2.48 (dd, 2H), 4.92 (t, 1H), 6.52 (s, 1H). Anal. calcd. for C$_{10}$H$_{13}$NO$_5$.0.2H$_2$O.0.2C$_2$H$_2$O$_2$: C, 48.65; H, 6.16; N, 9.95. Found: C, 48.80; H, 5.90; N, 9.77.

EXAMPLE 3

3-Ethyl-5-(2(S)-pyrrolidinyl)-isoxazole oxalate salt 3 a. 3-Ethyl-5-(N-t-butyloxycarbony-2(S)-pyrrolidinyl)-isoxazole Under a nitrogen atmosphere, (2S)-2-Ethynyl-N-t-butoxycarbonylpyrrolidine (885 mg, 4.52 mmol) and phenyl isocyanate (887 μL, 8.16 mmol) were combined, in 2.2 mL of benzene. The solution was stirred throughout the addition of the ingredients. A solution of nitropropane (404 μL, 4.53 mmol) in 1.2 mL of benzene and 7 drops of triethylamine was then added to the above solution. A precipitate began to form about 2 to 3 minutes after addition was complete. The reaction mixture was stirred at ambient temperature for 2 hours, heated at reflux for 1.5 hours, allowed to cool to ambient temperature and stirred overnight. The reaction mixture was then filtered and the filter cake washed with benzene. The filtrate was concentrated in vacuo and the residue was purified using flash chromatography on silica gel eluting with ethyl acetate/hexane (1:8) to give, after evaporation of the solvent in vacuo, 631.6 mg (52% yield) of the title compound (3a). MS (DCl/NH$_3$) m/e 267 (M+H)$^+$, 284 (M+NH$_4$)$^+$. $^1$H NMR (DMSO-d6: T=100° C.) δ: 1.19 (t, J=7.5 Hz, 1.34 (s, 9H), 1.89–1.95 (m, 3H), 2.2–2.3 (m, 1H), 2.60 (q, J=7.5 Hz, 2H), 3.39–3.45 (m, 2H), 4.91 (dd, J=7.5 Hz, 2.5 Hz, 1H), 6.10 (s, 1H).

3 b. 3-Ethyl-5-(2(S)-pyrrolidinyl)-isoxazole

The product of Example 3a (610 mg, 2.29 mmol) was dissolved in methylene chloride (7.5 ml) and cooled to 0° C. The solution was then treated with TFA, saturated sodium bicarbonate solution, and methylene chloride in the same manner as described in Example 1 e above. The crude product was purified by flash chromatography on silica gel eluting with 5% methanol in chloroform to give 245 mg (64% yield) of the title compound (3b) as a light amber-colored oil. MS (DCl/NH$_3$) m/e 167 (M+H)$^+$, 184 (M+NH$_4$)$^+$. $^1$H NMR (CDCl$_3$) δ: 1.25 (t, 3H), 1.80–1.95 (m, 3H) 2.07 (br s, 1H, NH), 2.11–2.24 (m, 1H), 2.66 (q, 9H), 2.97–3.16 (m, 2H), 4.32 (dd, 1H), 5.99 (s, H).

3 c. 3-Ethyl-5-(2(S)-pyrrolidinyl)-isoxazole oxalate salt

A solution of the product of Example 3b (51.2 mg, 0.35 mmol) in diethyl ether was cooled to 0° C. A solution of oxalic acid (2 equivalents) in diethyl ether was added dropwise with vigorous stirring. The reaction mixture was stirred for 1 hour at 0° C. and the solvent was evaporated in vacuo. The solid was recrystallized from methanol/diethyl ether to give, after evaporation of the solvent in vacuo, 68.1 mg (86.3% yield) of the title compound (3c) as white needle-like crystals, m.p. 131°–133° C. MS (DCl/NH$_3$) m/e 167 (M+H)$^+$, 184 (M+NH$_4$)$^+$. $^1$H NMR (CD$_3$OD) δ: 1.27 (t, J=7.5 Hz, 3H), 2.17–2.31 (m, 3H), 2.48–2.53 (m, 1H), 2.73 (q, J=7.5 Hz, 2H), 3.42–3.47 (m, 2H), 4.91 (buried in H$_2$O peak, 1H), 6.56 (s, 1H). Anal. calcd. for C$_{11}$H$_{16}$N$_2$O$_5$: C, 51.56; H, 6.29; N, 10.93. Found: C, 51.61; H, 6.29; N, 10.97.

EXAMPLE 4

3-Ethyl-5-(1-methyl-2(S)-pyrrolidinyl)-isoxazole oxalate salt 4 a. 3-Ethyl-5-(1-methyl-2(S)-pyrrolidinyl)-isoxazole The product of Example 3c (150 mg, 0.90 mmol) was treated with excess formaldehyde and excess formic acid as described above in Example 2a. Subsequent steps followed in Example 2a were also followed except the flash chromatography on silica gel was eluted with 2% methanol in chloroform to give 154.5 mg (95% yield) of the title compound (4a) as a clear colorless oil. $^1$H NMR (CDCl$_3$) δ: 1.26 (t, 3H), 1.81–2.02 (m, 3H), 2.17–2.29 (m, 1H), 2.34 (s, 3H), 2.67 (q, 2H), 3.13–3.21 (m, 2H), 3.43 (dd, 1H), 6.03 (s, 1H).

4 b. 3-Ethyl-5-(1-methyl-2(S)-pyrrolidinyl)-isoxazole oxalate salt

Using the procedure described in Example 2b, the product of Example 4a (135 mg, 0.75 mmol) was converted to the oxalate salt in quantitative yield to give 204.6 mg of the title compound. MS (DCl/NH$_3$) m/e 181 (M+H)$^+$, 198 (M+NH$_4$)$^+$. $^1$H NMR (CD$_3$OD) δ: 1.28 (t, J=7.7 Hz, 3H), 2.21–2.33 (m, 2H), 2.35–2.50 (m, 1H), 2.52–2.63 (m, 1H), 2.72 (q, J=7.7 Hz, 2H), 2.90 (s, 3H), 3.35–3.42 (m, 1H), 3.70–3.80 (m, 1H, 4.77 (dd, 1H), 6.68 (s, 1H). Anal. calcd. for C$_{11}$H$_{16}$N$_2$O$_5$.0.5H$_2$O: C, 51.51; H, 6.86; N, 10.03. Found: C, 51.62; H, 6.48; N, 9.83.

EXAMPLE 5

3-methyl-5-(2(S)-pyrrolidinyl)-isothiazole hydrochloride 5 a. 2(S)-(3-hydroxy-1-butynyl)-N-t-butyloxycarbonyl pyrrolidine Under a nitrogen atmosphere, 2.0g (5.63 mmol) of (2S)-2-(2,2-dibromoethenyl)-N-t-butyloxycarbonylpyrrolidine (Example 1b) was added to 10 ml of THF. The solution was cooled to −75° C. and n-butyllithium (4.6 mL, 11.54 mmol of a 2.5 M solution in hexane) was added dropwise over a period of 10 minutes. This solution was stirred for 20 minutes before adding acetaldehyde (377 μL, 6.75 mmol). This mixture was allowed to warm slowly to ambient temperature over several hours. The reaction was then quenched by adding aqueous-saturated sodium bicarbonate solution. The aqueous mixture was extracted with two portions of ethyl acetate and the organic phase was dried over anhydrous sodium sulfate and concentrated in vacuo to an orange oil. The oil was purified by column chromatography on silica gel eluting with ethyl acetate/hexane (1:2) to give 1.27 g (91% yield) of the title compound (5a) as a colorless oil. MS (DCl/NH$_3$) m/e 240 (M+H)$^+$. $^1$H NMR (CDCl$_3$ 300 MHz) δ: 1.43 (d, J=6.6 Hz, 3H), 1.48 (s, 9H), 1.4–2.1 (m, 4H), 3.2–3.5 (m, 3H), 4.45 (br s, 1H), 4.53 (q, J=6.6 Hz, 1H).

5 b. 2(S)-(3-keto-1-butynyl)-N-t-butyloxycarbonyl pyrrolidine

At −60° C. and under a nitrogen atmosphere, dimethylsulfoxide (1.12 mL, 15.8 mmol) was added to a solution of oxalyl chloride (1.28 mL, 14.7 mmol) in methylene chloride (30 mL). The reaction mixture was stirred for 10 minutes at −60° C., then a solution of the product of Example 5a (1.26 g, 5.26 mmol) in methylene chloride (5 mL) was slowly added (over a two minute period). This mixture was stirred for 15 minutes at −60° C. before diisopropylethylamine (5.5 mL, 31.6 mmol) was added. After an additional 10 minutes of stirring at −60° C., the reaction mixture was warmed to 0° C. and quenched with aqueous saturated ammonium chloride. The aqueous phase was extracted with methylene chloride and the organic extract was combined with organic phase from the original reaction mixture. The combined organic phases were then dried over anhydrous sodium sulfate and concentrated in vacuo. The residue was purified by column chromatography on silica gel eluting with ethyl acetate/hexane (1:1) to give 824 mg (66% yield) of the title compound (5b) as a colorless oil, $[\alpha]_D^{22°}$=−142.3° (c 1.4, CH$_2$Cl$_2$). MS (DCl/NH$_3$) m/e 238 (M+H)$^+$. $^1$H NMR (DMSO-d6, 300 MHz) δ: 1.3–1.5 (m, 9H), 1.8–2.2 (m, 2.5H), 2.30 (s, 2.5H), 3.2–3.4 (m, 4H), 4.60 (br s, 1H).

5 c. 3-methyl-5-(N-t-butyloxycarbonyl-2(S)-pyrrolidinyl)-isothiazole

The title compound was prepared using a modification of the procedure described by Lucchesini, et al., in Heterocycles, 1989, 29:97–102. A solution of (2S)-2-(3-keto-1-butynyl)-N-t-butyloxycarbonyl pyrrolidine (704 mg, 3 mmol), from Example 5b, in 50% aqueous methanol (8 mL) was cooled to 0° C. Hydroxylamino-sulfonic acid (338 mg, 3 mmol) was added to the solution and the reaction mixture was stirred for 45 minutes. After the 45 minutes of mixing, solid sodium bicarbonate (250 mg, 3 mmol) was added to the reaction mixture, followed by the addition of 2.3 mL of a 1.4 M aqueous solution of sodium hydrosulfide (3.3 mmol). The reaction mixture was then stirred at ambient temperature for 6.5 hours. The reaction mixture was diluted with brine and extracted with two portions of ethyl acetate. The aqueous phase was made basic by the addition of excess sodium bicarbonate. Additional sodium hydrosulfide (800 μL of 1.4M solution) was added and the reaction mixture was stirred overnight. The aqueous phase was again extracted with ethyl acetate and the organic extract was combined with the organic extracts from the previous day. The combined organic phases were dried over anhydrous sodium sulfate and concentrated in vacuo. The residue was purified by column chromatography on silica gel eluting with ethyl acetate/hexane (1:1) to yield 135 mg (17% yield) of the title compound (5c) as a yellow oil, $[\alpha]_D^{23°}$=−90.9° (c 1.28, CH$_2$Cl$_2$). MS (DCl/NH$_3$) m/e 269 (M+H)$^+$. $^1$H NMR (DMSO-d6, 300 MHz) δ: 1.36 (s, 9H), 1.83–1.98 (m, 3H), 2.31 (s, 1H), 2.37 (s, 3H), 3.40 (dd, J=7.5, 6.1 Hz, 2H), 5.14 (dd, J=9.8, 2.4 Hz, 1H), 6.96 (s, 1H).

5 d. 3-methyl-5-(2(S)-pyrrollidinyl)-isothiazole hydrochloride 2 mL of a saturated solution of hydrogen chloride in dioxane was added to the product of Example 5c (115 mg, 0.43 mmol). The reaction mixture was left at ambient temperature for 30 minutes before it was concentrated in vacuo. The residue was dissolved in methylene chloride and washed with saturated aqueous sodium bicarbonate. The organic phase was dried over anhydrous sodium sulfate and concentrated in vacuo to afford 40 mg of a yellow oil. A sample of this oil (9.5 mg) was purified by column chromatography on silica gel eluting with 10% ethanol in ethyl acetate to afford 9 mg of a colorless oil. This material (the free amine) was dissolved in ethanol (1 drop) and diethyl ether (~1.5 mL). A saturated solution of hydrogen chloride in diethyl ether was then added to this solution. A precipitate formed and was collected by centrifugation. The collected precipitate was washed with diethyl ether and dried in vacuo to yield the title compound (5d/5) as a white powder, m.p. 129°–130° C. MS (DCl/NH$_3$) m/e 169 (M+H)$^+$. $^1$H NMR (D$_2$O, 300 MHz) δ: 2.15–2.37 (m, 3H), 2.49 (s, 3H), 2.65 (m, 1H), 3.47–3.56 (m, 2H), 5.07 (dd, J=8.5, 6.6 Hz, 1H), 7.31 (s, H).

EXAMPLE 6

3-methyl-5-(1-methyl-2(S)-pyrrolidinyl)-isothiazole hydrochloride

The product of Example 5, 3-methyl-5-(2(S)-pyrrolidinyl)-isothiazole, (30 mg) was treated in the same manner as described in Example 2a, with the exception that the crude product was purified by column chromatography on silica gel and eluted with 10% ethanol in ethyl acetate to afford 9.8 mg of a colorless oil. This material was then dissolved in diethyl ether (~5 mL). Diethyl ether saturated with hydrogen chloride was then added dropwise with mixing. The precipitate which formed was collected by centrifugation, washed with diethyl ether and dried to yield the title compound as a white powder, m.p. 133°–134° C. MS (DCl/NH$_3$) m/e 183 (M+H)$^+$, 270 (M+NH$_4$)$^+$. $^1$H NMR (D$_2$O, 300 MHz) δ: 2.21–2.39 (m, 3H), 2.51 (s, 3H), 2.72 (m, 1H), 2.84 (br, s, 3H), 3.35 (m, 1H), 3,.78 (m, 1H), 4.79 (m, 1H), 7.39 (s, 1H).

EXAMPLE 7

3-Benzyl-5-(1-methyl-2(S)-pyrrolidinyl)-isoxazole oxalate salt 7 a. 3-Benzyl-5-(N-t-butyloxycarbonyl-2(S)-pyrrolidinyl)-isoxazole The nitrile oxide was generated from 2-phenyl-1-nitroethane which was prepared via the reduction of nitrostyrene as described by A. K. Sinhababu in Tet. Let., 1983, 24, 227–30. Nitrostyrene was prepared using the method described by D. E. Worrall in Org. Syn., 1,413–14.

Under a nitrogen atmosphere, (2S)-Ethynyl-N-t-butyloxycarbonylpyrrolidine (617 mg, 3.16 mmol) and phenyl isocyanate (1.25 mL, 11.38 mmol) were combined in 1.6 mL of benzene. A solution of 2-phenyl-1-nitroethane (955 mg, 6.32) in 1.8 mL of benzene and 5 drops of triethylamine was then added to the above solution. A precipitate began to form about 2 to 3 minutes after addition was complete. The reaction mixture was stirred at ambient temperature for 2 hours, heated at reflux for 1.5 hours, allowed to cool to ambient temperature and stirred overnight. The reaction mixture was then filtered and the filter cake washed with benzene. The filtrate was concentrated in vacuo, and the crude product was purified by flash chromatography on silica gel eluted with ethyl acetate/hexane (1:10) to give 614 mg (59% yield) of the title compound (7a) as a viscous yellow oil. MS (DCl/NH$_3$) m/e 329 (M+H)$^+$, 346 (M+NH$_4$)$^+$. $^1$H NMR (DMSO-d$_6$, 300 MHz, 100° C.) δ: 1.27 (s, 9H), 1.84–1.97 (m, 3H), 2.19–2.29 (m, 1H), 3.33–3.46 (m, 2H), 3.95 (s, 2H), 4.90 (dd, J=7.8 Hz, 2.7 Hz, 1H), 6.02 (s, 1H), 7.20–7.34 (m, 5H).

7 b. 3-Benzyl-5-(2(S)-pyrrolidinyl)-isoxazole

The product of Example 7a (600 mg, 1.83 mmol) was treated in the same manner as set forth in Example 1 e. However, the purification was accomplished using flash chromatography on silica gel eluted with 1% methanol in chloroform to give 263 mg (63% yield) of the title compound (7b) as a pale yellow oil. MS (DCl/NH3) m/e 229 (M+H)$^+$, 246 (M+NH$_4$)$^+$. $^1$H NMR (CDCl$_3$/D$_2$O exchange, 300 MHz) δ: 1.88–1.92 (m, 3H), 2.09–2.23 (m, 1H), 2.93–3.10 (m, 2H), 3.97 (s, 2H), 4.27 (dd, J=7.5 Hz, 5.3 Hz, 1H), 5.88 (s, 1H), 7.21–7.37 (m, 5H).

7 c. 3-Benzyl-5-(1-methyl-2(S)-pyrrolidinyl)-isoxazole

The product from Example 7b (191.0 mg, 0.84 mmol) was treated in the same manner as set forth in Example 2a. However, purification was accomplished using flash chromatography on silica gel eluted with ethyl acetate/hexane (1:2) to give 152.5 mg (75% yield) of the title compound (7c) as a clear colorless oil. MS (DCl/NH$_3$) m/e 243 (M+H)$^+$, 260 (M+NH$_4$). $^1$H NMR (CDCl$_3$, 300 MHz) δ: 1.79–2.00 (m, 3H), 2.14–2.25 (m, 1H), 2.29–2.38 (m, 1H), 2.30 (s, 3H), 3.11–3.18 (m, 1H), 3.37–3.43 (m, 1H), 3.99 (s, 2H), 5.92 (s, 1H), 7.21–7.36 (m, 5H).

7 d. 3-Benzyl-5-(1-methyl-2(S)-pyrrolidinyl)-isoxazole oxalate salt

The product from Example 7c (147 mg, 0.61 mmol) was dissolved in diethyl ether. While stirring, a solution of oxalic acid (2 equivalents) in diethyl ether was introduced dropwise into the reaction vessel. The solvent was evaporated leaving a clear viscous oil. The product was triturated several times with diethyl ether and then the solvents evaporated in vacuo to give 147 mg (73% yield) of the title compound (7d/7) as a clear oil. MS (DCl/NH$_3$) m/e 243 (M+H)$^+$, 260 (M+NH$_4$)$^+$. $^1$H NMR (CD$_3$OD, 300 MHz) δ: 2.19–2.45 (m, 3H), 2.50–2.62 (m, 1H), 2.88 (s, 3H), 3.40–3.50 (partly buried in MeOH peak, 1H), 3.67–3.77 (m, 1H), 4.04 (s, 2H), 4.73 (br dd, J=8.9 Hz, 8.4 Hz, 1H), 6.58 (s, 1H), 7.21–7.35 (m, 5H). Anal. calc. for C$_{17}$H$_{20}$N$_2$O$_5$.0.4 C$_2$H$_2$O$_2$: C, 58.04; N, 5.69; H, 7.60. Found: C, 58.41; H, 5.75; N, 7.69.

EXAMPLE 8

3-Benzyl-5-(1-methyl-2(S)-pyrrolidinyl)-isoxazole hydrochloride salt

A solution of the product from Example 7b (97.0 mg, 0.40 mmol) in diethyl ether was cooled to 0° C. While the above solution was stirring, a solution of diethyl ether saturated with anhydrous HCl gas was added to it dropwise. The solvent was evaporated in vacuo and the residue was triturated with diethyl ether. The solvent was then dried in vacuo to give the title compound (8) as a clear colorless viscous oil in quantitative yield. [α]$^{23}$$_D$=−22.3° (c 0.26, MeOH). MS (DCl/NH$_3$) m/e 243 (M+H)$^+$. $^1$H NMR (CD$_3$OD, 300 MHz) δ: 2.21–2.44 (m, 3H), 2.52–2.63 (m, 1H), 2.91 (br s, 3H), 3.30–3.42 (partly buried in MeOH peak, 1H), 3.76–3.80 (m, 1H), 4.05 (s, 2H), 4.70–4.82 (m, 1H), 6.60 (s, 1H), 7.21–7.32 (m, 5H). Anal. calcd. for C$_{15}$H$_{19}$ClN$_2$O.0.8 H$_2$O: C, 61.45; H, 7.08; N, 9.55. Found: C, 61.42; H, 7.00; N, 9.30.

EXAMPLE 9

5-(1-Methyl-2(S)-pyrrolidinyl-3-pyrrolidinyl)-3-propyl-isoxazole hydrochloride salt 9 a. 5-(N-t-butyloxycarbonyl-2(S)-pyrrolidinyl)-3-propyl-isoxazole Under a nitrogen atmosphere with stirring, (2S)-Ethynyl-N-t-butyloxycarbonylpyrrolidine (1.23 g, 6.30 mmol) and phenyl isocyanate (1.55 mL, 14.2 mmol) were combined in 2.6 mL of benzene. A solution of nitrobutane (1.0 mL, 9.45 mmol) in 3.0 mL of benzene and 7 drops of triethylamine was then added to the solution. A precipitate began to form about 2 to 3 minutes after addition was complete. The reaction mixture was stirred at ambient temperature for 2 hours, heated at reflux for 1.5 hours, allowed to cool to ambient temperature and stirred overnight. The reaction mixture was then filtered and the filter cake washed with benzene. The filtrate was concentrated in vacuo and the residue was purified using flash chromatography on silica gel eluted with ethyl acetate/hexane (1:12→1:10→1:8) to give 1.07 g (61% yield) of the title compound (9a) as a clear yellow oil. [α]$^{23}$$_D$=−51.4° (c 0.80, MeOH). MS (DCl/NH$_3$) m/e 281 (M+H)$^+$, 298 (M+NH$_4$)$^+$. $^1$H NMR (DMSO-d$_6$, 500 MHz, 100° C.) δ0.93 (t, J=7.5 Hz, 3H), 1.34 (s, 9H), 1.64 (qt, J=7.5 Hz, 7.3 Hz, 2H), 1.88–1.95 (m, 3H), 2.22–2.27 (m, 1H), 2.56 (t, J=7.3 Hz, 2H), 3.37–3.46 (m, 2H), 4.92 (dd, J=8.3 Hz, 2.6 Hz, 1H), 6.08 (s, 1H).

9 b. 5-(2(S)-pyrrolidinyl)-3-propyl-isoxazole

The product of Example 9a (987 mg, 3.52 mmol) was treated in the same manner as set forth in Example 1 e. However, the residue was purified using flash chromatography on silica gel eluted with 2%→5%→10% methanol in chloroform to give 585 mg (92% yield) of the title compound (9b) an amber oil. [α]$^{23}$$_D$632 631 11.5° (c 1.2, MeOH). MS (DCl/NH$_3$) m/e 181 (M+H)$^+$, 198 (M+NH$_4$)$^+$. $^1$H NMR (CDCl$_3$, 300 MHz) δ: 0.97 (t, J=7.4 Hz, 3H), 1.68 (tq, J=7.5 Hz, 7.4

Hz, 2H), 1.80–1.97 (m, 3H), 2.06 (br s, NH), 2.12–2.25 (m, 1H), 2.61 (t, J=7.5 Hz, 2H), 2.98–3.16 (m, 2H), 4.32 (dd, J=7.7 Hz, 5.5 Hz, 1H), 5.97 (s, 1H).

9 c. 5-(1-Methyl-2(S)-pyrrolidinyl)-3-propyl-isoxazole

The product of Example 9b (370 mg, 2.05 mmol) was treated in the same manner set forth in Example 2a. However the residue was purified using flash chromatography on silica gel eluted with ethyl acetate/hexane (1:2→1:1) to give 297 mg (74% yield) of the title compound (9c) as a clear yellow oil. $[\alpha]^{23}{}_D 632 -84.1°$ (c 1.2, MeOH). MS (DCl/NH$_3$) m/e 195 (M+H)$^+$, 212 (M+NH$_4$)$^+$. $^1$H NMR (CDCl$_3$, 300 MHz) δ: 0.98 (t, J=7.4 Hz, 3H), 1.69 (tq, J=7.7 Hz, 7.4 Hz, 2H), 1.80–2.20 (m, 3H), 2.18–2.30 (m, 1H), 2.32–2.41 (m, 1H), 2,34 (br s, 3H), 2.62 (t, J=7.7 Hz, 2H), 3.13–3.21 (m, 1H), 3.43 (dd, J=8.1 Hz, 7.4 Hz, 1H), 6.01 (s, 1H).

9 d. 5-(1-Methyl-2(S)-pyrrolidinyl)-3-propyl-isoxazole hyrochloride salt

A solution of the product from Example 9c (250 mg, 1.29 mmol) in diethyl ether was cooled to 0° C. Diethyl ether, saturated with anhydrous HCl gas was then added dropwise to the reaction vessel. The solvent was evaporated and the remaining white solid was redissolved in MeOH/diethyl ether. The solvent was evaporated to give 268 mg (90% yield) of the title compound (9d) as hygroscopic short white needles, m.p.=112°–114° C. $[\alpha]^{23}{}_D = -27.2°$ (c 0.66, MeOH). MS (DCl/NH$_3$) m/e 195 (M+H)$^+$. $^1$H NMR (D$_2$O, 300 MHz) δ: 0.92 (t, J=7.4 Hz, 3H), 1.70 (tq, J=7.4 Hz, 7.4 Hz, 2H), 2.22–2.48 (m, 3H), 2.57–2.66 (m, 1H), 2.70 (t, 7.4 Hz, 2H), 2.93 (br s, 3H), 3.37–3.47 (m, 1H), 3.72–3.84 (m, 1H), 4.77–4.87 (partly buried in H20 peak, 1H), 6.70 (s, 1H). Anal. calcd. for C$_{11}$H$_{19}$ClN$_2$O: C, 57.26; H, 8.30; N, 12.14. Found: C, 57.18; H, 8.23; N, 11.98.

EXAMPLE 10

3-n-Butyl-5-(1-methyl-2(S)-pyrrolidinyl)-isoxazole hydrochloride salt 10 a. 3-n-Butyl-5-(N-t-butyloxycarbonyl-2(S)-pyrrolidinyl)-isoxazole Under a nitrogen atmosphere a solution containing the product of Example 1 c (620 mg, 3.18 mmol) and phenyl isocyanate (1.3 mL, 11.4 mmol) in 1.6 mL of benzene was prepared. A second solution containing nitropentane (782 μL, 6.36 mmol) in 1.7 mL of benzene and 5 drops of triethylamine was then added to the first solution. A precipitate began to form about 2 to 3 minutes after addition was complete. The reaction mixture was stirred at ambient temperature for 2 hours, heated at reflux for 1.5 hours, allowed to cool to ambient temperature and stirred overnight. The reaction mixture was then filtered and the filter cake washed with benzene. The filtrate was concentrated in vacuo and the residue was purified using flash chromatography on silica gel eluted with ethyl acetate/hexane (1:15→1:12→1:10→1:8) to give 567 mg (61% yield) of the title compound (10a) as a clear yellow oil. $[\alpha]^{23}{}_D = -90.0°$ (c 0.60, MeOH). MS (DCl/NH$_3$) m/e 295 (M+H)$^+$, 312 (M+NH$_4$)$^+$. $^1$H NMR (DMSO-d$_6$, 500 MHz, 100° C.) δ: 0.90 (t, J=7.7 Hz, 3H), 1.12–1.40 (m, 2H), 1.34 (s, 9H), 1.60 (tt, J=7.4 Hz, 2H), 1.87–1.96 (m, 3H), 2.21–2.29 (m, 1H), 2.58 (t, J=7.4 Hz, 2H), 3.37–3.47 (m, 2H), 4.91 (dd, J=7.8, 2.9 Hz, 1H), 6.08 (s, 1H).

10 b. 3-n-Butyl-5-(2(S)-pyrrolidinyl)-isoxazole

The product from Example 10a (540 mg, 1.83 mmol) in methylene chloride was treated in the manner set forth in Example 1 e. However, the purification using flash chromatography was done with silica gel eluted with 2%→5% methanol in chloroform to give 301 mg (85% yield) of the title compound (10b) as a clear yellow oil. MS (DCl/NH$_3$) m/e 195 (M+H)$^+$, 212 (M+NH$_4$)$^+$. $^1$H NMR (CDCl$_3$, 300 MHz) δ: 0.93 (t, J=7.4 Hz, 3H), 1.32–1.44 (m, 2H), 1.58–1.68 (m, 2H), 1.80–1.97 (m, 3H), 2.13–2.23 (m, 1H), 2.63 (t, J=7.5 Hz, 2H), 2.97–3.15 (m, 2H), 4.31 (dd, J=7.4 Hz, 5.5 Hz, 1H), 5.97 (s, 1H).

10 c. 3-n-Butyl-5-(1-methyl-2(S)-pyrrolidinyl)-isoxazole

The product from Example 10b (219 mg, 1.13 mmol) was treated in the same manner as set forth in Example 2a. However, the purification using flash chromatography was done with silica gel eluted with 0.5%→1% methanol in chloroform to give 149 mg (63 %yield) of the title compound (10c) as a clear oil. $[\alpha]^{23}{}_D = -54.4°$ (c 0.59, MeOH), MS (DCl/NH$_3$) m/e 209 (M+H)$^+$. $^1$H NMR (CDCl$_3$, 300 MHz) δ: 0.93 (t, J=7.4 Hz, 3H), 1.38 (br tq, J=7.7 Hz, 7.0 Hz, 2H), 1.59–1.69 (m, 3H), 1.80–2.02 (m, 2H), 2.17–2.29 (m, 1H), 2.32–2.40 (m, 1H), 2.34 (s, 3H), 2.65 (t, J=7.7 Hz, 2H), 3.14–3.20 (m, 1H), 3.42 (br dd, J=7.0 Hz, 7.0 Hz, 1H), 6.00 (s, 1H).

10 d. 3-n-Butyl-5-(1-methyl-2(S)-pyrrolidinyl)-isoxazole hydrochloride salt

The product from Example 10c (99 mg, 0.48 mmol) was dissolved in diethyl ether, and cooled to 0° C. An ethereal solution of HCl was then added to the solution dropwise. The solvent was evaporated in vacuo and the remaining white solid was triturated (3X) with diethyl ether. The solvent was then evaporated in vacuo to give 72 mg (61% yield) of the title compound (10) as a hygroscopic white solid, m.p.=100°–102° C. $[\alpha]^{23}{}_D = -25.2°$ (c 0.40, MeOH). MS (DCl/NH$_3$) m/e 209 (M+H)&$^+$. $^1$H NMR (D$_2$O, 300 MHz) δ: 0.91 (t, J=7.4 Hz, 3H), 1.33 (br tq, J=7.7 Hz, 7.4 Hz, 2H), 1.66 (br tt, J=7.7 Hz, 7.4 Hz, 2H), 2.22–2.48 (m, 3H), 2.56–2.69 (m, 1H), 2.74 (t, J=7.7 Hz, 2H), 2.91 (br s, 3H), 3.33–3.43 (m, 1H), 3.72–3.80 (m, 1H), 4.74–4.82 (partly buried in H$_2$O peak, 1H), 6.69 (s, 1H). Anal. calcd. for C$_{12}$H$_{21}$ClN$_2$O.0.4 H$_2$O: C, 57.20; H, 8.72; N, 11.12. Found: C, 57.57; H, 8.43; N, 10.83.

EXAMPLE 11

3-Methyl-5-(1-methyl-2(S)-pyrrolidinyl)-isoxazole hydrochloride salt 11 a. 3-Methyl-5-(1-methyl-2(S)-pyrrolidinyl)-isoxazole hydrochloride salt The product of example 2a (1.04g, 6.26 mmol) was dissolved in diethyl ether (100 mL) and cooled to 0° C. While the reaction was being stirred, an ethereal solution of HCl was added to the reaction causing a white precipitate to form. The solvent was evaporated in vacuo and the remaining solid was dissolved in MeOH-/Et$_2$O and recrystallized to give 543 mg (86% yield) of the title compound (11) as hygroscopic white needles. m.p.=155°–157° C. $[\alpha]^{23}{}_D = -32.4°$ (c 0.58, MeOH). MS (DCl/NH$_3$) m/e 167 (M+H)$^+$, 184 (M+NH$_4$). $^1$H NMR (D$_2$O, 300 MHz) δ: 2.23–22.48 (m, 3H), 2.34 (s, 3H), 2.55–2.68 (m, 1H), 2.92 (br s, 3H), 3.33–3.45 (m, 1H), 3.72–3.82 (m, 1H), 4.74–4.84 (partly buried in H$_2$O peak, 1H), 6.65 (s, 1H). Anal. calcd. for C$_9$H$_{15}$ClN$_2$O: C, 53.33; H, 7.46; N, 13.82. Found: C, 53.52; H,7.49; N, 13.62.

EXAMPLE 12

3-Ethyl-5-(1-methyl-2(S)-pyrrolidinyl)-isoxazole hydrochloride salt 12 a. 3-Ethyl-5-(1-methyl-2(S)-pyrrolidinyl)-isoxazole hydrochloride salt Using the procedure from Example 11, the product of Example 4a (75mg, 0.42 mmol) was converted to the hydrochloride salt. The resultant white precipitate was triturated (4X) with diethyl ether and then the solvent evaporated in vacuo to give 72 mg (80% yield) of a hygroscopic white solid. m.p.=13520 -136° C. $[\alpha]^{23}_D = -28.6°$ (c 0.42, MeOH). MS (DCl/NH$_3$) m/e 181 (M+H)+, 198 (M+NH$_4$)+. $^1$H NMR (DMSO-d$_6$, 500 MHz, 30° C.) δ: 1.21 (t, J=7.8 Hz, 3H), 2.05–2.28 (m, 4H), 2.67 (q, J=7.8 Hz, 2H), 2.81 (br s, 3H), 3.15–3.25 (m, 1H), 3.63–3.71 (m, 1H), 4.69–4.76 (m, 1H), 6.85 (br s, 1H). Anal. calcd. for C$_{10}$H$_{17}$ClN$_2$O: C, 55.42; H, 7.91; N, 12.93. Found: C, 55.15; H, 7.68; N, 12.73.

EXAMPLE 13

5(1-Ethyl-2(S)-pyrrolidinyl)-3-methyl-isoxazole hydrochloride salt 13 a. 5-(1-Acetyl-2(S)-pyrrolidinyl)-3-methyl-isoxazole 3-Methyl-5-(2(S)-pyrrolidinyl)-isoxazole (90 mg, 0.59 mmol) and acetic anhydride (120 mg, 1.2 mmol) were combined in 1,4-dioxane (1.5 mL) and refluxed with stirring for one hour. The reaction was allowed to cool to ambient temperature and the solvent was evaporated in vacuo. The crude product was subjected to flash chromatography on silica gel eluted with 2% methanol in chloroform to give 117 mg (quantitative yield) of the title compound (13a) as a clear yellow oil. MS (DCl/NH$_3$) m/e 195 (M+H)+, 212 (M+NH$_4$)+. $^1$H NM (CDCl$_3$, 300 MHz) δ: 1.86–2.45 (m, 10H) 3.47–3.74 (m, 2H), minor conformational isomer 5.00 (d, J=7.0 Hz, 1H), major isomer 5.30 (dd, J=5.9 Hz, 2.6 Hz, 1H), minor conformational isomer 5.91 (s, 1H), major isomer 5.96 (s, 1H).

13 b. 5-(1-Ethyl-2(S)-pyrrolidinyl)-3-methyl-isoxazole

The product from Example 13a (108 mg, 0.56 mmol) in 1.0 mL of anhydrous tetrahydrofuran was treated with a 1.0 M solution of lithium aluminum hydride in tetrahydrofuran (506 μL, 0.56 mmol). The reaction was allowed to stir at ambient temperature for 2 hours and then worked up under standard conditions found in Fleser and Fleser Vol. 1, p.584. The crude product was then purified using flash chromatography on silica gel eluted with ethyl acetate/hexane (1:1) to give 63 mg (63% yield) of the title compound (13b) as a clear oil. MS (DCl/NH$_3$) m/e 181 (M+H)+. $^1$H NMR (CDCl$_3$, 300 MHz) δ: 1.07 (t, J=7.2 Hz, 3H), 1.82–2.00 (m, 3H), 2.14–2.47 (m, 3H), 2.28 (s, 3H), 2.72 (dq, J=12.1 Hz, 7.4 Hz, 1H), 3.19–3.27 (m, 1H), 3.60 (dd, J=8.3 Hz, 6.4 Hz, 1H), 5.97 (s, 1H).

13 c. 5-(1-Ethyl-2(S)-pyrrolidinyl)-3-methyl-isoxazole hydrochloride salt

The product from Example 13b (59 mg, 0.33 mmol) was processed in the same manner set forth in Example 11. The white solid obtained was dissolved in methylene chloride/hexane and recrystallized to give 41 mg (58% yield) of the title compound (13) as fine white needles. m.p.=166°–168° C. $[\alpha]^{23}_D = -33.3°$ (c 0.33, MeOH). MS (DCl/NH$_3$) m/e 181 (M+H)+. $^1$H NMR (D$_2$O, 300 MHz) δ: 1.27 (t, J=7.4 Hz, 3H), 2.18–2.41 (m, 4H), 2.31 (s, 3H), 2.50–2.62 (m, 1H), 3.10–3.23 (m, 1H), 3.28–3.33 (m, 2H), 3.69–3.82 (m, 1H), 6.61 (s, 1H).

Anal. calcd. for C$_{10}$H$_{17}$ClN$_2$O: C, 55.42; H, 7.91; N, 12.93. Found: C,55.25; H,7.97; N, 12.73.

EXAMPLE 14

3-Methyl-5-(2(S)-pyrrolidinyl)-isoxazole oxalate salt 14 a. (2R)-Ethynyl-N-t-butyloxycarbonylpyrrolidine The title compound was prepared in the manner set forth in Examples 1 a–c. $[\alpha]^{23}_D = +113.0°$ (c 0.94, MeOH).

14 b. 3-Methyl-5-(N-t-butyloxycarbonyl-2(R)-pyrrolidinyl)-isoxazole

The product from Example 14a (1.96 g, 10.04 mmol), phenyl isocyanate (2.45 mL, 22.59 mmol), nitroethane (1.1 mL, 15.06 mmol) and a catalytic amount of triethylamine were treated in the manner set forth in Example 1 d to give 1.52 g (60% yield) of the title compound (14b) as a light amber oil. $[\alpha]^{23}_D = +102.4°$ (c 0.70, MeOH). MS and $^1$H NMR are similar to those reported in Example 1 d.

14 c. 3-Methyl-5-(2(R)-pyrrolidinyl)-isoxazole

The product from Example 14b (1.41 g, 5.59 mmol) was treated in the same manner set forth in Example 1 e to give 663 mg (78% yield) of the title compound (14c) as a light amber oil. $[\alpha]^{23}_D = +11.6°$ (c 1.0, MeOH). MS and $^1$H NMR are similar to those described under Example 1 e.

14 d. 1-Methyl-5-(2(R)-pyrrolidinyl)-isoxazole oxalate salt

The product from Example 14c (48.5 mg, 0.32 mmol) was treated in the same manner set forth in Example 1f, The process yielded 63 mg (81% yield) of the title compound (14d) as a white solid, m.p.=133.5°–134.5° C. $[\alpha]^{23}_D = +11.4°$ (c 0.55, MeOH). MS and $^1$H NMR are similar to those described under Example I f. Anal. calcd. for C$_{10}$H$_{14}$N$_2$O$_5$: C, 49.58; H, 5.82; N, 11.50. Found: C, 49.57; H, 5.72; N,11.56.

EXAMPLE 15

3-Methyl-5-(2(R)-pyrrolidinyl)-isoxazole benzoate salt

1-Methyl-5-(2(R)-pyrrolidinyl)-isoxazole benzoate salt

The product of example 14c (855 mg, 5.62 mmol) was dissolved in diethyl ether. At ambient temperature, benzoic acid (755 mg, 6.18 retool) was then added in one portion. The reaction was allowed to stir for one hour after which the ether was evaporated. The remaining solid was then recrystallized from hot diethyl ether (2X) to give 601 mg (39% yield) of the title compound (15) as pale-tan long needles, m.p.=90.5°–91.5° C. $[\alpha]^{23}_D = +9.5°$ (c 0.58, MeOH). MS (DCl/NH$_3$) m/e 153 (M+H)+, 170 (M+NH$_4$)+. $^1$H NMR (CDCl$_3$, 300 MHz) δ: 1.95–2.23 (m, 3H), 2.22 (s, 3H), 2.24–2.38 (m, 1H), 3.00–3.32 (m, 2H), 4.62 (dd, J=7.4 Hz, 5.9 Hz, 1H), 6.12 (s, 1H), 7.39–7.44 (m, 2H), 7.49–7.55 (m, 1H), 8.01–8.04 (m, 2H), 8.14 (br s, NH). Anal. calcd. for C$_{15}$H$_{18}$N$_2$O$_3$: C, 65.68; H, 6.61; N, 10.21. Found: C, 65.61; H, 6.50; N, 10.16.

EXAMPLE 16

3-Methyl-5-(1-methyl-2(R)-pyrrolidinyl)-isoxazole hydrochloride salt 16 a. 3-Methyl-5-(1-methyl-2(R)-pyrrolidinyl)-isoxazole The product from Example 14c (370 mg, 2.43 mmol) was treated in the same manner as set forth in Example 2a. The title compound (16a) 258 mg (64% yield), was isolated as a clear oil. $[\alpha]^{23}_D = +101.0°$ (c 0.76, MeOH).

MS and $^1$H NMR are similar to those described under Example 2a.

16 b. 3-Methyl-5-(1-methyl-2(R)-pyrrolidinyl)-isoxazole hydrochloride salt

The product from Example 16a (228 mg, 1.37 mmol) was converted into a hydrochloride salt using the method described in Example 10d. The white solid obtained was recrystallized from MeOH/Et$_2$O to give 248 mg (89% yield) of the title compound (16) as white needles, m.p.=154°–155° C. $[\alpha]^{23}{}_D 632$ +29.1° (c 0.80, MeOH). MS and $^1$H NMR are similar to those described under Example 15. Anal. calcd. for C$_9$H$_{15}$ClN$_2$O: C, 53.33; H, 7.46; N, 13.82. Found: C, 53.21; H, 7.71; N, 13.78.

EXAMPLE 17

3-Ethyl-5-(2(R0-pyrrolidinyl)-isoxazole oxalate salt 17 a. 3-Ethyl-5-(N-t-butyloxycarbonyl-2(R)-pyrrolidinyl)-isoxazole The product of Example 14a (655 mg, 3,35 mmol), phenyl isocyanate (1.3 mL, 12.1 mmol), nitropropane (600 μL, 6.7 mmol) and a catalytic amount of triethylamine were treated in the manner set forth in Example 1 d. The process yielded 660 mg (74% yield) of the title compound (17a) as a clear yellow oil. MS and $^1$H NMR are similar to those described under Example 3a.

17 b. 3-Ethyl-5-(2(R)-pyrrolidinyl-isoxazole

The product from Example 17a (650 mg, 2.44 mmol) was treated in the same manner as that described in Example 1e. The process yielded 268 mg (68% yield) of the title compound (17b) as a clear yellow oil. MS and $^1$H NMR are similar to those described under Example 3b.

17 c. 3-Ethyl-5-(2(R)-pyrrolidinyl)-isoxazole oxalate salt

The product of Example 17b (84 mg, 0.51 mmol) was treated with oxalic acid (50 mg, 0.55 mmol) in the same manner set forth in Example 3c. The solid obtained was recrystallized from MeOH/Et$_2$O to give 88 mg (67% yield) of the title compound (17) as white crystals, m.p.=131°–132° C. $[\alpha]^{23}{}_D$=+8.3° (c 0.46, MeOH). MS and $^1$H NMR are similar to those described under Example 3c. Anal. calcd. for C$_{11}$H$_{16}$N$_2$O$_5$: C, 51.56; H, 6.29; N, 10.93. Found: C, 51.62; H, 6.21; N, 10.88.

EXAMPLE 18

3-Ethyl-5-(1-methyl-2(R)-pyrrolidinyl)-isoxazole hydrochloride salt 18 a. 3-Ethyl-5-(1-methyl-2(R)-pyrrolidinyl)-isoxazole The product from Example 17b (152 mg, 0.91 mmol) was treated in the same o manner set forth in Example 2a. The process yielded 138 mg (84% yield) of the title compound (18a) as a clear oil. The MS and $^1$H NMR are similar to those described under Example 4a.

18 b. 3-Ethyl-5-(1-methyl-2(R)-pyrrolidinyl)-isoxazole hydrochloride salt

The product from Example 18a (130 mg, 0.72 mmol) was converted into the hydrochloride salt by the procedure described in Example 16. The white precipitate obtained was recrystallized from MeOH/Et$_2$O to give 66 mg (42% yield) of the title compound (18) as fine white needles, m.p.=134°–135° C. $[\alpha]^{23}{}_D$=+33.2° (c 0.44, MeOH). The MS and $^1$H NMR are similar to those described under Example 4b. Anal. calcd. for C$_{10}$H$_{17}$ClN$_2$O: C, 55.42; H, 7.91; N, 12.93. Found: C, 55.06; H, 7.92; N,12.64.

EXAMPLE 19

3-methyl-5-((2(R)-pyrrolidinyl)-isothiazole hydrochloride 19 a. (2R)-(3-hydroxy-1-butynyl)-N-t-butyloxycarbonyl pyrrolidine The title compound (19a) was prepared in the manner described in Example 5a.

19 b. ((2R)-(3-keto-1-butynyl)-N-t-butyloxycarbonyl pyrrolidine

The title compound (19b) was prepared in the manner described in Example 5b. $[\alpha]^{23}{}_D$=+143.6° (c 1.6, CH$_2$Cl$_2$).

19 c. 3-methyl-5-(N-t-butyloxycarbonyl-(2R)-pyrrolidinyl)-isothiazole

The title compound (19c) was prepared in the manner described in Example 5c. $[\alpha]^{23}{}_D$=+107.7° (c 1.0, CH$_2$Cl$_2$).

19 d. 3-methyl-5-((2(R)-pyrrolidinyl)-isothiazole hydrochloride

The title compound (19) was prepared in the manner described in Example 5d. $[\alpha]^{23}{}_D$=−14.8° (c 0.7, MeOH).

EXAMPLE 20

3-Methoxymethyl-5-(1-methyl-2(S)-pyrrolidinyl)-isoxazole fumarate salt 20 a. 3-Hydroxymethyl-5-(N-t-butyloxycarbonyl-2(S)-pyrrolidinyl)isoxazole 3-Ethoxycarbonyl-5-(N-t-butyloxycarbonyl-2(S)-pyrrolidinyl) isoxazole (7.10 g), of ~90% pure material, was prepared using methodology reported by Eung K. Ryu, Heterocycles, 1990, 31:1693. The compound was then placed in a solution of potassium hydroxide (1.35 g)in (1:1) ethanol:water (70 mL) and allowed to stir overnight at room temperature. The reaction mixture was then acidified with 2N HCl and extracted with chloroform (3X). The organics were combined, dried over Na$_2$SO$_4$ and concentrated. The concentrated material was purified using flash chromatography with 10% MeOH in CHCl$_3$ to 10% MeOH in CHCl$_3$ with 0.5 % acetic acid. The product was azeotroped with toluene (2X), benzene (2X) and finally the solvents were evaporated in vacuo to give 3.09 grams of a yellow foamy solid. TLC R$_f$=0.16 (10 % MeOH in CHCl$_3$ and three drops of AcOH).

The acid (387 mg, 1.37 mmol) and 1.0 M borane THF complex (4.80 mL, 4.80 mmol) were combined at room temperature in THF (4.5 mL) and then heated to reflux for 4 hours. After refluxing, the reaction was allowed to cool to room temperature. When the reaction reached room temperature, saturated NaHCO$_3$ solution was added. The mixture was stirred for one hour and then combined with ethyl acetate. Two phases formed and were separated. The aqueous phase was extracted with CHCl$_3$ (1X) and the organic extract was combined with the original organic phase. The mixture was then dried over Na$_2$SO$_4$, concentrated in vacuo and purified by flash chromatography using 2 % MeOH in CHCl$_3$ as the elutant to give a clear viscous oil (266 mg), 72 % yield. TLC R$_f$=0.54 (10% MeOH in CHCl$_3$ and three drops AcOH). MS(Cl) m/e (M+H)+269. $^1$H NMR (DMSO-d$_6$, 100° C., 500 MHz) δ: 6.17 (s, 1H), 4.94 (dd, J=8.4, 2.8 Hz, 1H), 4.47 (s, 2H), 3.46–3.37 (m, 2H), 2.29–2.20 (m, 1H), 1.96–1.87 (m, 3H), 1.35 (s, 9H).

20 b. 3-Methoxymethyl-5-(N-t-butyloxycarbonyl-2(S)-pyrrolidinyl)isoxazole

The product of example 20a (274 mg, 1.02 mmol), in ~1 mL of anhydrous THF, was added to a stirring slurry of 80 % sodium hydride (31 mg, 1.02 mmol), in ~1 mL of anhydrous THF. The reaction was allowed to stir for 15 minutes at ambient temperature. Iodomethane (190 mL, 3.06 mmol) was then added via syringe. After an additional 15 minutes of stirring, the reaction was poured over ethyl acetate/saturated aqueous NH$_4$Cl solution. Two phases formed and the phases were separated. The organic phase was dried over Na$_2$SO$_4$, concentrated in vacuo and the residue purified by flash chromatography using ethyl acetate/hexane (1:3) as the elutant. The purification yielded 234 mg of a clear yellow oil (81% yield). MS(Cl) m/e (M+H)+283. $^1$H NMR (DMSO-d$_6$, 100° C., 500 MHz) δ: 6.20 (s, 1H), 4.94 (dd, J=7.8, 2.6 Hz, 1H), 4.43 (s, 2H), 3.47–3.36 (m, 2H), 3.32 (s, 3H), 2.30–2.22 (m, 1H), 1.96–1.87 (m, 3H), 1.34 (s, 9H).

20 c. 3-Methoxymethyl-5-(1-methyl-2-(S)-pyrrolidinyl) isoxazole

The product from Example 20b (220 mg, 779 mmol) was cooled neat to 0° C. Approximately 6 mL of 4.0 N HCl in 1,4-dioxane was then introduced into the reaction vessel. The ice bath was removed and the reaction was stirred for ~2 hours. The solvent was evaporated in vacuo.

The crude product was dissolved in ~3 mL of 88% formic acid and ~3 mL of 37% aqueous formaldehyde. The reaction was heated at a gentle reflux for ~30 minutes and then allowed to cool to room temperature. The aqueous solution was extracted once with Et$_2$O and then basified with saturated NaHCO$_3$ solution followed by solid K$_2$CO$_3$. The basified solution was then extracted with CHCl$_3$ (3X). The chloroform extracts were combined, dried over Na$_2$SO$_4$, concentrated in vacuo and the residue purified by flash chromatography to give 142 mg of the title compound (20c) in 93% overall yield. MS(Cl) m/e (M+H)+197. $^1$H NMR (CDCl$_3$, 300 MHz) δ: 6.20 (s, 1H), 4.51 (s, 2H), 3.47 (dd, J=8.1,7.4 Hz, 1H), 3.39 (s, 3H), 3.20–3.13 (m, 1H), 2.42–2.30 (m, 1H), 2.34 (s, 3H), 2.28–2.20 (m, 1H), 2.03–1.80 (m, 3H).

20 d. 3-Methoxymethyl-5-(1-methyl-2(s)-pyrrolidinyl)isoxazole fumarate salt

The product from Example 20c (34 mg, 0.17 mmol) and fumaric acid (20 mg, 0.17 mmol) were combined in ~1 mL of MeOH and stirred for 30 minutes. The solvent was evaporated in vacuo and the remaining viscous oil was left on the high vacuum line overnight to give 37 mg of the title compound (20) as a clear viscous oil (60% yield). MS(Cl) m/e (M+H)+197. $^1$H NMR (MeOD, 300 MHz) δ: 6.72 (s, 2H fumarate), 6.54 (s, 1H), 4.52 (s, 2H), 4.08 (dd, J=8.1,8.1 Hz, 1H), 3.43–3.37 (m, 1H), 3.39 (s, 3H), 2.82 (ddd, J=10.7, 10.3, 8.5, 1H), 2.58 (s, 3H), 2.48–2.37 (m, 1H), 2.24–2.03 (m, 3H). Anal. calcd. for C$_{14}$H$_{20}$N$_2$O$_6$.0.4C$_4$H$_4$O$_4$.0.2H$_2$O: C, 51.71; H, 6.12; N, 7.73. Found: C, 51.76; H, 6.45; N, 7.60.

EXAMPLE 21

3-Methyl-5-(trans-4-hydroxy-1-methyl-2-pyrrolidinyl)-isoxazole oxalate salt 21 a. trans-3-Hydroxyproline methyl ester hydrogen chloride salt Acetyl chloride (15.7 ml, 0.22 mol) was slowly added to a solution of trans-4-hydroxyproline (26.2 g, 0.20 tool)in methanol (800 ml). The reaction was carried out at room temperature and the resulting solution was allowed to stir for forty eight hours. After evaporation of the solvents in vacuo, the title compound (21 a) was obtained as a white solid in quantitative yield. MS (DCl/NH$_3$) m/e 146 (M+H)+, 163 (M+NH$_4$)+, 291 (2M+H)+. $^1$H NMR (DMSO) δ: 5.54 (s, 1H, NH), 4.43 (dd, J=9.0 Hz, J=8.1 Hz, 1 1H, CHCO), 4.35–4.40 (m, 1H, OCH), 3.72 (s, 3H, OCH$_3$), 3.28–3.38 (m, 1H, NCHH), 3.03 (ddd, J=11.1 Hz, J=1.8 Hz, J=1.8 Hz, NCHH), 2.15 (dddd, J=13.5 Hz, J=8.1 Hz, J=1.8 Hz, J=1.8 Hz, 1H, OCCHH), 2.04 (ddd, J=13.5 Hz, J=9.0 Hz, J=4.5 Hz, 1H, OCCHH).

21 b. trans-4-(2,4,6-Trimethylbenzoyloxy)proline methyl ester

Trifluoroacetic anhydride (0.93 mL, 6.60 mmol) was added dropwise to a suspension of trans-4-hydroxy proline methyl ester hydrochloride salt (21 a, 1.00 g, 5.50 mmol) and 2,4,6-trimethyl benzoic acid (1.08 g, 6.60 mmol) in methylene chloride (20 mL). The addition was carried out at room temperature and the resulting clear solution was allowed to stir at room temperature for 30 minutes. The reaction mixture was then basified with 2N NaOH to pH=12, and extracted with chloroform (30 mL 4X). The chloroform extracts were combined, washed with brine, dried over anhydrous magnesium sulfate and concentrated in vacuo. The title compound (21 b) was obtained as an oil, which was directly used for the next reaction without further purification. TLC R$_f$=0.33 (ethyl acetate:hexane=2:1). MS (DCl/NH$_3$) m/e 292 (M+H)+. $^1$H NMR (CDCl$_3$) δ: 6.85 (s, 2H, 2ArH), 5.49–5.55 (m, 1H, OCH), 4.01 (dd, J=9.0 Hz, J=9.0 Hz, 1H, COCH), 3.76 (s, 3H, OCH$_3$), 3.43 (dd, J=13.5 Hz, J=4.5 Hz, 1H, NCHH), 3.18 (ddd, J=13.5 Hz, J=1.5 Hz, J=1.5 Hz, NCHH), 2.38 (dddd, J=14.7 Hz, J=9.0 Hz, J=1.5 Hz, J=1.5 Hz, 1H, CHH), 2.29 (s, 6H, 2ARCH$_3$), 2.28 (s, 3H, ARCH$_3$), 2.19–2.29 (m, 1 H, CHH).

21. c. trans-1-Methyl-4-(2,4,6-trimethylbenzoyloxy) proline methyl ester

Iodomethane (573.0 mL, 9.20 mmol) was slowly added through a condenser at 0° C. To a suspension of trans-4-(2,4,6-trimethylbenzoyloxy) proline methyl ester (21 b, 1.35 g, 4.60 mmol) and triethylamine (1.29 mL, 9.20 mmol)in anhydrous methylene chloride (5 mL). The mixture was then refluxed overnight. Brine (20 mL) was then added to the mixture and the mixture was extracted with chloroform (30 mL 4X). The combined organic extracts were washed with brine, dried over anhydrous magnesium sulfate and concentrated in vacuo. The resulting residue was purified by flash chromatography on silica gel eluting with ethyl acetate/hexane (1:1) to give 543.0 mg (32% yield from 4-hydroxyproline methyl ester hydrochloride salt) of the title compound (21c) as an oil. TLC R$_f$=0.65 (ethyl acetate:hexane=2:1). MS (DCl/NH$_3$) m/e 306 (M+H)+. $^1$H NMR (CDCl$_3$) δ: 6.85 (s, 2H, 2ArH), 5.44–5.52 (m, 1H, OCH), 3.77 (s, 3H, OCH$_3$), 2.26–2.64 (m, 4H, 2CH$_2$), 2.47 (s, 3H, NCH$_3$), 2.30 (s, 6H, 2ARCH$_3$), 2.28 (s, 3H, ARCH$_3$).

21 d. 3-Methyl-5-(trans-4-(2,4,6-trimethylbenzoyloxy)-1-methyl-2-pyrrolidinyl)-isoxazole N-butyllithium (1.70 mL, 2.5 M, 4.26 mmol) was added dropwise at 0° C. to a solution of acetone oxime (155.5 mg, 2.13 mmol)in anhydrous THF (10.0 mL). The resulting solution was stirred at the same temperature for two hours. trans-1-Methyl-4-(2,4,6-trimethylbenzoyloxy) proline methyl ester (21c, 500.0 mg, 1.64 mmol)in anhydrous THF (5.0 mL) was slowly added to the solution through syringe. The resulting mixture was further stirred at 0 ° C for eight hours and slowly warmed to room temperature overnight. THF was then evaporated in vacuo. A THF-sulfuric acid solution (10.0 mL, prepared in a ratio of sulfuric acid: THF: $H_2O=8.2$ g: 40 mL: 10 mL) was added and the mixture was refluxed for two hours. The mixture was made basic with 10% NaOH and extracted with ethyl acetate (30 mL 4X). The combined organic extracts were washed with brine, dried over anhydrous magnesium sulfate and concentrated in vacuo. The resulting residue was purified by flash chromatography on silica gel eluting with ethyl acetate/hexane (1:1 and 2:1) to give 112.5 mg (21% yield) of the title compound (21 d) as an oil. TLC $R_f=0.63$ (ethyl acetate:hexane=2:1 ). MS (DCI/NH$_3$) m/e 329 (M+H)+. $^1$H NMR (CDCl$_3$) δ: 6.86 (s, 2H, 2ArH), 6.03 (s, 1 H, isoxazole H), 5.48–5.54 (m, 1 H, OCH), 3.76 (dd, J =9.6, J=6.3 Hz, 1H, ArCHN), 2.38–2.61 (m, 4H, 2CH2), 2.44 (s, 3H, NCH3), 2.31 (s, 6H, 2ARCH3), 2.30 (s, isoxazole-CH3), 2.29 (s, 3H, ARCH3).

21 e. 3-Methyl-5-(trans-4-hydroxy-1-methyl-2-pyrrolidinyl)-isoxazole

A solution of 3-methyl-5-(trans-4-(2,4,6-trimethylbenzoyloxy)-1-methyl-2-pyrrolidinyl)-isoxazole (21 d, 350.0 mg, 1.07 mmol)in 2.0 mL of KOH solution (prepared in a ratio of KOH: EtOH: H$_2$O=10 g: 30 mL: 2 mL) was refluxed for two hours. Direct chromatography of the residue on silica gel eluting with CHCl$_3$/MeOH (20:1) gave 171.0 mg (88% yield) of the title compound (21e) as an oil. TLC $R_f=0.65$ (CHCl$_3$:MeOH=5:1). MS (DCl/NH$_3$) m/e 183 (M+H)+, 200 (M+NH$_4$)+. $^1$H NMR (CDCl$_3$) δ: 6.03 (s, 1H, ArH), 4.55–4.63 (m, 1H, OCH), 3.93 (dd, J=8.7 Hz, J=8.7 Hz, 1H, ArCHN), 3.53 (dd, J=9.0 Hz, J=5.7 Hz, 1H, NCHH), 2.52 (dd, J=9.0 Hz, J=4.2 Hz, 1H, NCHH), 2.36 (s, 3H, NCH3), 2.33 (ddd, J=14.1 Hz, J=8.7 Hz, J=2.4 Hz, 1H, OCCHH),2.29 (s, 3H, ArCH3),2.18 (ddd, J=14.1 Hz, J=8.7 Hz, J=3.0 Hz, 1H, OCCHH).

21 f. 3-Methyl-5-(trans-4-hydroxy-1-methyl-2-pyrrolidinyl)-isoxazole oxalate salt A solution of oxalic acid (13.6 mg, 0.151 mmol) in diethyl ether was added dropwise to a stirring solution of 3-methyl-5-(trans-4-hydroxy-1-methyl-2-pyrrolidinyl)-isoxazole (21 e, 25.0 mg, 0.14 mmol) in diethyl ether. After 30 minutes of stirring at ambient temperature, the resulting precipitate was filtered and washed with diethyl ether three times to give, after evaporation of the solvents in vacuo., 26.0 mg of the title compound (21). M.P. 125°–126° C. MS (DCI/NH$_3$) m/e 183 (M+H)+, 200 (M+NH$_4$)+. $^1$H NMR (D$_2$O) δ: 6.67 (s, 1H, ArH), 5.07–5.17 (m, 1H, OCH), 4.82 (dd, J=10.5 Hz, J=9.9 Hz, 1H, ArCHN), 3.93–4.03 (m, 1H, NCHH), 3.34–3.43 (m, 1H, NCHH), 2.98 (s, 3H, NCH3), 2.66 (ddd, J=14.4 Hz, J=10.5 Hz, J=4.8 Hz, 1H, OCCHH), 2.55 (dddd, J=14.4 Hz, J=9.9 Hz, J=1.8 Hz, J=1.8 Hz, 1H, OCCHH), 2.33 (s, 3H, ARCH3). Anal. calcd. for C$_{11}$H$_{16}$N$_2$ 6$l$ 0$_6$: C, 48.53; H, 5.88; N, 10.29. Found: C, 48.58; H, 5.83; N, 10.04.

EXAMPLE 22

3-Methyl-5-(trans-4-fluoromethyl-1-methyl-2-pyrrolidinyl)-isoxazole hydrochloride 22 a. Pyroglutamic acid methyl ester Thionyl chloride (16.5 mL, 0.23 mol), DMF (0.20 mL) and pyroglutamic acid (15.0 g, 0.116 mol) were sequentially added to a solution of absolute methanol (50 mL) at −15° C. The mixture was slowly warmed to room temperature and stirred for eighteen hours. After evaporation of the methanol, the resulting residue was dissolved in ethyl acetate (400 mL) and water (20 mL), followed by the slow addition of sodium bicarbonate (20.0 g). After the mixture was vigorously stirred for 30 minutes, the organic layer was decanted and dried over anhydrous magnesium sulfate. Removal of the solvent gave 15.6 g (94% yield) of the title compound (22a). TLC $R_f=0.42$ (CHCl$_3$:MeOH=10:1). MS (DCl/NH$_3$) m/e 144 (M+H)+, 161 (M+NH$_4$)+. $^1$H NMR (CDCl$_3$) δ: 6.01 (s, 1H, NH), 4.27 (dd, J=8.1 Hz, J=4.5 Hz, 1H, NCH), 3.78 (s, 3H, CH3), 2.20–2.54 (m, 4H, 2CH2).

22 b. 1-Methyl pyroglutamic acid methyl ester

A solution of pyroglutamic acid methyl ester (22a, 10.0 g, 69.9 mmol) in DMF (40 mL) was slowly added at room temperature to a suspension of sodium hydride (2.29 g, 80%, 76.2 mmol) in DMF (100 mL). After the evolution of hydrogen stopped, iodomethane (8.67 mL, 139.8 mmol) was added dropwise, and the solution was stirred for two hours. Ethyl acetate (200 mL) and hexane (500 mL) were then added, and a precipitate was filtered off. The precipitate was washed with ethyl acetate (20 ml 3X) and the washings were combined with the original solution. The solution was concentrated and the remaining residue was distilled to give 8.50 g (78% yield) of the title compound (22b). B.P. 107°–109° C./2.7 mmHg. TLC $R_f=0.49$ (CHCl$_3$:MeOH=10:1). MS (DCl/NH$_3$) m/e 158 (M+H)+, 175 (M+NH$_4$)+. $^1$H NMR (CDCl$_3$) δ:4.13 (dd, J=9.0 Hz, J=3.9 Hz, 1H, NCH), 3.78 (s, 3H, OCH3), 2.86 (s, 3H, NCH3), 2.04–2.54 (m, 4H, 2CH2).

22 c. 3-Methyl-5-(1-methyl-5-oxo-2-pyrrolidinyl)-isoxazole

N-butyllithium (108.8 mL, 2.5 M, 272.0 mmol)in hexane was slowly added to a cooled (0°–5° C.) solution of acetone oxime (9.92 g, 135.9 mmol) in THF (300 mL). After being stirred at 0°–5° C. for one hour, a solution of 1-methyl-pyroglutamic acid methyl ester (22b, 16.32 g, 104 mmol) in THF (50 mL) was added. After being stirred for additional eight hours, the resulting reaction mixture was slowly warmed to room temperature overnight. THF was evaporated, and a sulfuric acid solution in THF (160 mL, prepared in the ratio of H$_2$SO$_4$: H$_2$O: THF=8.2 g: 10 mL: 40 mL) was added, and the mixture was allowed to reflux for one hour. After the evaporation of THF, the residue was first extracted with chloroform (80 mL 6X), then continuously extracted with chloroform (120 mL) overnight. All the organic phases were combined and dried over magnesium sulfate. The residue obtained after evaporation of the solvents was flash chromatographed on a silica gel column eluting with CHCl$_3$/MeOH (20/1) to give 13.1 g (70% yield) of the title compound (22c) as an oil. TLC $R_f=0.49$ (CHCl$_3$:MeOH=10:1). MS (DCl/NH$_3$) m/e 181 (M+H)+, 198 (M+NH$_4$)+. $^1$H NMR (CDCl$_3$) δ: 5.99 (s, 1H, Ar-H), 4.71 (dd, J=8.1 Hz, J=4.5 Hz, 1H, ArCHN), 2.80 (S, 3H, NCH3), 2.32 (s, 3H, CH3), 2.95–3.25 (m, 1H, COCH), 2.18–2.64 (m, 3H).

22 d. 3-Methyl-5-(trans-4-hydroxymethyl-1-methyl-5-oxo-2-pyrrolidinyl)-isoxazole and 22 e. 3-Methyl-5-(cis-4-hydroxymethyl-1-methyl-5-oxo-2-pyrrolidinyl)-isoxazole LDA (14.67 mL, 1.5 M, 22.0 mmol) was slowly added to a cooled (−78° C.) solution of 3-methyl-5-(1-methyl-5-oxo-2-pyrrolidinyl)-isoxazole (22c, 3.60 g, 20.0 mmol) in THF (100 mL). The resulting solution was stirred at −78° C. for 30 minutes. The mixture was then warmed to −20 ° C., and formaldehyde, generated by heating paraformaldehyde on a 140° C. oil bath, was gently bubbled into the mixture until saturation (over one hour). The reaction mixture was stirred for an additional 30 minutes before methanol (5.0 mL) was added. The solvents were evaporated in vacuo, and the residue was purified on silica gel eluting with CHCl₃/MeOH (40:1) to give 2.63 g (63% yield) of the title compounds (22d & 22e) as an inseparable mixture (trans: cis=2.5:1 by NMR spectroscopy analysis). TLC R$_f$=0.37 (CHCl₃:MeOH=20:1). MS (DCl/NH₃) m/e 211 (M+H)⁺, 228 (M+NH₄)⁺. 3-Methyl-5-(trans-4-hydroxymethyl-1-methyl-5-oxo-2-pyrrolidinyl)-isoxazole (22d): ¹H NMR (CDCl₃) δ: 5.99 (s, 1 H, ArH), 4.68 (dd, J=9.2 Hz, J=4.8 Hz, 1H, ArCHN), 3.96 (dd, J=12.0 J=4.8 Hz, 1H, OCHH), 3.73 (dd, J=12.0 Hz, J=6.6 Hz, 1H, OCHH), 2.75–2.81 (m, 1H, COCH), 2.84 (s, 3H, NCH₃), 2.34 (ddd, J=12.9 Hz, J=9.6 Hz, J=4.8 Hz, 1H, CHH), 2.30 (s, 3H, ARCH₃), 2.24 (ddd, J=12.9 Hz, J=9.2 Hz, J=3.9 Hz, 1H, CHH). 3-Methyl-5-(cis-4-hydroxymethyl-1-methyl-5-oxo-2-pyrrolidinyl)-isoxazole (22e): ¹H NMR (CDCl₃), δ: 6.09 (s, 1H, ArH), 4.71 (dd, J=8.8 Hz, J =5.7 Hz, 1H, ArCHN), 3.93 (dd, J=12.0 Hz, J=4.8 Hz, 1H, OCHH), 3.79 (dd, J=12.0 Hz, J=6.6 Hz, 1H, OCHH), 2.75–2.81 (m, 1H, COCH), 2.75 (s, 3H, NCH₃), 2.58 (ddd, J=16.5 Hz, J=8.8 Hz, J=7.5 Hz, 1H, CHH), 2.33 (s, 3H, ARCH₃), 1.96 (ddd, J=16.5 Hz, J=8.2 Hz, J=5.7 Hz, 1H, CHH).

22 f. 3-Methyl-5-(trans-4-fluoromethyl-1-methyl-5-oxo-2-pyrrolidinyl)-isoxazole and 22 g. 3-Methyl-5-(cis-4-fluoromethyl-1-methyl-5-oxo-2-pyrrolidinyl)-isoxazole A mixture of the cis and trans isomers of 3-methyl-5-(4-hydroxymethyl-1-methyl-5-oxo-2-pyrrolidinyl)-isoxazole (22d, 22e, 21 0.0 mg, 1.0 mmol)in methylene chloride (2.0 mL) was added dropwise to a cooled (−78° C.) solution of DAST (0.198 mL, 1.50 mmol) in methylene chloride (2.0 mL). After being stirred at −78° C. for two hours, the resulting solution was slowly warmed to room temperature and stirred for an additional four hours. Methanol (10 mL) was then added, and the solution was made basic with a 50% sodium hydroxide solution. The precipitates were filtered off and washed with ethyl acetate (2 mL 3X). The filtrate and washings were then combined and concentrated in vacuo. The residue was chromatographed on a silica gel column eluting with CHCl3/MeOH (40:1 and 20:1) to give 246.0 mg of the crude title compounds (22f & 22g) as an inseparable mixture (trans:cis=3:1 by NMR spectroscopy), which was directly used for the next reaction without further purification. TLC R$_f$=0.49 (CHCl₃:MeOH=20:1). MS (DCl/NH₃) m/e 213 (M+H)⁺, 230 (M+NH₄)⁺. 3-Methyl-5-(trans-4-fluoromethyl-1-methyl-5-oxo-2-pyrrolidinyl)-isoxazole (22f): ¹H NMR (CDCl₃) δ: 6.00 (s, 1H, ArH), 4.62 (dddd, J=45.0 Hz, J=9.0 Hz, J=9.0 Hz, J=3.6 Hz, 2H, CH₂F), 4.68–4.74 (m, 1 H, ArCHN), 2.65–3.00 (m, 1 H, COCH), 2.84 (s, 3H, NCH₃), 2.28–2.40 (m, 2H), 2.30 (s, 3H, ARCH₃). 3-Methyl-5-(cis-4-fluoromethyl-1-methyl-5-oxo-2-pyrrolidinyl)-isoxazole (22g): ¹H NMR (CDCl₃) δ: 6.08 (s, 1H, ArH), 4.85 (ddd, J=45.0 Hz, J=8.1 Hz, J=4.2 Hz, 2H, CH₂F), 4.68–4.74 (m, 1H, ArCHN), 2.65–3.00 (m, 2H), 2.78 (s, 3H, NCH₃), 2.30 (s, 3H, ARCH₃), 2.12–2.25 (m, H).

22 h. 3-Methyl-5-(trans-4-fluoromethyl-1-methyl-2-pyrrolidinyl)-isoxazole and 22 i. 3-Methyl-5-(cis-4-fluoromethyl-1-methyl-2-pyrrolidinyl)-isoxazole A borane-THF solution (3.0 mL, 1.0 M, 3.0 mmol) was slowly added at room temperature to the solution of 3-methyl-5-(4-fluoromethyl-1-methyl-5-oxo-2-pyrrolidinyl)-isoxazole (22f and 22g, the entire crude product from the above reaction) in THF (8.0 mL). The resulting mixture was refluxed for two hours. The solvents were then evaporated in vacuo, then ethanol(12.0 mL) was added, followed by the addition of cesium fluoride (348.0 mg, 3.0 mmol). The mixture was then allowed to reflux overnight. Solvents were evaporated again in vacuo, and the residue was purified on silica gel eluting with CHCl₃/MeOH (40:1 to 20:1) to give 34.0 mg (17% overall yield from the alcohol) of the cis isomer and 91.0 mg (46% overall yield from the alcohol) of the trans isomer of the title compounds. 3-Methyl-5-(trans-4-fluoromethyl-1-methyl-2-pyrrolidinyl)-isoxazole (22h): TLC R$_f$=0.48 (CHCl₃:MeOH =20:1). MS (DCl/NH₃) m/e 199 (M+H)⁺. ¹H NMR (CDCl₃) δ: 6.02 (s, 1H, ArH), 4.50 (ddd, J=46.0 Hz, J=5.4 Hz, J=2.4 Hz, 2H, CH₂F), 4.49–3.56 (m, 1H, ArCHN), 3.26–3.34 (m, 1H, NCHH), 2.65–2.85 (m, 1H), 2.00–2.40 (m, 3H), 2.33 (s, 3H, NCH₃), 2.28 (s, 3H, ARCH₃). 3-Methyl-5-(cis-4-fluoromethyl-1-methyl-2-pyrrolidinyl)-isoxazole (22i): TLC R$_f$=0.50. MS (DCl/NH₃) m/e 199 (M+H)⁺. ¹H NMR (CDCl₃) δ: 6.0 (s, 1H, Ar-H), 4.30–4.60 (m, 2H, CH₂F), 4.35–3.48 (m, 1H, ArCHN), 3.05–3.18 (m, 1H), 2.80–2.90 (m, 1H), 2.25–2.45 (m, 3H), 2.32 (s, 3H, NCH₃), 2.31 (s, 3H, ARCH₃).

22 j. 3-Methyl-5-(trans-4-fluoromethyl-1-methyl-2-pyrrolidinyl)-isoxazole hydrochloride A solution of hydrogen chloride in diethyl ether was added dropwise to a stirring solution of 3-methyl-5-(trans-4-fluoromethyl-1-methyl-2-pyrrolidinyl)-isoxazole (22h, 19.8 mg, 0.10 mmol) in diethyl ether until precipitate no longer formed. The diethyl ether was then decanted and the resulting precipitate was triturated several times with diethyl ether to give, after evaporation of the solvent in vacuo, 24.0 mg of the title compound. MS (DCl/NH₃) m/e 199 (M+H)⁺, 216 (M+NH₄)⁺. ¹H NMR (D₂O) δ: 6.63 (s, 1 H, ArH), 4.68–4.76 (m, 1H, ArCHN), 4.61 (ddd, J=46.0 Hz, J=4.8 Hz, J=2.0 Hz, 2H, CH₂F), 3.88 (dd, J=12.6 Hz, J=8.7 Hz, 1H, NCHH), 3.25 (dd, J=12.6 Hz, J=8.7 Hz, 1H, NCHH), 2.85 (S, 3H, NCH₃), 2.95–3.25 (m, 1H), 2.43–2.66 (m, 2H), 2.33 (s, 3H, CH₃). Anal. calcd. for C₁₀H₁₆N₂OFCl.0.3HCl.0.1H₂O: C, 48.54; H, 6.72; N, 11.32. Found: C, 48.77; H, 6.52; N, 10.81.

EXAMPLE 23

3-Methyl-5-(cis-1-methyl-5-(cyanomethyl)-2-pyrrolidinyl)-isoxazole oxalate salt 23 a. 3-Methyl-5-(1-methyl-5-thioxo-2-pyrrolidinyl)-isoxazole Lawesson's reagent (547.0 mg, 1.35 mmol) was added to a solution of 3-methyl-5-(1-methyl-5-oxo-2-pyrrolidinyl)-isoxazole (22c, 450.0 mg, 2.50 mmol) in toluene (10.0 mL). The reaction mixture was allowed to reflux for 30 minutes before the solvent was evaporated in vacuo. The residue was purified on silica gel eluting with ethyl acetate/hexane (1:5 and 1:1) to give 431.0 mg (88% yield) of the title compound (23a). TLC R$_f$=0.61 (CHCl₃:MeOH=20:1). MS (DCl/NH₃) m/e 197 (M+H)⁺. ¹H NMR (CDCl₃) δ: 6.04 (s, 1H, ArH), 5.04 (dd, J=9.0 Hz, J=4.5 Hz, 1H, ArCHN), 3.19 (S, 3H, NCH₃), 3.05–3.28 (m, 2H, CSCH₂), 2.45–2.58 (m, 1H, CHH), 2.32 (s, 3H, ARCH₃), 2.17–2.30 (m, 1H, CHH).

23 b. 3-Methyl-5-(1-methyl-5-(cyanomethyl)-2-pyrrolidinyl)-isoxazole

Bromoacetonitrile (56.8 mL, 0.60 mmol) is added to a solution of 3-methyl-5-(1-methyl-5-thioxo-2-pyrrolidinyl)-isoxazole (23a, 98.0 mg, 0.50 mmol)in acetonitrile (2.0 mL). The reaction mixture is then allowed to stir overnight at room temperature. Triphenylphosphine (196.7 mg, 1.21 mmol) is then added to the reaction mixture. After three minutes, triethylamine (208.7 mL, 1.50 mmol) is added, and the reaction mixture was stirred overnight. The solvent is evaporated in vacuo, and the residue is purified on silica gel to give the title compound (23).

EXAMPLE 24

3-Methyl-5-(trans-1,4-dimethyl-2-pyrrolidinyl)-isoxazole oxalate salt 24 a. 3-Methyl-5-(trans-1,4-dimethyl-5-oxo-2-pyrrolidinyl)-isoxazole LDA (0.367 mL, mono-THF in hexane, 1.5 M, 0.55 mmol) was added to a cooled ($-78°$ C.) solution of 3-methyl-5-(1-methyl-5-oxo-2-pyrrolidinyl)-isoxazole (22c, 90.0 mg, 0.50 mmol) in THF (2.0 mL). After being warmed to $-25°$ C. and stirred for 2 hours, the solution was cooled again to $-78°$ C. Iodomethane (34.3 mL, 0.55 mmol) was then added dropwise to the solution. After being stirred at $-78°$ C. for another hour, the solution was slowly warmed to room temperature overnight. After evaporation of the solvent, the resulting residue was directly chromatographed on silica gel eluting with $CHCl_3$/MeOH (20:1) to give 69.0 mg (71% yield) of the title compound (24a) as an oil. TLC $R_f=0.49$ ($CHCl_3$:MeOH =20:1) MS ($DCl/NH_3$) m/e 195 $(M+H)^+$, 212 $(M+NH_4)^+$, 391 $(2M+H)^+$. $^1H$ NMR ($CDCl_3$) δ: 5.94 (s, 1H, ArH), 4.63 (dd, J=8.7 Hz, J=3.9 Hz, 1H, ArCHN), 2.84 (s, 3H, $NCH_3$), 2.63–2.74 (m, 1 H, COCH), 2.46 (ddd, J=12.9 Hz, J=8.7 Hz, J=3.9 Hz, 1H, CHH), 2.29 (s, 3H, $ARCH_3$), 2.04 (ddd, J=12.9 Hz, J=10.2 Hz, J=8.7 Hz, 1H, CHH), 1.23 (d, J=8.4 Hz, $CH_3$).

24 b. 3-Methyl-5-(trans-1,4-dimethyl-2-pyrrolidinyl)-isoxazole

A room temperature borane-THF solution (1.08 mL, 1.0 M, 1.08 mmol) was slowly added to a solution of 3-methyl-5-(trans-1,4-dimethyl-5-oxo-2-pyrrolidinyl)-isoxazole (24a, 65.0 mg, 0.36 mmol) in THF (3.0 mL). The resulting mixture was then refluxed for two hours. The solvents were evaporated in vacuo, and ethanol (4.0 mL) was added, followed by the addition of cesium fluoride (125 mg, 1.08 mmol). After being refluxed overnight, solvents were evaporated in vacuo, and the residue was purified on silica gel eluting with $CHCl_3$/MeOH (20:1) to give 35.6 mg (55% yield) of the title compound (24b) as an oil. TLC $R_f=0.49$ ($CHCl_3$:MeOH=20:1). MS ($DCl/NH_3$) m/e 181 $(M+H)^+$, 198 $(M+NH_4)^+$. $^1H$ NMR ($CDCl_3$) δ: 5.97 (s, 1H, ArH), 3.50 (dd J=8.4 Hz, J=8.1 Hz, 1H, ArCHN), 3.25 (dd, J=8.1 Hz, J=7.9 Hz, 1H, NCHH), 2.35–2.48 (m, 1H, $CHCH_3$), 2.33 (s, 3H, $NCH_3$), 2.28 (s, 3H, $ARCH_3$), 2.08–2.18 (m, 1H, CHH), 1.99 (dd, J=8.1 Hz, J=8.1 Hz, 1H, NCHH), 1.75–1.85 (m, 1H, CHH), 1.04 (d, J=4.5 Hz, $CH_3$).

24 c. 3-methyl-5-(trans-1,4-dimethyl-2-pyrrolidinyl)-isoxazole oxalate salt

A solution of oxalic acid (17.6 mg, 0.196 mmol) in diethyl ether was added dropwise to a stirring solution of 3-methyl-5-(trans-1,4-dimethyl-2-pyrrolidinyl)-isoxazole (24b, 32.0 mg, 0.178 mmol) in diethyl ether. After 0.5 hours of stirring at ambient temperature, the diethyl ether was decanted off and the resulting precipitate was triturated with diethyl ether three times to give, after evaporation of the solvents in vacuo, 31.0 mg of the title compound (24). MS ($DCl/NH_3$) m/e 181 $(M+H)^+$, 198 $(M+NH_4)^+$. $^1H$ NMR ($D_2O$) δ: 6.02 (s, 1H, Ar-H), 3.48–3.60 (m, 1H, ArCHN), 3.25–3.32 (m, 1H, NCHH), 2.40–2.50 (m, 1H, CHH), 2.34 (s, 3H, $NCH_3$), 2.28 (s, 3H, $ARCH_3$), 2.12–2.22 (m, 1H, $CHCH_3$), 1.98–2.06 (m, 1H, NCHH), 1.78–1.86 (m, 1H, CHH), 1.06 (d, J=4.5 Hz, $CH_3$). Anal. calcd. for $C_{12}H_{18}N_2O_5 \cdot 0.5C_2H_2O_4 \cdot 9.1$-$H_2O$: C, 49.24, H; 6.10; N, 8.83. Found: C, 49.06; H, 5.91; N, 9.02.

EXAMPLE 25

3-methyl-5-(trans-1,5-dimethyl-2-pyrrolidinyl)-isoxazole oxalate 25 a. 3-Methyl-5-(trans-1,5-dimethyl-2-pyrrolidinyl)-isoxazole Methyl lithium (1.57 mL, 1.40 M, 2.2 mmol) was added dropwise to a cooled ($-78°$ C.) solution of 3-methyl-5-(1-methyl-.5-oxo-2-pyrrolidinyl)-isoxazole (22c, 360.0 mg, 2.0 mmol) in diethyl ether (8.0 mL). The resulting mixture was slowly warmed to 0° C., and stirred at the same temperature for twenty minutes. The solution was then warmed to room temperature and stirred for 1.5 hr. A lithium aluminum hydride solution (2.20 mL, 1.0 M, 2.20 mmol) was added dropwise to the mixture and the mixture was stirred at room temperature for two hours. The mixture was then cooled to 0° C., and methanol (2.0 mL) was added to decompose the aluminum salts. After evaporation of the solvents, the residue was purified twice on silica gel eluting with $CHCl_3$/MeOH (40:1 and 20:1) to give 156.7 mg (44% yield) of the title compound (25a). TLC $R_f=0.46$ ($CHCl_3$:MeOH=20:1). MS ($DCl/NH_3$) m/e 181 $(M+H)^+$. $^1H$ NMR ($CDCl_3$) δ: 1.14 (d, J=6.0 Hz, 3H, $CH_3$), 1.54–1.65 (m, 1H), 1.86–1.97 (m, 1H), 2.24 (s, 3H, $ArCH_3$), 2.29 (s, 3H, $NCH_3$), 2.18–2.38 (m, 2H), 2.97–3.06 (m, 1H, NCH), 4.25–4.32 (m, 1H, NCHAr), 5.94 (s, 1H, ArH).

25 b. 3-Methyl-5-(trans-1,5-dimethyl-2-pyrrolidinyl)-isoxazole oxalate salt

A solution of oxalic acid (19.8 mg, 0.22 mmol) in diethyl ether was added dropwise to a stirring solution of 3-methyl-5-(trans-1,5-dimethyl-2-pyrrolidinyl)-isoxazole (25a, 36.0 mg, 0.20 mmol)in diethyl ether. After 30 minutes of stirring, the diethyl ether was decanted off and the resulting precipitate was triturated several times with diethyl ether to give, after evaporation of the solvent in vacuo, 56.2 mg of the title compound (25).

EXAMPLE 26

3-Methyl-5-(trans-1-methyl-4-ethyl-2-pyrrolidinyl)-isoxazole oxalate

Following the procedure of Example 24, a sample of 3-methyl-5-(1-methyl-5-oxo-2-pyrrolidinyl)-isoxazole from Example 22c, is reacted with ethyl iodide to afford the title compound.

EXAMPLE 27

3-Bromo-5-(1-methyl-2(S)-pyrrolidinyl)-isoxazole hydrochloride 27 a. -3-Bromo-5-(1-BOC-2(S)-pyrrolidinyl)-isoxazole A 7.151 g (36.62 mmol) sample of (2S)-ethynyl-N-t-butyloxycarbonyl-pyrrolidine (from Example 1 c above) was dissolved in 200 mL of ethyl acetate, and 22 mL of water, 18.46 g (219.7 mmol) of NaHCO$_3$, and 14.80 g (72.9 mmol) of dibromoformaldoxime (prepared according to Vyas et al., Tett. Lett., 25:487-490 (1984)), and the mixture was stirred at room temperature for 90 hr. The mixture was diluted with 100 mL of ethyl acetate, and washed with water and brine, then the solvent was dried over MgSO$_4$ and evaporated to leave the crude product as a brown oil. The residue was purified by flash chromatography over silica gel, eluting with 1:6 ethyl acetate :hexane. Removal of the solvent gave 8.998 g of the title product as a yellow oil (77.5% yield). MS m/e: 278, 280 (M-C$_4$H$_9$+NH$_4$)$^+$, 317, 319 (M+H)$^+$, 334, 336 (M+NH$_4$)$^+$. NMR (CDCl$_3$) δ: 1.36, 1.46 (two singlets, 9H), 1.94-2.35 (m, 4H), 3.4-3.6 (m, 2H), 4.92-5.06 (two broad doublets, 1H), 6.13, 6.19 (two singlets, 1H).

27 b. 3-Bromo-5-(1-methyl-2(S)-pyrrolidinyl)-isoxazole

A 263 mg (0.829 mmol) sample of 3-bromo-5-(1-BOC-2(S)-pyrrolidinyl)-isoxazole (from Example 27 step a above) was dissolved in 2 mL of formic acid, and 5 mL of 37% aqueous formalin was added. The solution was heated at reflux for 1.5 hr, then 15 mL of 10% HCl was added, and the mixture was extracted twice with ethyl acetate. The aqueous residue was adjusted to pH 8 with solid NaHCO$_3$, and the solution was extracted twice with methylene chloride. The extract was dried over MgSO$_4$, and the solvent was removed to leave the crude product 157 mg (82% yield) as a colorless oil.

27 c. 3-Bromo-5-(1-methyl-2(S)-pyrrolidinyl-isoxazole hydrochloride

The product of Example 27 step b was converted to the HCl salt by the procedure given in Example 16b above, to give 118 mg of the title product MS (m/e): 231, 233 (M+H)$^+$. Calc for C$_8$H$_{11}$N$_2$OBr.HCl.0.5H$_2$O: C, 34.74; H, 4.74; N, 10.13; Found: C, 34.76; H, 4.45; N, 10.06. $^1$H NMR (D$_2$O) δ: 2.22-2.5 (m, 3H), 2.55-2.7 (m, 1H), 2.94 (s, 3H), 3.37 (m, 1H), 3.77 (m, 1H), 4.80 (m, 1 H, under D$_2$O peak), 6.97 (s, 1H).

EXAMPLE 28 trans-5-(1-ethyl-4-methyl-2(S)-pyrrolidinyl)-3-methyl-isoxazole and
trans-5-(1,4-dimethyl-2(S)-pyrrolidinyl-3-methyl-isoxazole 28 a 3-methyl-5-(1,4-dimethyl-5-oxo-2(S)-pyrrolidinyl)-isoxazole A 350 mg (1.88 mmol) sample of 3-methyl-5-(1-methyl-5-oxo-2(S)-pyrrolidinyl)-isoxazole (from Example 22c above) was dissolved in 10 mL of THF, and the solution was cooled to −78° C. To this solution was added 1.5 mL of LDA (2.26 mmol), then 0.35 mL of methyl iodide, and the reaction was stirred for 1 hr at −78° C. and for 2 hr as the reaction was warmed to room temperature. Excess methanol was added, and the mixture was extracted with chloroform. The solvent was dried, filtered and concentrated, and the residue was purified by flash chromatography, eluting with 10:1 chloroform:methanol.

28 b
trans-5-(1-ethyl-4-methyl-2(S)-pyrrolidinyl)-3-methyl-isoxazole

A 120 mg sample of 3-methyl-5-(1,4-dimethyl-5-oxo-2(S)-pyrrolidinyl)-isoxazole, from step a above, was dissolved in 5 mL of THF, and 1.86 mL of BH$_3$ (1M in THF was added). The reaction was stirred at reflux for 2 hr, cooled, quenched by addition of methanol, then stirred for 30 min at room temperature. The solvent was evaporated, and the residue was dissolved in ethanol, CsF was added, and the mixture was stirred at 40° C. for 16 hr. The solvent was removed, and the residue was chromatographed on silica gel. Of the fractions isolated by chromatography, the minor product was trans-5-(1-ethyl-4-methyl-2(S)-pyrrolidinyl)-3-methyl-isoxazole compound, of which 19 mg was isolated and carried to the next step; the major product was the trans-5-(1-methyl-4-methyl-2(S)-pyrrolidinyl)-3-methyl-isoxazole, of which 54 mg was isolated and taken to step d, below.

28 c trans-5-(1-ethyl-4-methyl-2(S)-pyrrolidinyl)-3-methyl-isoxazole hydrochloride The product of 28 step b was converted to the HCl salt by the procedure given in Example 16b. MS m/e: 195 (M+H)$^+$, 212 (M+NH$_4$)$^+$. $^1$H NMR (D$_2$O) δ: 1.20 (d, 3H, J=6.6 Hz), 1.25 (t, 3H, J=7.7 Hz), 2.19-2.33 (m, 1H), 2.55-2.65 (m, 1H), 2.70-2.78 (m, 3H), 2.92 (s, 3H), 2.96 (q, 1H, J=10 Hz), 3.86 (dd, 1H, J=7, 12 Hz), 4.88 (t, 1H, J=8.7 Hz), 6.88 (s, 1H). Calc for C$_{11}$H$_{18}$N$_2$O.HCl.0.25 CHCl$_3$; C, 51.85; H, 7.22; N, 10.75; Found: C, 51.60; H, 7.22; N, 10.47.

28 d. trans-5-(1-methyl-4-methyl-2(S)-pyrrolidinyl)-3-methyl-isoxazole hydrochloride The product of 28 step b was converted to the HCl salt by the procedure given in Example 16b. MS m/e: 181 (M+H)$^+$, 198 (M+NH$_4$)$^+$. $^1$H NMR (D$_2$O) δ: 1.25 (d, 3H, J=5 Hz), 2.17 (m, 1H), 2.36 (s, 3H), 2.56 (m, 1H), 2.81(s, 3H), 3.10(m, 1H), 4.10 (m, 1 H),4.36 (m, 1H), 7.05 (s, 1H). Anal. calcd. for C$_{12}$H$_{18}$N$_2$O$_5$.HCl.0.1-H$_2$O: C, 54.97; H, 7.93; N, 12.82; Found: C, 54.77; H, 8.12; N, 12.78.

EXAMPLE 29

5-(1-methyl-2(S)-pyrrolidinyl)-3-methoxy-isoxazole 29 a. 5-(1-methyl-2(S)-pyrrolidinyl)-3-methoxy-isoxazole A 260 mg (1.125 mmol) sample of 3-bromo-5-(1-methyl-2(S)-pyrrolidinyl)-isoxazole, from Example 27 step b above, was dissolved in 10 mL of methanol, and 4 mL of 40 % KOH was added, and the mixture was heated at reflux for 150 hr. The methanol was removed by evaporation, 25 mL of water was added, and the mixture was extracted with methylene chloride. The extract was dried over MgSO4 and concentrated.

20 a. 5-(1-methyl-2(S)-pyrrolidinyl-3-methoxy-isoxazole hydrochloride

The product of step a was convened to the HCl salt by the procedure given in Example 16b. MS m/e: 183 (M+H)$^+$, 200 (M+NH$_4$)$^+$. $^1$H NMR (D$_0$O) δ: 2.27-2.35 (m, 1H), 2.35-2.45 (m, 1H), 2.55-2.65 (m, 1H), 2.93 (s, 3H), 3.36-3.42 (m, 1H), 3.74-3.76 (m, 1H), 3.99 (s, 3H), 4.65-4.75 (m, 1H), 6.47 (s, 1H). Calc for C$_9$H$_{14}$N$_2$O$_2$.HCl.0.2H$_2$O: C, 48.63; H, 6.98; N, 12.60; Found: C, 48.57; H, 6.94; N, 12.54.

EXAMPLE 30

3-Methyl-5-(trans-1-methyl-5-fluoromethyl-2-pyrrolidinyl)-isoxazole oxalate

The product of example 23a is reacted under anhydrous-inert conditions with the ylide, derived from methoxymethyltriphenylphosphonium bromide (Aldrich), to convert the compound into the 3-methyl-5-(1-methyl-5-methoxymethylene-2-pyrrolidinyl)-isoxazole, which is hydrolyzed to the 3-methyl-5-(1-methyl-5-formyl-2-pyrrolidinyl)-isoxazole with mild acid. The aldehyde is then reduced to the 3-methyl-5-(1-methyl-5-hydroxymethyl-2-pyrrolidinyl)-isoxazole by treatment with sodium borohydride in ethanol. The 5'-hydroxymethylisoxazole is reacted with methanesulfonyl chloride, the resulting mesylate compound is reacted with tetrabutylammonium fluoride, and the resulting product is converted to the oxalate salt to afford the title compound.

EXAMPLE 31

3-Methyl-5-)trans-1-methyl-3-fluoromethyl-2-pyrrolidinyl)-isoxazole oxalate

3-Methyl-5-formyl-isoxazole (prepared following the procedure of Tetrahedron Lett., (32), 2961-4, 1979) is reacted with methylamine and succinic anhydride to provide 3-methyl-5-(1-methyl-3-carboxy-5-oxo-2-pyrrolidinyl)-isoxazole. This acid is converted to the ester and then selectively reduced with sodium borohydride to give the corresponding alcohol, which is reacted with methanesulfonyl chloride. The resulting mesylate is converted to the fluoromethyl isoxazole by treatment with tetrabutylammonium fluoride. Following the procedure of Example 24b, the 3-methyl-5-(1-methyl-3-fluoromethyl-5-oxo-2-pyrrolidinyl)-isoxazole is reacted with borane, and the resulting product is converted to the oxalate salt to afford the title compound.

EXAMPLE 32

3-trifluoromethyl-5-(1-methyl-2(S)-pyrrolidinyl)-isoxazole, hydrochloride 32 a. 3-trifluoromethyl 5-(1'-t-butyloxycarbonyl-2'(S)-pyrrolidinyl)-isoxazole To a solution of the product of Example 1c (200 mg, 1.02 mmoL) in toluene (10 mL) was added solid $K_2CO_3$ (414 mg, 3.00 mmoL) followed by freshly prepared (trifluoroacetyl) hydroximoyl chloride [W. J. Middleton, *J. Org. Chem.*, (1984), 49, 919–922] (295 mg, 2.00 mmoL), and the reaction mixture brought to reflux. After refluxing for ~20 hours a second aliquot of $K_2CO_3$ (~450 mg) and (trifluoroacetyl)hydroximoyl chloride (592 mg, 4.01 mmoL) were added and refluxing was continued for an additional 7 hours. The reaction mixture was then diluted with $Et_2O$ (50 mL) and washed with 20-mL portions of sat aq. $NaHCO_3$, 10% aq. citric acid and brine, then dried ($MgSO_4$) and concentrated to afford the crude product as an oil. Chromatographic purification (silica, EtOAc/Hex 1:6) afforded the pure isoxazole as a pale yellow oil (130 mg, 41% yield). $^1$H-NMR (CDCl$_3$) δ: 6.35,6.29 (two br s, 1H); 5.11, 4.99 (two br s, 1H); 3.66–3.37 (br m, 2); 2.43–1.94 (br m, 4H); 1.47, 1.34 (s, 9H). MS(Cl) m/e 307 $(M+H)^+$, 324 $(M+NH_4)^+$.

32 b. 3-trifluoromethyl-5-(1-methyl-2(S)-pyrrolidinyl)-isoxazole, hydrochloride

To a solution of 3-trifluoromethyl 5-(1-t-butyloxycarbonyl-2-pyrrolidinyl)-isoxazole (37 mg, 0,121 mmoL) (Example 35a) in $CH_2Cl_2$ (4 mL) was added trifluoroacetic acid (2 mL). After stirring at room temperature for 45 minutes the solvents were evaporated in vacuo to afford the crude amine. To this material was added 37% aqueous formalin (2 mL) and formic acid (0.5 mL) and the mixture was refluxed for 2 hours, then stirred at room temperature for 16 hours. The reaction mixture was then diluted with 10% aq. HCl (~6 mL)and extracted with $Et_2O$ (3×15 mL). Then the aqueous layer was basified with sat. aq. $K_2CO_3$ and extracted with $CH_2Cl_2$ (3×15 mL). The combined $CH_2Cl_2$ layers were dried ($MgSO_4$) and concentrated to afford the crude product as an oil. This material was dissolved in $Et_2O$ (5 mL) and 1M ethereal HCl (1 mL) was added to afford, after concentration, the product as a hygroscopic solid (23 mg, 73% yield). $^1$H-NMR ($D_2O$) δ : 7.28 (s,1H); 3.85 (br s,1H); 3.47 (br s, 1H); 3.02 (b s,4 H); 2.74 (m, 1H); 2.60–2.46 (m, 1H); 2.43–2.28 ( MS(Cl) m/e 221 $(M+H)^+$, 238 $(M+NH_4^+)$.

EXAMPLE 33

3.4-Dimethyl-5-(1-methyl-2-pyrrolidinyl)-isoxazole hydrochloride

Following the procedure of Example 36, except substituting methyl iodide for the benzyl bromide of step c therein, the title compound is prepared.

EXAMPLE 34

5-(2-pyrrolidinyl)-isoxazole oxalate

N-Carbobenzyloxyproline methyl ester is reacted under anhydrous-inert conditions with the dilithium anion of aldoxime in a manner similar to that described in Example 22c. The β-keto oxime is treated with methanesulfonyl chloride in the presence of triethylamine to produce the amino protected isoxazole. Hydrogenation in the presence of palladium on carbon catalyst and conversion to the oxalate salt affords the title compound.

EXAMPLE 35

5-(1-methyl-2-pyrrolidinyl)-isoxazole oxalate

N-methylproline methyl ester is reacted under anhydrous-inert conditions with the dilithium anion of aldoxime in a manner similar to that described in Example 22c. The β-keto oxime is treated with methanesulfonyl chloride in the presence of triethylamine to produce the isoxazole. Conversion to the oxalate salt affords the title compound.

EXAMPLE 36

3-methyl-5-(1-methyl-2(S)-pyrrolidinyl)-4-(phenylmethyl-isoxazole hydrochloride 36 a. Proline Methyl Ester, Hydrochloride Salt To a suspension of (L)-proline (57.55 g, 500 mmoL)in methanol (500 mL) at 0° C. was added thionyl chloride (40.1 mL, 550 mmoL) dropwise over a 45 minute period, then the reaction mixture was slowly allowed to warm to room temperature. After 22 hours the solvent was removed in vacuo, and the resultant oil was placed under high vacuum to afford the product as a white solid. This material was redissolved in methanol (~500 mL) and re-concentrated to afford the title compound as a white, hygroscopic solid (81.35 g, 99%). MS (DCl/NH$_3$) m/e 130 $(M+H)^+$, 147 $(M+NH_4)^+$; $^1$H-NMR )D$_2$O) δ: 2.02–2.15 (m, 2H); 2.15–2.24 (m, 1H); 2.39–2.49 (m, 1H); 3.34–3.48 (m, 2H); 3.85 (s, 3H, OMe); 4.50 (dd, 1H).

36 b. N-Methyl Proline Methyl Ester

To a methanolic (250 mL) solution of L-proline methyl ester HCl (10.42 g, 62.92 mmol, from step a above), sodium acetate trihydrate (8.6 g, 63.2 mmoL) and 37 wt % aqueous formaldehyde (20 mL) was added 10% Pd/C (1.05 g), and the reaction mixture was placed under 4 atmosphere $H_2$ pressure. Upon completion of the reaction the catalyst was removed by filtration, the methanolic solution concentrated, and the residue was dissolved in 10% aq. HCl (~60 mL) and washed with ether (3×100 mL). The aqueous layer was basified with $K_2CO_3$ (solid) to pH ~12 and extracted with $CH_2Cl_2$ (3×75 mL) The combined $CH_2Cl_2$ layers were dried ($MgSO_4$) and concentrated to afford the crude product as a clear oil (7.19 g, 80%). MS ($DCl/NH_3$) m/e (M+H)+, $^1$H-NMR ($CDCl_3$) δ: 1.78–2/03 (m, 3H); 2.13–2.21 (m, 1H); 2.29–2.38 (m, 1H); 2.42 (s, 3H); 2.97–3.02 (dd, 1H): 3.13–3.19 (m, 1H); 3.75 (s, 3H).

36 c. 1-(1-methyl-2-pyridinyl)-2-(phenylmethyl)-1,3-butanedione-3-oxime

To a solution of 2.0 g (27.2 mmol) of acetone oxime (Aldrich Chemical Co.) in 75 mL of THF stirred under $N_2$ at 0° C. was added dropwise 36 mL (57.2 mmol) of n-butyl lithium, and the reaction was stirred for 1 hr. Next was added 3.6 mL (30 mmol) of benzyl bromide in 10 mL of THF, and the reaction was stirred for 0.5 hr at 0° C. and 0.5 hr at room temperature. The reaction was cooled to 0° C. again, another 19 mL of n-butyl lithium was added dropwise, and the reaction was stirred at 0° C. for 1 hr. Next was added dropwise a solution of 4.30 g (30 mmol) of N-methyl-L-proline methyl ester, from step b above, and the reaction was stirred at room temperature for 16 hr. The reaction solution was added via syringe to a vigorously stirred 15% aqueous HCl solution cooled to 0° C. The mixture was then washed with ether, and NaOH was added the aqueous layer to adjust the pH to 12–13. This basic solution was extracted with ethyl acetate, and the extract was washed with brine and dried over $Na_2SO_4$. Removal of the solvent and purification of the residue by flash chromatography on silica gel, eluting with 70:30 ethyl acetate:hexane gave 2 g of the title product. MS m/e: 257 (M-OH)+, 275 (M+H)+. $^1$H NMR ($CDCl_3$) δ: 1.55–1.75 (m, 3H), 1.70 (s, 3H), 1.75–1.90 (m, 1H), 2.40–2.55 (m, 2H), 2.58–2.65 (m, 1H), 2.60 (s, 3H), 2.75–2.90 (m, 1H), 3.05–3.30 (m, 2H), 7.15–7.35 (m, 5 H).

36 d. L-3-methyl-5-(1-methyl-2-pyrrolidinyl)-4-phenylmethyl-isoxazole hydrochloride A 1.60 g sample of the oxime from step c above was dissolved in 50 mL of ethanol saturated with HCl and heated at reflux for 16 hr. The solvent was removed, and to the residual oil was added satd. $NaHCO_3$, and the mixture was extracted with ether. The extract was dried over $Na_2SO_4$ and concentrated to give an oily product, which was converted to the HCl salt by the procedure given in Example 16. The title product (1.38 g) was obtained as a hygroscopic solid. MS: 257 (M+H)+. $[\alpha]_D = +26.5°$ (c=0.52, methanol, 25° C.). $^1$H NMR ($D_2O$) δ: 2.20 (s, 3H), 2–22–2.49 (m, 4H), 2.69 (s, 3H), 3.26–3.34 (m, 1H), 3.73–3.81 (m, 1H), 3.93 (d, 2H, J=4 Hz), 4.63 (t, 1H, J=11 Hz), 7.23–7.44 (m, 5H). Calc for $C_{16}H_{20}N_2O.0.3HCl.0.1H_2O$: C, 62.90; H, 7.09; N, 9.17; Found: C, 62.87; H, 6.97; N, 9.14.

EXAMPLE 37

3-methyl-5-(1-methyl-2(S)-pyrrolidinyl)-4-ethyl-isoxazole hydrochloride 37 a. 1-(1-methyl-2(S)-pyridinyl)-2-ethyl-1,3-butanedione-3-oxime Following the procedure of Example 36 step a, substituting ethyl iodide for the benzyl bromide, the title compound was prepared. MS: 195 (M−OH)+, 213 (M+H)+. $^1$H NMR ($CDCl_3$) δ: 1.07 (t, 3H, J=7.5 Hz), 1.60–1.95 (m, 6H), 1.97 (d, 3H, j=1 Hz),2.44–2.53 (m, 1H), 2.58 (s, 3H), 2.60–2.64 (m, 1H), 2.68–2.73 (m, 1H), 3.14–3.18 (m, 1H), 37 b. 3-methyl-5-(1-methyl-2(S)-pyrrolidinyl)-4-ethyl-isoxazole hydrochloride Following the procedure of Example 36 step b, substituting the compound from step a above, the title compound was prepared. MS: 195 (M+H)+. $[\alpha]_D = -11.6°$ (c=0.53, methanol, 25° C.). $^1$H NMR ($D_2O$) δ: 1.14 (t, 3H, J=8 Hz), 2.27–2.57 (m, 6H), 2.32 (s, 3H), 2.83 (s, 3H), 3.33–3.42 (m, 1H), 3.77–3.82 (m, 1H), 4.77–4.83 (m, 1H), Calc for $C_{11}H_{18}N_2O.0.2C_2H_5OH$: C, 55.38; H, 8.32; N, 11.33; Found: C, 55.42; H, 8.27; N, 11.07.

EXAMPLE 38

(R)-3-methyl-5-(2-piperidinyl)-isoxazole hydrochloride 38 a. (R)-N-(t-butyloxycarbonyl)-pipecolinic acid A 10.44 g (80.9 mmol) sample of (R)-pipecolinic acid, previously resolved according to Hemingway,R. J., J. Pharm. Pharmac., 20, 87–91, (1968), was dissolved in 70 mL of dioxane and 40 mL of $H_2O$, and 40 mL of 1M $K_2CO_3$ and 39 mL of di-t-butyldicarbonate were added. The reaction was stirred at room temperature for 16 hr, then an additional 10 mL of di-t-butyldicarbonate and 40 mL of 1M $K_2CO_3$ were added and the reaction continued for another 24 hr. The solvents were removed on a rotary evaporator, 10% citric acid solution was added to the residue, and the mixture was extracted with $CHCl_3$. The extract was dried over $MgSO_4$, filtered and concentrated to give the title product as a white solid. MS: 247 (M+$NH_4$)+, 230 (M+H)+, 191 (M-$C_4H_8$+$NH_4$)+.

38 b (R)-N-(t-butyloxycarbonyl)-pipecolinic acid methyl ester

A 10.83 g (47.29 mmol) sample of (R)-N-(BOC)-pipecolinic acid, from step a above, was dissolved in 50 mL of THF, cooled to 0° C. and placed under $N_2$ atmosphere. To this solution was added 5.2 mL (47.29 mmol) of N-methylmorpholine and 6.134 g (47.29 mmol) of isobutyl chloroformate, and the mixture stirred for 20 min. Excess methanol was added, and the reaction was stirred, gradually warming to room temperature, for 16 hr. The solvents were reduced on a rotary evaporator to leave a slurry, which was dissolved in ethyl acetate. The solution was washed with 10% $KHSO_4$ and satd. $K_2CO_3$, dried ($MgSO_4$), filtered and evaporated to dryness. The residue was purified by flash chromatography on silica gel, eluting with 4:1 hexane:ethyl acetate, to afford 5.636 g of the title product after removal of the solvent. MS: 244 (M+H)+, 261 (M+$NH_4$)+.

38 C. 1-(1-(t-butyloxycarbonyl)-2(R)-piperidinyl)-1,3-butanedione-3-oxime

To a solution of 903 mg (12.3 mmol) of acetone oxime (Aldrich Chemical Co.)in 10 mL of THF stirred under $N_2$ at 0° C. was added dropwise 9.9 mL (24.7 mmol) of n-butyl lithium, and the reaction was stirred for 1.5 hr. To this solution was added a THF solution of the ester from step b above, and the reaction was stirred for 16 hr at room temperature. The reaction was quenched with satd. $NH_4Cl$, and the volatiles were removed under reduced pressure. The residue was slurried in satd. $NH_4Cl$, and the mixture was extracted with ethyl acetate. The extract was dried over $MgSO_4$, filtered and concentrated under reduced pressure to give an orange oil which solidified upon standing. MS :267 (M-OH)+.

38 d. 5-(N-(t-butyloxycarboyl)-2(R)-piperidinyl)-3-methyl-isoxazole

A 2.18 g (7.7 mmol) sample of the oxime from step c above was dissolved in 7 mL of THF and stirred under N2. To this solution was added 0.56 mL (7.44 mmol) of methanesulfonyl chloride, and the reaction was stirred for 15 min, after which 1.04 mL of triethylamine (7.44 mmol) was added in small portions. The reaction was stirred for 7 hr, an additional 0.1 mL of triethyl amine was added, and the reaction was stirred for 16 hr. The solvents were removed by evaporation under reduced pressure, and the residue was suspended in satd $K_2CO_3$. This mixture was extracted with ethyl acetate, and the extract was washed with 10% $KHSO_4$ and water. This crude product was purified by flash chromatography on silica gel, eluting with 4:1 hexane:ethyl acetate. MS 267$(M+H)^+$, 284 $(M+N H_4)^+$. NMR showed the nitrogen protecting group to contain a mixture of the t- and i-butyl isomers.

38 e. 3-methyl-5-(2(R)-piperidinyl)-isoxazole

A 317 mg sample of the BOC-protected compound from step d was dissolved in 1.5 mL of methylene chloride and 1.5 mL of trifluoroacetic acid, and the reaction was stirred at room temperature for 16 hr. The reaction was quenched by addition of excess satd $K_2CO_3$ solution, and the mixture was extracted with chloroform. The extract was dried over $MgSO_4$, filtered and concentrated. The residue was purified by flash chromatography on silica gel, eluting with 800:10:2 chloroform:methanol:$NH_4OH$, to afford 48.1 mg of the title product. MS: 167 $(M+H)^+$, 184 $(M+NH_4)^+$.

38 f. 3-methyl-5-(2(R)-piperidinyl)-isoxazole hydrochloride

Following the procedure of Example 10d, substituting the compound from step 38e above, 36 mg of the title compound was prepared. mp 131°-2° C. MS: 167$(M+H)^+$, 184 $(M+NH_4)^+$. $^1$H NMR $(D_2O)$ δ: 1.63-1.83 (m, 2H), 1.95-2.08 (m, 4H), 2.25-2.32 (m, 1H), 2.32 (s, 3H), 3.18 (dt, 1H, J=3, 13 Hz), 3.48-3.54 (br d, 1H, J=13 Hz), 4.58 (dd, 1H, J=4, 13 Hz). Calc for $C_9H_{14}N_2O\cdot HCl$: C, 53.33; H, 7.96; N, 13.82; Found: C, 53.08; H, 7.56; N, 13.88.

EXAMPLE 39

3-methyl-5-(1-methyl-2(R)-piperidinyl)-isoxazole hydrochloride

A 348.6 mg (1.31 mmol) sample of 5-(N-(t-butyloxycarbonyl)-2(R)-piperidinyl)-3-methyl-isoxazole, from Example 38d above, was dissolved in 2 mL of formaldehyde and 1 mL of formic acid and heated at 90° C. for 16 hr. The solution was concentrated under vacuum, excess 10% $KHSO_4$ was added, the mixture was washed with ethyl acetate, solid $K_2CO_3$ was added, and the basic mixture extracted with $CHCl_3$. The extract was dried over $MgSO_4$, filtered and concentrated. The residue was treated according to the procedure of Example 10d, to form the salt, which was precipitated from ethanol, triturated with ether and dried. MS: 181 $(M+H)^+$, 198 $(M+NH_4)^+$. $^1$H NMR $(D_2O)$ δ: 1.60-1.75 (m, 1H), 1.80-2.25 (m, 5H), 2.33 (s, 3H), 2.69 (s, 3H (br t, 1 H, J=12 Hz), 3.61 br d, 1H, J=12 Hz), 4.53 (br, 1H), 6.60 (s, 1H). Anal $C_{10}H_{16}N_2O\cdot HCl$: C, 55.42; H, 7.90; N, 12.93; Found: C, 55.17; H, 8.02; N, 12.89.

EXAMPLE 40

3-methyl-5-(2(S)-piperidinyl)-isoxazole hydrochloride

Following the procedures of Example 38, substituting a 8.1 g (62.79 mmol) sample of (S)-pipecolinic acid (resolved according to Hemingway, R. J., J. Pharm. Pharmac., 20, 87-91, (1968)) for the (R)-pipecolinic acid of step a therein, to give the title product. mp 156°-159° C. (dec). MS: 167$(M+H)^+$, 184 $(M+NH_4)^+$. $^1$H NMR $(D_2O)$ δ: 1.67-1.82 (m, 2H), 1.94-2.06 (m, 4H), 2.25-2.3 (m, 1H), 2.32 (s, 3H), 3.18 (dt, 1H, J=3, 13 Hz), 3.48-3.55 (br d, 1H, J=13 Hz), 4.58 (dd, 1H, J=4, 13 Hz) 6.49 (s, 1H). Anal. Calc for $C_9H_{14}N_2O\cdot 1.1$ HCl: C, 52.89; H, 7.38; N, 13.58; Found: C, 52.67; H, 7.17; N, 13.53.

EXAMPLE 41

3-methyl-5-(2(S)-azetidinyl)-isoxazole hydrochloride 41 a. 1-(t-butyloxycarbonyl)-azetidine-2-carboxylic acid A 10.15 g (100.39 mmol) sample of (S)-azetidine-2-carboxylic acid (Fluka) was dissolved in 300 mL of 1:1 $H_2O$: dioxane and stirred under $N_2$. To this solution was added 12.64 mL (115 mmol) of N-methylmorpholine (NMM), and the solution was cooled to 0° C. To the cooled solution was slowly added 29.98 mL (130 mmol) of di-t-butyl dicarbonate, and the reaction mixture was allowed to warm to room temperature and stirred for 16 hr. An additional 10 mg of di-t-butyl dicarbonate was added and the reaction was stirred for 2 hours longer. The reaction was quenched by pouring it into 250 mL of satd aqueous $Na_2CO_3$, and the mixture was washed with ethyl acetate. The aqueous solution was adjusted to pH 2 with 10% citric acid and 3M HCl and extracted with ethyl acetate. The extracts were dried over $Na_2SO_4$ and the solvent was removed under vacuum to give the title product as a white solid. MS: 21 9 (m, 2$(M+NH_4)^+$, $(M+H)^+$. $^1$H NMR $(CDCl_3)$ δ: 1.48 (s, 9H), 2.4-2.6 (b, 2H), 3.88=3.98 (m, 2H), 4.80 (b, 1H).

41 b. 1-(t-butyloxycarbonyl)-azetidine-2-carboxylic acid methyl ester

A 4.9 g (24.37 mmol) sample of 1-BOC-azetidine-2-carboxylic acid, from step a above, was dissolved in 35 mL of THF, and stirred under N2 at −10° C. To this solution was added 2.68 mL of NMM, and the mixture was stirred for 5 min. Next was added 3.16 mL (24.37 mmol) of isobutyl chloroformate, and the reaction was stirred for 20 min. To the reaction was next added 0.99 mL of methanol, and the stirred mixture was warmed to room temperature and stirred for 16 hr. The reaction was adjusted to an acidic pH and extracted with ethyl acetate. The solvent was removed, and the residue was purified on silica gel, eluting with 2:1 hexane:ethyl acetate to give 2.00 g of the title product. MS: 177 (M-$C_4H_8$+$NH_4)^+$, 216 $(M+H)^+$, 233 $(M+NH_4)^+$. $^1$H NMR $(CDCl_3)$ δ: 1.42 (s, 9H), 2.15-2.25 (m, 1H), 2.45-2.55 (m, 1H), 3.78 (s, 3H), 3.85-3.95 (m, 1H), 4.00-4.10 (m, 1H), 4.61 (dd, 1H, J=5, 10 Hz).

41 c 1-(1-(t-butyloxycarbonyl)-2-azetidinyl)-1,3-butanedione-3-oxime

Acetone oxime (749 mg, 10.18 mmol) was stirred in THF under $N_2$ at 0° C., and 8.14 mL (20.35 mmol) of n-butyllithium was added. A precipitate formed and the mixture was stirred for 1.5 hr. To this mixture was added 1.09 g (5.09 mmol) of 1-BOC-azetidine-2-carboxylic acid methyl ester, from step b above, and the reaction was stirred at 0° C. for 2.5 hr. The reaction was quenched with satd $NH_4Cl$, and the mixture concentrated to a slurry. Additional satd $NH_4Cl$ was added, and the mixture was extracted with ethyl acetate. The organic extract was washed with brine, dried over $MgSO_4$ and concentrated. The residue was taken to the next step without further purification. MS: 200 (M-$C_4H_8)^+$.

41 d. (S)-5-(1-(t-butyloxycarbonyl)-2-azetidinyl)-3-methyl-isoxazole

A 1.268 g (4.96 mmol) sample of the 1-(1-(t-butyloxycarbonyl)-2-azetidinyl)-1,3-butanedione-3-oxime, from step c above, was dissolved in 6 mL of THF, and 420 mg of methanesulfonyl chloride and 0.76 g of triethylamine were added. The reaction was stirred for 10 hr, 5 additional portions (ca 1 eq. each) of the chloride and amine were added, and the reaction was stirred for 16 hr. The solvents were removed under vacuum, and the residual slurry was dissolved in ethyl acetate and washed with solutions of $NaHCO_3$ and $Na_2CO_3$ and 10% citric acid. The solution was dried, filtered and concentrated to an oily residue. The residue was purified by flash chromatography on silica gel, eluting with 1:1 hexane:ethyl acetate. MS: 200 ($M-C_4H_8$)+, 256 ($M+NH_4$)+, 239 ($M+H$)+.

41 e. 3-methyl-5-(1-methyl-2(S)-azetidinyl)-isoxazole hydrochloride

The product of step d above (580 mg, 2.44 mmol) was deprotected according to the procedure of Example 1, step e. To the crude trifluoroacetate suspended in EtOH (10 mL) was added a catalytic amount of bromocresol green and the solution brought to pH 5.2 (green) with NaOAc. To the solution was added an excess of formaldehyde (37%, 1.3 mL), the solution stirred at room temperature for 30 min, and $NaBH_3CN$ (1.5 equivalents, 0.23 g) was added carefully maintaining the pH at 5.2 by the addition of HOAc or NaOAc. After 12 hr, the reaction was quenched by the addition of 10% $KHSO_4$ and the solvent was evaporated. The residue was dissolved in 10% $KHSO_4$, washed with EtOAc (3×40 mL) and made basic with saturated aqueous $K_2CO_3$. The aqueous solution was then extracted with $CHCl_3$ (4×40 mL), dried ($MgSO_4$), and the solvent removed in vacuo. The residue was purified by chromatography on silica (700:10:1.8 $CHCl_3$:MeOH:$NH_4OH$) and the free base was converted to the HCl salt by treatment with ethanolic HCl, according to the method of Example 10d above. The solvent was evaporated and the hydrochloride was recrystallized from $EtOH/Et_2O$ to yield 154.8 mg of the title compound: mp 116.5° C.; $[\alpha]_D$ −9.37(c0.5.5in $H_2O$, 26° C.); MS (Cl) m/e 153 ($M+H$)+, 170 ($M+NH_4$)+; $^1H$ NMR ($D_2O$) δ: 2.35 (s, 3H), 2.35–3.06 (m, 2H), 4.20 (br s, 2H), 4.73 (s, 3H), 5.64 (br t, 1H, J=10 Hz), 6.68 (s, 1H). Anal calcd. for $C_8H_{13}ClN_2O$: C, 50.93; H, 6.95; N, 14.85. Found: C, 50.95; H, 6.85; N, 14.76.

EXAMPLE 42

3-methyl-4-(1-methyl-2(S)-pyrrolidinyl)-1-phenyl-pyrazole hydrochloride 42 a. Proline methyl ester, hydrochloride Salt.

To a suspension of (L)-proline (57.55 g, 500 mmoL) in methanol (500 mL) at 0° C. was added thionyl chloride (40.1 mL, 550 mmoL) dropwise over a 45 minute period, then the reaction mixture was allowed to warm slowly to room temperature. After 22 hours the solvent was removed in vacuo and the resultant oil placed under high vacuum to afford the product as a white solid. This material was redissolved in methanol (∼500 mL) and re-concentrated to afford the title compound as a white, hygroscopic solid (81.35 g, 99%). MS (DCl/$NH_3$) m/e 130 ($M+H$)+, 147 ($M+NH_4$)+; $^1H$-NMR ($D_2O$) δ: δ: 2.02–2.15 (m, 2H); 2.15–2.24 (m, 1H), 2.39–2.49 (m, 1H), 3.34–3.48 (m, 2H); 3.85 (s, 3H, OMe); 4.50 (dd, 1H).

42 b. N-Methyl proline methyl ester

To a methanolic (250 mL) solution of L-proline methyl ester 10.42 g (62.92 mmol), sodium acetate trihydrate (8.6 g, 63.2 mmoL) and 37 wt % aqueous formaldehyde (20 mL) was added 10% Pd/C (1.05 g) and the reaction mixture placed under 4 atmosphere $H_2$ pressure. Upon completion of the reaction the catalyst was removed by filtration, the methanolic solution concentrated and the residue dissolved in 10% aq. HCl (∼60 mL) and washed with ether (3×100 mL), then the aqueous layer basified with $K_2CO_3$ (solid) to pH∼12 and extracted with $CH_2Cl_2$ (3×75 mL), then the combined $CH_2Cl_2$ layers dried ($MgSO_4$) and concentrated to afford the crude product as a clear oil (7.19 g, 80%). MS (DCl/$NH_3$) m/e ($M+H$)+, 1H-NMR ($CDCl_3$) δ: 1.78–2.03 (m, 3 H); 2.13–2.21 (m, 1H); 2.29–2.38 (m, 1 H); 2.42 (s, 3 H); 2.97–3.02 ( 3.13–3.19 (m, 1 H); 3.75 (s, 3 H).

42 c. 1-(1-methyl-2(S)-pyrrolidinyl)-1,3-butanedione-3-oxime

To n-butyllithium (Aldrich, 2.5M in hexane, 614 mL) diluted to 1.6M with hexane (342 mL) under Argon at 0° C. was added a solution of acetone oxime (56.15 g, 768 mmol, recrystallized from hexanes) in THF (500 mL) dropwise over a 90 minute period (butane evolved! ). After an additional 2 hours at 0° C. a solution of N-methyl proline methyl ester (50.0 g, 349 mmoL) in THF (75 mL) was added over a 90 minute period. After stirring an additional 20 hours at 0° C. the reaction mixture was slowly cannulated into a vigorously stirred solution of 10% aq. HCl (1700 mL, cooled to 0° C.) over a 40 minute period, then the layers separated and the aqueous layer washed with ether (1000 mL), then basified with $NaHCO_3$/$Na_2CO_3$ (solid) to pH ∼9–10 and extracted with $CH_2Cl_2$ (4×800 mL). The combined $CH_2Cl_2$ layers were dried ($MgSO_4$) and concentrated to afford the crude product as a pale yellow oil (53.62 g, 83% crude yield). MS (DCl/$NH_3$) m/e 185 ($M+H$)+; 1H-NMR ($CDCl_3$) δ:1.59–1.79 (m, 3), 2.00–2.07 (m, 1H); 2.02 (s, 3H, isoxazole Me); 2.43–2.52 (m, 1H); 2.57 (s, 3H), NMe); 2.77 (dd, 2H); 2.80 (d, 2H); 3.12–3.18 (m, 1H).

42 d. 3-methyl-5-(1-methyl-2(S)-pyrrolidinyl)-1-phenyl-pyrazole hydrochloride

A 0.55 g (3.0 mmol) sample of 1-(1-methyl-2-pyrrolidinyl)-1,3-butanedione-3-oxime, from step c above, and 1.30 g (9.0 mmol) of phenylhydrazine HCl were dissolved in 50 mL of absolute ethanol and heated at reflux for 3 hr. The solvent was evaporated, and the residue was dissolved in water. The solution was washed with ether, which was discarded, then adjusted to pH 14 with $K_2CO_3$ (solid) and extracted with ether. This extract was dried over $Na_2SO_4$ and evaporated to give 0.89 g of an oil, which was purified by flash chromatography, eluting with 5:95 methanol:methylene chloride. The free base was converted to the HCl salt by the procedure of Example 10d, and 0.2 g was obtained. $[\alpha]_D$= −3.7° (c=0.52, methanol, 25° C.). High resolution MS: theory, 242.1657; meas; 242.1650. $^1H$ NMR (DMSO) δ: 2.0–2.18 (m, 4H), 2.26 (s, 3H), 3.08–3.18 (m, 1H), 3.33 (s, 3H), 3.56–3.64 (m, 1H), 4.33–4.42 (m, 1H), 6.88 (s, 1H), 7.44–7.60 (m, 5H), 11.0 (br, 1H). Calc for $C_{15}H_{19}N_3$.1.1HCl.0.2$H_2O$: C, 63.21; H, 7.25; N, 14.74; found: C, 63.19; H, 7.35; N, 14.82.

EXAMPLE 43

3-methyl-5-(1-methyl-2(S)-pyrrolidinyl)-pyrazole hydrochloride

A 1.0 g (5.4 mmol) sample of 1-(N-methyl-2-pyrrolidinyl)-1,3-butanedione-3-oxime, from Example 42 step a above, and 1.10 g (16.2 mmol) of hydrazine HCl were dissolved in 50 mL of absolute ethanol and heated at reflux for 3 hr. The reaction was cooled and filtered, and the filtrate was concentrated. The residue was dissolved in 10% HCl and washed with methylene chloride. The aqueous layer was adjusted to pH 11-12 with solid $K_2CO_3$ and extracted with ether. The extract was dried over $Na_2SO_4$ and evaporated to give 0.72 g of crude product. The material was purified by flash chromatography on silica gel, eluting with 10:1 chloroform-:methanol, to give 0.48 g of the free base. The free base was dissolved in methylene chloride, and HCl in diethyl ether was added. The solvent was removed and the residue was dried to give 0.66 g of the title product. MS: 166 (M+H)+(free base). $^1$H NMR (DMSO) δ: 2.0-2.4 (m, 4H), 2.25 (s, 3H), 2.69, 2.70 (two s, 3H), 3.08-3.20 (m, 1H), 3.58-3.68 (m, 1H), 4.29-4.38 (m, 1H), 6.31 (s, 1H), 10.47 (br, 1H). Anal calc for $C_9H_{15}N_3.2.3HCl.0.2EtOH$: C, 43.71; H, 7.22; N, 16.27; found: C, 43.54; H, 7.30; N, 16.38.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

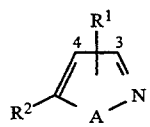
(I)

wherein

A is O, S, NH or N-phenyl;

$R^1$ is located at either position 3 or position 4 and is selected from the group consisting of, or $R^1$ is located at both positions 3 and 4 and is independently selected at each position from the group consisting of:

(i) hydrogen;
(ii) $C_1$-$C_6$-alkyl;
(iii) -$(CH_2)_aR^3$, wherein
   a is 1, 2, 3 or 4, and
   $R^3$ is $C_3$-$C_7$-cycloalkyl or phenyl;
(iv) —$(CH_2)_aOR^4$, wherein
   a is as defined above, and
   $R^4$ is $C_3$-$C_7$-cycloalkyl, phenyl or $C_1$-$C_6$-alkyl;
(v) —$(CH_2)_bNHR^4$, wherein
   b is 0, 1, 2, 3 or 4 and $R^4$ is as defined above;
(vi) $CF_3$;
(vii) halo;
(viii) halo-$C_1$-$C_6$-alkyl;
(ix) —$(CH_2)_aSR^4$, wherein a and $R^4$ are as defined above;
(x) OH;
(xi) —O—$C_1$-$C_6$-alkyl;
(xii) SH; and
(xiv) $NR^4R^4$, wherein $R^4$ is as defined above; and $R^2$ is selected from the group consisting of:

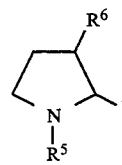
(i)

wherein
$R^5$ is H or $C_1$-$C_3$-alkyl, and
$R^6$ is H, F, $CH_2F$, CN, $NH_2$, $NHCO(C_1$-$C_6$-alkyl ), —$CH_2CH=CH_2$ or $CH_2OR^9$, wherein $R^9$ is $C_1$-$C_3$-alkyl or —$CH_2CH=CH_2$;

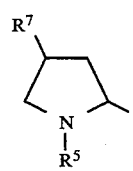
(ii)

wherein
$R^5$ is as defined above, and
$R^7$ is H, OH, $C_1$-$C_3$-alkyl, or trans-$CH_2F$;

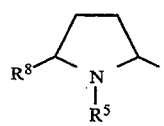
(iii)

wherein
$R^5$ is as defined above, and
$R^8$ is H, trans-$C_1$-$C_3$-alkyl, or trans-$CH_2F$;

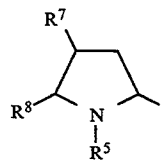
(iv)

wherein $R^5$, $R^7$ and $R^8$ are as defined above;

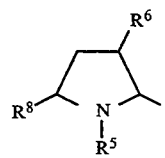
(v)

wherein $R^5$, $R^6$ and $R^8$ are as defined above;

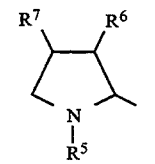
(vi)

wherein $R^5$, $R^6$ and $R^7$ are as defined above;

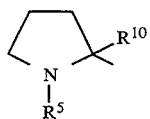

(vii)

wherein R[5] is as defined above, and R[10] is H or $C_1$–$C_3$-alkyl;

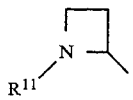

(viii)

wherein R[11] is $C_1$–$C_3$-alkyl; and

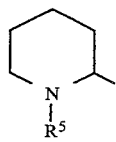

(ix)

wherein R[5] is defined above, and the stereochemistry at position 2 of formula (I) is (R) when R[5] is $C_1$–$C_3$-alkyl;

with the proviso that R[5] is $C_1$–$C_3$-alkyl when R[1] is $C_3$- or $C_4$-alkyl or —$(CH_2)_a$R[3];

or a pharmaceutically-acceptable salt thereof.

2. A compound according to claim 1, wherein R[1] is at position 3 of the ring and is H, halo, $C_1$–$C_6$-alkyl, $CF_3$ or —O—$C_1$–$C_6$-alkyl, and R[2] is selected from alternate definition (ii), wherein R[7] is H or $C_1$–$C_3$-alkyl.

3. A compound according to claim 2, wherein R[1] is halo, $C_1$–$C_6$-alkyl, or $CF_3$,, and R[2] is selected from alternate definition (ii), wherein R[5] is H or methyl, and R[7] is H.

4. A compound according to claim 1 selected from the group consisting of:
3-Methyl-5-(2(S)-pyrrolidinyl)-isoxazole;
3-Methyl-5-(1-methyl-2(S)-pyrrolidinyl)-isoxazole;
3-Ethyl-5-(2(S)-pyrrolidinyl)-isoxazole;
3-Ethyl-5-(1-methyl-2(S)-pyrrolidinyl)-isoxazole;
3-Methyl-5-(2(S)-pyrrolidinyl)-isothiazole;
3-Methyl-5-(1-methyl-2(S)-pyrrolidinyl)-isothiazole;
3-Benzyl-5-(1-methyl-2(S)-pyrrolidinyl)-isoxazole;
5-(1-Methyl-2(S)-pyrrolidinyl)-3-propyl-isoxazole;
3-n-Butyl-5-(1-methyl-2(S)-pyrrolidinyl)-isoxazole;
5-(1-Ethyl-2(S)-pyrrolidinyl)-3-methyl-isoxazole;
3-Methyl-5-(1-methyl-2(R)-pyrrolidinyl)-isoxazole;
3-Methyl-5-(2(R)-pyrrolidinyl)-isoxazole;
3-Ethyl-5-(2(R)-pyrrolidinyl)-isoxazole;
3-Ethyl-5-(1-methyl-2(R)-pyrrolidinyl)-isoxazole;
3-Methyl-5-(2(R)-pyrrolidinyl)-isothiazole;
3-Methyl-5-(1-methyl-2(R)-pyrrolidinyl)-isoxazole;
3-Methoxymethyl-5-(1-methyl-2(S)-pyrrolidinyl)-isoxazole;
3-Methyl-5-(trans-4-hydroxy-1-methyl-2-pyrrolidinyl)-isoxazole;
3-Methyl-5-(trans-4-fluoromethyl-1-methyl-2-pyrrolidinyl)-isoxazole;
3-Methyl-5-(cis-1-methyl-5-cyanomethyl-2-pyrrolidinyl)-isoxazole;
3-Methyl-5-(trans-1,4-dimethyl-2-pyrrolidinyl)-isoxazole;
3-Methyl-5-(trans-1,5-methyl-2-pyrrolidinyl)-isoxazole;
3-Methyl-5-(trans-1-methyl-4-ethyl-2-pyrrolidinyl)-isoxazole;
3-Bromo-5-(1-methyl-2(S)-pyrrolidinyl)-isoxazole;
5-(trans-1-Ethyl-4-methyl-2(S)-pyrrolidinyl)-3-methyl-isoxazole;
5-(trans-1-Methyl-4-methyl-2(S)-pyrrolidinyl)-3-methyl-isoxazole;
5-(1-Methyl-2(S)-pyrrolidinyl)-3-methoxy-isoxazole;
3-Methyl-5-(trans-1-methyl-5-fluoromethyl-2-pyrrolidinyl)-isoxazole;
3-Methyl-5-(trans-1-methyl-3-fluoromethyl-2-pyrrolidinyl)-isoxazole;
3-Trifluoromethyl-5-(1-methyl-2(S)-pyrrolidinyl)-isoxazole;
3,4-Dimethyl-5-(1-methyl-2-pyrrolidinyl)-isoxazole;
5-(2-Pyrrolidinyl)-isoxazole;
5-(1-Methyl-2-pyrrolidinyl)-isoxazole;
3-Methyl-5-(1-methyl-2(S)-pyrrolidinyl)-4-phenylmethyl-isoxazole;
3-Methyl-5-(1-methyl-2(S)-pyrrolidinyl)-4-ethyl-isoxazole;
3-Methyl-5-(2(R)-piperidinyl)-isoxazole;
3-Methyl-5-(1-methyl-2(R)-piperidinyl)-isoxazole;
3-Methyl-5-(2(S)-piperidinyl)-isoxazole;
3-Methyl-5-(2(S)-azetidinyl)-isoxazole;
3-Methyl-4-(1-methyl-2(S)-pyrrolidinyl)-1-phenyl-pyrazole; and
3-Methyl-5-(1-methyl-2(S)-pyrrolidinyl)-pyrazole;
or a pharmaceutically-acceptable salt thereof.

5. A compound according to claim 4 which is:
3-Methyl-5-(1-methyl-2 (S)-pyrrolidinyl)-isoxazole;
3-Ethyl-5-(1-methyl-2(S)-pyrrolidinyl)-isoxazole;
5-(1-Methyl-2(S)-pyrrolidinyl)-3-propyl-isoxazole;
3-n-Butyl-5-(1-methyl-2(S)-pyrrolidinyl)-isoxazole;
5-(1-Ethyl-2(S)-pyrrolidinyl)-3-methyl-isoxazole;
3-Methyl-5-(2(R)-pyrrolidinyl)-isoxazole;
3-Methyl-5-(1-methyl-2(R)-pyrrolidinyl)-isoxazole;
3-Ethyl-5-(2(R)-pyrrolidinyl)-isoxazole;
3-Ethyl-5-(1-methyl-2(R)-pyrrolidinyl)-isoxazole;
3-Methyl-5-(trans-1,4-dimethyl-2-pyrrolidinyl)-isoxazole;
3-Bromo-5-(1-methyl-2(S)-pyrrolidinyl)-isoxazole;
5-(trans-1-Ethyl-4-methyl-2(S)-pyrrolidinyl)-3-methyl-isoxazole;
5-(trans-1-Methyl-4-methyl-2(S)-pyrrolidinyl)-3-methyl-isoxazole;
5-(1-Methyl-2(S)-pyrrolidinyl)-3-methoxy-isoxazole ;or
3-Trifluoromethyl-5-(1-methyl-2(S)-pyrrolidinyl)-isoxazole;
or a pharmaceutically-acceptable salt thereof.

6. A compound according to claim 5 which is:
3-Methyl-5-(1-methyl-2(S)-pyrrolidinyl)-isoxazole;
3-Methyl-5-(2(R)-pyrrolidinyl)-isoxazole;
3-Bromo-5-(1-methyl-2(S)-pyrrolidinyl)-isoxazole; or
3-Trifluoromethyl-5-(1-methyl-2(S)-pyrrolidinyl)-isoxazole;
or a pharmaceutically-acceptable salt thereof.

7. 3-Methyl-5-(1-methyl-2(S)-pyrrolidinyl)-isoxazole or a pharmaceutically-acceptable salt thereof.

8. A pharmaceutical composition for treating anxiety or a cognitive, neurological, mental or attentional deficit disorder or petit mal absence epilepsy characterized by decreased neuronal cholinergic function comprising a pharmaceutically-acceptable carrier and a therapeutically-effective amount of a compound according to claim 1.

9. The composition of claim 7 wherein the compound is 3-methyl-5-(1-methyl-2(S)-pyrrolidinyl)-isoxazole or a pharmaceutically-acceptable salt thereof.

10. A method for treating dementia, hyperkinesia, mania, acute confusion petit mal absence epilepsy or attentional deficit disorders comprising administering to a host in need of such treatment a therapeutically-effective amount of a compound of claim 1.

11. A method according to claim 10, wherein the method of administration is a transdermal patch.

12. A method according to claim 10, wherein a therapeutically-effective amount of a peripheral cholinergic antagonist is also administered to a host in need of such treatment.

13. A method according to claim 10, wherein the dementia is Alzheimer's disease.

* * * * *